US006455502B1

(12) United States Patent
Bryant et al.

(10) Patent No.: US 6,455,502 B1
(45) Date of Patent: Sep. 24, 2002

(54) COMPOUNDS AND COMPOSITIONS AS PROTEASE INHIBITORS

(75) Inventors: Clifford M. Bryant, Millbrae; Barry A. Bunin, San Bruno; Erica A. Kraynack, Oakland; John W. Patterson, Mountain View, all of CA (US)

(73) Assignee: AXYS Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 09/526,090

(22) Filed: Mar. 15, 2000

Related U.S. Application Data
(60) Provisional application No. 60/124,420, filed on Mar. 15, 1999.

(51) Int. Cl.[7] .................... A61K 31/275; A61K 31/277; A61K 38/05; C07C 255/00; C07K 5/06
(52) U.S. Cl. .......................... 514/19; 514/20; 514/601; 514/602; 514/605; 514/613; 514/616; 514/617; 514/618; 514/625; 544/159; 544/168; 564/80; 564/83; 564/84; 564/85; 564/86; 564/95; 564/123; 564/152; 564/154; 564/155; 564/157; 564/160; 564/161; 564/162; 564/163; 564/193; 564/197; 564/198
(58) Field of Search ................ 514/18, 19, 20, 514/601, 602, 605, 613, 616, 617, 618, 625; 530/331; 544/159, 168; 564/80, 83, 84, 85, 86, 95, 123, 152, 154, 155, 157, 160, 161, 162, 163, 193, 197, 198

(56) References Cited

U.S. PATENT DOCUMENTS

| | | | | |
|---|---|---|---|---|
| 4,927,809 A | * | 5/1990 | Stuber | 514/20 |
| 6,353,017 B1 | * | 3/2002 | Altmann et al. | 514/428 |

FOREIGN PATENT DOCUMENTS

| | | |
|---|---|---|
| EP | 0 355 572 | 2/1990 |
| EP | 0 419 683 | 4/1991 |
| EP | 0 536 399 | 4/1993 |
| EP | 0 754 454 | 1/1997 |
| JP | S39-26878 | 5/1967 |
| JP | 42009133 | 5/1967 |
| JP | 63 301868 | 12/1988 |
| JP | 63-301868 | * 12/1988 |
| WO | WO 90/13561 | 11/1990 |
| WO | WO 95/13069 | 5/1995 |
| WO | WO 95/15309 | 6/1995 |
| WO | WO 95/24382 | 9/1995 |
| WO | WO 98 01133 | 1/1998 |
| WO | WO 98/08867 | 3/1998 |
| WO | WO 99 24460 | 5/1999 |
| WO | 00/48992 | 8/2000 |
| WO | WO 00/49007 | 8/2000 |
| WO | WO 00/49008 | 8/2000 |
| WO | WO 00/51998 | 9/2000 |
| WO | WO 00/55124 | 9/2000 |
| WO | WO 01/09110 A1 | 2/2001 |
| WO | WO 01/19816 A1 | 3/2001 |
| WO | WO 01/30772 A1 | 5/2001 |
| WO | WO 01/55125 A1 | 8/2001 |
| WO | WO 01/58886 A1 | 8/2001 |

OTHER PUBLICATIONS

Picken et al. Inhibition of bovine cathepsin B . . . Biochem. Soc. Trans. vol. 18, Part 2, p. 316, Apr. 1990.*

Suzue et al. Studies on Heptic Agents . . . Chem. Pharm. Bull. vol. 16, No. 8, pp. 1417–1432, Aug. 1968.*

Ashworth, et al. "4–Cyanothiazolidides as very potent, stable inhibitors of dipeptidyl peptidase IV," *Bioorganic & Med. Chem. Letters*, B,Oxford, 6(22):2745–2748 (1996).

Bergeman, Marco et al., "Studies on the reactivity of .alpha.–cyano.alpha–isocyano alkanoates. Versitile synthons for the assembly of imidazoles," *Helv.Chim. ACTA*, 82(6):909–918 (1999).

Dufour et al. "Engineering nitrile hydratase activity into a cysteine protease by a single mutation," *Bio.chemistry, US, Am. Chem. Soc.*, Easton, PA, 34(50):16382–16388 (1995).

Gour–Salin et al., "Inhibition of papain by peptide nitriles: conversion of the nitrile group into other functionalities via the papain:nitrile thiomidate ester adduct," *Can. J. of Chem*, CA, National Research Council. Ottawa, 69(8):1288–1297 (1991).

Li, et al. "Aminoacylpyrrolidine–2–nitriles: Potent and stable inhibitors of dipeptidyl–peptidase IV (CD 26)," *Archives of Biochem. and Bioph.*, 323(1)148–154 (1995).

Katritzky, et al, "Benzotriazole–assisted synthesis of alpha.–(acylamino) nitrites and a conceptually novel method for peptide elongation," *J. Chem. Soc.*, Perkin Trans. 1(7):1853–1857 (1990).

Lipshutz, et al. "Chiral induction in orginally racemic amino acids via 5–acyl and 5–acyloxyaminooxazoles," *Isr, J. Chem*. 27(1):49–55 (1986), abstract.

Lipshutz, et al. "Heterocycles as masked diamide/dipeptide equivalents. Formation and reactions of substituted 5–(acylamino)oxazoles as intermediates en route to the cyclopeptide alkaloids," *J. Am. Chem. Soc.*, 105(26):7703–7713 (1983).

Lipshutz, et al, "Oxazolophanes as masked cyclopeptide alkaloid equivalents: cyclic peptide chemistry without peptide couplings," *J. Am. Chem. Soc.*, 112(19):7032–7041 (1990).

Mcmath, et al. "Direct dialkylation of peptide nitriles. Application of the synthesis of 1–aminocyclopropane–1 carboxylic acid (Acc)–containing dipeptides," *Bull. Soc. Chim. Fr.* 134(1):105–110 (1997).

(List continued on next page.)

Primary Examiner—Jeffrey E. Russel
(74) Attorney, Agent, or Firm—Townsend and Townsend and Crew LLP

(57) ABSTRACT

The present invention relates to novel N-cyanomethyl amides which are cysteine protease inhibitors, the pharmaceutically acceptable salts and N-oxides thereof, their uses as therapeutic agents and the methods of their making.

15 Claims, No Drawings

OTHER PUBLICATIONS

Moser et al. "130 Poly (dipeptamidinium)–Salze: definition und metoden zur praparativen herstellung. poly (dipeptamidinium) salts: definition and methods of preperation," *Helvitica Chimica ACTA*, CH, Verlag, Basel 69:1224–1262 (1986).

North et al., "Synthetic studies towards cyclic peptides. Concise synthesis of thiazoline and thiazole containing amino acids," *Tetrahedron*, 46(24):8627–8290 (1990).

Nippon, K., "Patent Abstracts of Japan," Publication No. 63301868, 013(137)(1988), abstract.

Thompson et al. "Carboxyl–modified amino acids and peptides as protease inhibitors," *J. Med. Chem.*, 29(1):104–111 (1986).

Vargha, Eugen: "Peptide derivatives. VI. N–protected di– and tripeptide nitriles," *Stud. Univ. Babes–Bolyai, Ser. Chem.*, 13(2):31–5 (English abstract of article in Romanian) (1968).

Varghese "The structure and resonance Raman spectra—structure correlations for methyloxycarbonyl–L–phenylalanyl–L–alanine ethyl dithioester," *Can. J. Chem.*, 64(8):1668–1673 (1986).

Yamada, et al. "Studies of unusual amino acids and their peptides. IX. The synthetic study of bottomycins B1 and B2," *Bul. Chem. Soc.*, Jpn. 51(3):878–83 (1978), abstract.

Hanzlik, Robert P. et al.: "Reversible covalent binding of peptide nitriles to papain" Biochim. Biophys, Acta, vol. 1035, No. 1, 1990, pp. 62–70.

Suzue, Seigo et al.: "Hepatic agents. I. Synthesis of aminocyl (and hydroxyacyl) aminoacetonitriles" [translated abstract], Chem. and Pharm. Bull. (Tokyo) (1968), 16(8), 1417–32.

U.S. patent application No. 09/526,485, Bryant et al, filed Mar. 15, 2000.

\* cited by examiner

COMPOUNDS AND COMPOSITIONS AS PROTEASE INHIBITORS

This application claims the benefit under U.S.C. Sec 119 (e)(1) of prior filed U.S. Provisional Application 60/124,420 filed Mar. 15, 1999.

THE INVENTION

This application relates to compounds and compositions for treating diseases associated with cysteine protease activity, particularly diseases associated with activity of cathepsins B, K, L or S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

In one particular embodiment, the present invention relates to compounds of Formula (I):

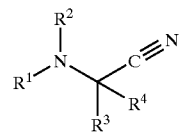

(I)

in which:
$R^1$ is a group of Formula (a) or (b):

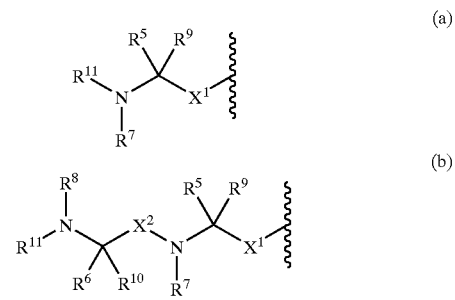

wherein:
$X^1$ and $X^2$ independently are —C(O)— or —CH$_2$S(O)$_2$—;
$R^5$ and $R^6$ are hydrogen or (C$_{1-6}$)alkyl;
$R^7$ and $R^8$ are hydrogen or (C$_{1-6}$)alkyl or as defined below;
$R^9$ and $R^{10}$ independently are (i) (C$_{1-6}$)alkyl optionally substituted with cyano, halo or nitro or (ii) a group selected from —X$^3$NR$^{12}$R$^{12}$, —X$^3$NR$^{12}$C(O)OR$^{12}$, —X$^3$NR$^{12}$C(O)NR$^{12}$R$^{12}$, —X$^3$NR$^{12}$C(NR$^{12}$)NR$^{12}$R$^{12}$, —X$^3$OR$^{12}$, —X$^3$SR$^{12}$, —X$^3$C(O)OR$^{12}$, —X$^3$C(O)NR$^{12}$R$^{12}$, —X$^3$S(O)$_2$NR$^{12}$R$^{12}$, —X$^3$P(O)(OR$^{12}$)OR$^{12}$, —X$^3$OP(O)(OR$^{12}$)R$^{12}$, —X$^3$NR$^{12}$C(O)R$^{13}$, —X$^3$S(O)R$^{13}$, —X$^3$S(O)$_2$R$^{13}$, —X$^3$C(O)R$^{13}$—X$^3$C(O)R$^{14}$, —X$^3$C(O)OR$^{14}$, —X$^3$OC(O)R$^{14}$, —X$^3$NR$^{15}$C(O)R$^{14}$, —X$^3$NR$^{15}$C(O)OR$^{14}$, —X$^3$C(O)NR$^{14}$R$^{15}$, —X$^3$S(O)$_2$NR$^{14}$R$^{15}$, —X$^3$NR$^{15}$C(O)NR$^{14}$R$^{15}$, —X$^3$NR$^{15}$C(NR$^{15}$)NR$^{14}$R$^{15}$, —X$^4$SR$^{14}$—X$^4$S(O)R$^{14}$, —X$^4$S(O)$_2$R$^{14}$, —X$^4$OR$^{14}$, or —X$^4$NR$^{14}$R$^{15}$, wherein X$^3$ is (C$_{1-6}$)alkylene, X$^4$ is a bond or (C$_{1-6}$)alkylene, R$^{12}$ at each occurrence independently is hydrogen, (C$_{1-6}$)alkyl or halo-substituted (C$_{1-3}$)alkyl, R$^{13}$ is (C$_{1-6}$)alkyl or halo-substituted (C$_{1-3}$)alkyl, R$^{14}$ is (C$_{3-12}$)cycloalkyl (C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl (C$_{9-12}$)polycycloaryl(C$_{0-6}$)alkyl or hetero(C$_{8-12}$) polycycloaryl(C$_{0-6}$)alkyl and R$^{15}$ is hydrogen or (C$_{1-6}$)alkyl, and wherein within R$^{14}$ said cycloalkyl, heterocycloalkyl, aryl, heteroaryl, polycycloaryl or heterpolycycloaryl ring optionally is substituted by a group selected from —R$^{16}$, —X$^4$OR$^{16}$, —X$^4$SR$^{16}$, —X$^4$S(O)R$^{16}$, —X$^4$S(O)$_2$R$^{16}$, —X$^4$C(O)R$^{16}$, —X$^4$C(O)OR$^{16}$, —X$^4$OC(O)R$^{16}$, —X$^4$NR$^{16}$R$^{17}$, —X$^4$NR$^{17}$C(O)R$^{16}$, —X$^4$NR$^{17}$C(O)OR$^{16}$, —X$^4$C(O)NR$^{16}$R$^{17}$, —X$^4$S(O)$_2$NR$^{16}$R$^{17}$, —X$^4$NR$^{17}$C(O)NR$^{16}$R$^{17}$ OR —X$^4$NR$^{17}$C(NR$^{17}$)NR$^{16}$R$^{17}$, wherein X$^4$ is a bond or (C$_{1-6}$)alkylene, R$^{16}$ is hydrogen or (C$_{1-6}$)alkyl and R$^{17}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$) alkyl, hetero(C$_{5-12}$)aryl(C$_{0-6}$)alkyl, (C$_{9-12}$) polycycloaryl(C$_{0-6}$)alkyl or hetero(C$_{8-12}$) polycycloaryl(C$_{0-6}$)alkyl, or (iii) a group selected from $(C_{3-12})$cycloalkyl$(C_{0-6})$alkyl, hetero$(C_{3-12})$ cycloalkyl$(C_{0-6})$alkyl, $(C_{6-12})$aryl$(C_{0-6})$alkyl hetero $(C_{5-12})$aryl$(C_{0-6})$alkyl, $(C_{9-12})$polycycloaryl$(C_{0-6})$ alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^{16}$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-X^4NR^{17}C(O)OR^{16}$, $-X^4(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$, $R^{16}$ and $R^{17}$ are as defined above; wherein within $R^9$ and/or $R^{10}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)R^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^4)OR^{12}$, $-X^4OP(O)(OR^{12})OR^{12}$, $-X^4OC(O)R^{13}$, $-X^4NR^{12}C(O)R^{13}$, $-X^4S(O)R^{13}$, $-X^4S(O)_2R^{13}$ and $-X^4C(O)R^{13}$, wherein $X^4$, $R^{12}$ and $R^{13}$ are as defined above, or $R^9$ taken together with $R^7$ and/or $R^{10}$ taken together with $R^8$ form trimethylene, tetramethylene or phenylene-1,2-dimethylene, optionally substituted with hydroxy, oxo or methylene; and $R^{11}$ is $-X^5X^6R^{18}$, wherein $X^5$ is $-C(O)-$, $-C(O)C(O)-$ or $-S(O)_2-$, $X^6$ is a bond, $-O-$ or $-NR^{19}-$, wherein $R^{19}$ is hydrogen or $(C_{1-6})$alkyl, and $R^{18}$ is (i) $(C_{1-10})$alkyl optionally substituted by cyano, halo, nitro, $-NR^{12}R^{12}$, $-NR^{12}C(O)OR^{12}$, $-NR^{12}C(O)NR^{12}R^{12}$, $-NR^{12}C(NR^{12})NR^{12}R^{12}$, $-OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{20}$, $-SR^{20}$, $-S(O)R^{20}$, $-S(O)_2R^{20}$, $-C(O)R^{20}$, $-C(O)OR^{20}$, $-C(O)NR^{20}R^{21}$, $-NR^{20}R^{21}$, $-NR^{21}C(O)R^{20}$, $-NR^{21}(O)OR^{20}$, $-NR^{21}C(O)NR^{20}R^{21}$ or $-NR^{21}C(NR^{21})NR^{21}$, wherein $R^{12}$ and $R^{13}$ are as defined above, $R^{20}$ is $(C_{3-12})$cycloalkyl$(C_{0-6})$alkyl, hetero$(C_{3-12})$ cycloalkyl$(C_{0-6})$alkyl, $(C_{6-12})$aryl$(C_{0-6})$alkyl, hetero $(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl and $R^{21}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$ alkyl, hetero$(C_{5-12})$aryl$(C_{0-6})$alkyl, $(C_{9-12})$ bicycloaryl$(C_{0-6})$alkyl or hetero$(C_{8-12})$bicycloaryl $(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl is substituted by $-X^4OR^{22}$, $-X^4SR^{22}$, $-X^4S(O)R^{22}$, $-X^4S(O)_2R^{22}$, $-X^4C(O)R^{22}$, $-X^4C(O)OR^{22}$, $-X^4C(O)NR^{22}R^{23}$, $-X^4NR^{22}R^{23}$, $-X^4NR^{23}C(O)R^{22}$, $-X^4NR^{23}C(O)OR^{22}$, $-X^4NR^{23}C(O)NR^{22}R^{23}$ or $-X^4NR^{23}C(NR^{23})NR^{22}R^{23}$, wherein $X^4$ is as defined above, $R^{22}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP(O)(OR^3)OR^{12}$, $-X^4OC(O)R^{13}$, $-X^4NR^{12}C(O)R^{13}$, $-X^4S(O)R^{13}$, $-X^4S(O)_2R^{13}$, and $-X^4C(O)R^{13}$, wherein $X^4$, $R^{12}$ and $R^{13}$ are as defined above;

$R^2$ is hydrogen or $(C_{1-6})$alkyl or as defined below;

$R^3$ is hydrogen, $(C_{1-6})$alkyl or as defined below; and $R^4$ is (i) hydrogen or $(C_{1-6})$alkyl, wherein said alkyl is optionally substituted with cyano, halo, nitro, $-NR^{12}R^{12}$, $-NR^{12}C(O)OR^{12}$, $-NR^{12}C(O)NR^{12}R^{12}$, $-NR^{12}C(NR^{12})NR^{12}R^{12}$, $-OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{14}$, $-SR^{14}$, $-S(O)R^{14}$, $-S(O)_2R^{14}$, $-C(O)R^{14}$, $-C(O)OR^{14}$, $-OC(O)R^{14}$, $-NR^{14}R^{15}$, $-NR^{15}C(O)R^{14}$, $-NR^{15}C(O)OR^{14}$, $-C(O)NR^{14}R^{15}$, $-S(O)_2NR^{14}R^{15}$, $-NR^{15}C(O)NR^{14}R^{15}$ or $-NR^{15}C(NR^{15})NR^{14}R^{15}$, wherein $R^{12}$, $R^{13}$, $R^{14}$ and $R^{15}$ are as defined above, or (ii) A group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$ alkyl, hetero$(C_{5-12})$aryl$(C_{0-6})$alkyl, $(C_{9-12})$ polycycloaryl$(C_{0-6})$alkyl and hetero$(C_{8-12})$ polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^6$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-X^4NR^{17}C(O)OR^{16}$, $-X^4C(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$, $R^{16}$ and $R^{17}$ are as defined above; wherein within $R^9$ and/or $R^{10}$ any alicyclic or aromatic ring system present may be substituted further by 1 to 5 radicals independently selected from $(C_{1-6})$alkyl, $(C_{1-6})$ alkylidene, cyano, halo, halo-substituted $(C_{1-4})$alkyl, nitro, $-X^4NR^{12}R^{12}$, $X^4NR^{12}C(O)R^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP(O)(OR^3)OR^{12}$, $-X^4OC(O)R^{13}$, $-X^4NR^{12}C(O)R^{13}$, $-X^4S(O)R^{13}$, $-X^4S(O)_2R^{13}$ and $-X^4C(O)R^{13}$, wherein $X^4$, $R^{12}$ and $R^{13}$ are as defined above, or $R^4$ and $R^2$ taken together form trimethylene, tetramethylene or phenylene-1,2-dimethylene, optionally substituted with hydroxy, oxo or methylene, or $R^4$ and $R^3$ together with the carbon atom to which both $R^4$ and $R^3$ are attached form $(C_{3-8})$cycloalkylene or $(C_{3-8})$heterocycloalkylene; and the N-oxide derivatives, prodrug derivatives, protected derivatives, individual isomers and mixtures of isomers; and the pharmaceutically acceptable salts thereof.

In another particular embodiment, this invention relates to compounds of Formula (II):

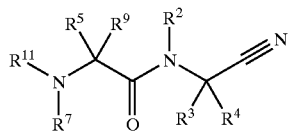

(II)

wherein:
  $R^2$ is hydrogen or $(C_{1-6})$alkyl or as defined below;
  $R^3$ is hydrogen, $(C_{1-6})$alkyl or as defined below;
  $R^4$ is (i) hydrogen or $(C_{1-6})$alkyl, wherein said alkyl optionally is substituted with cyano, halo, nitro, $-NR^{12}R^{12}$, $-NR^{12}C(O)OR^{12}$, $-NR^{12}C(O)NR^{12}R^{12}$, $-NR^{12}C(NR^{12})NR^{12}R^{12}$, $-OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{14}$, $-SR^{14}$, $-S(O)R^{14}$, $-S(O)_2R^{14}$, $-C(O)R^{14}$, $-C(O)OR^{14}$, $-OC(O)R^{14}$, $-NR^{14}R^{15}$, $-NR^{15}C(O)R^{14}$, $-NR^{15}C(O)OR^{14}$, $-C(O)NR^{14}R^{15}$, $-S(O)_2NR^{14}R^{15}$, $-NR^{15}C(O)NR^{14}R^{15}$ or $-NR^{15}C(NR^{15})NR^{14}R^{15}$, wherein $R^{12}$ at each occurrence independently is hydrogen, $(C_{1-6})$alkyl or halo-substituted $(C_{1-3})$alkyl, $R^{13}$ is $(C_{1-6})$alkyl or halo-substituted $(C_{1-3})$alkyl, $R^{14}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl and $R^{15}$ is hydrogen or $(C_{1-6})$alkyl, and wherein within $R^{14}$ said cycloalkyl, heterocycloalkyl, aryl, heteroaryl, polycycloaryl or heterpolycycloaryl ring optionally is substituted by a group selected from $-R^{16}$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-X^4NR^{17}C(O)OR^{16}$, $-X^4C(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$ is a bond or $(C_{1-6})$alkylene, $R^{16}$ is hydrogen or $(C_{1-6})$alkyl and $R^{17}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl, or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^6$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-X^4NR^{17}C(O)OR^{16}$, $-X^4C(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$, $R^{16}$ and $R^{17}$ are as defined above; wherein within $R^4$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP(O)(OR^3)OR^{12}$, $-X^4OC(O)R^{13}$, $-X^4NR^{12}C(O)R^{13}$, $-X^4S(O)R^{13}$, $-X^4S(O)_2R^{13}$ and $-X^4C(O)R^{13}$, wherein $X^4$, $R^{12}$ and $R^{13}$ are as defined above, or $R^4$ and $R^2$ taken together form trimethylene, tetramethylene or phenylene-1,2-dimethylene, optionally substituted with hydroxy, oxo or methylene, or $R^4$ and $R^3$ together with the carbon atom to which both $R^4$ and $R^3$ are attached form $(C_{3-8})$cycloalkylene or $(C_{3-8})$heterocycloalkylene;

$R^5$ is hydrogen or $(C_{1-6})$alkyl;

$R^7$ is hydrogen or $(C_{1-6})$alkyl;

$R^9$ is $(C_{6-12})$aryl$(C_{1-6})$alkyl, hetero$(C_{5-12})$aryl$(C_{1-6})$alkyl, $-X^4OR^4$, $-X^4SR^{14}$, $-X^4S(O)R^{14}$, $-X^4S(O)_2R^{14}$ or $-X^4NR^{14}R^{15}$, wherein $X^4$, $R^{14}$ and $R^{15}$ are as defined above and wherein within $R^9$ said aryl or heteroaryl ring optionally is substituted by 1 to 5 radicals independently selected from $(C_{1-6})$alkyl, cyano, halo, halo-substituted $(C_{1-4})$alkyl, nitro, $-X^4NR^{12}R^{12}$, $-X^4NR^{12}C(O)R^{12}$, $X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)R^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP(O)(OR^3)OR^{12}$, $-X^4OC(O)R^{13}$, $-X^4NR^{12}C(O)R^{13}$, $-X^4S(O)R^{13}$, $-X^4S(O)_2R^{13}$, wherein $X^4$, $R^{12}$ and $R^{13}$ are as defined above; and $R^{11}$ is $-X^5X^6R^{18}$, wherein $X^5$ is $-C(O)-$, $-C(O)C(O)-$ or $-S(O)_2-$, $X^6$ is a bond, $-O-$ or $-NR^{19}-$, wherein $R^{19}$ is hydrogen or $(C_{1-6})$alkyl, and $R^{18}$ is (i) $(C_{1-10})$alkyl optionally substituted by cyano, halo, nitro, $-NR^{12}R^{12}$, $-NR^{12}C(O)OR^{12}$, $-NR^{12}C(O)NR^{12}R^{12}$, $-NR^{12}C(NR^{12})NR^{12}R^{12}$, $-OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{20}$, $-SR^{20}$, $-S(O)R^{20}$, $-S(O)_2R^{20}$, $-C(O)R^{20}$, $-C(O)OR^{20}$, $-C(O)NR^{20}R^{21}$, $-NR^{20}R^{21}$, $-NR^{21}C(O)R^{20}$, $-NR^{21}C(O)OR^{20}$, $-NR^{21}C(O)NR^{20}OR^{21}$ or $-NR^{21}C(NR^{21})NR^{20}R^{21}$, wherein $R^{12}$ and $R^{13}$ are as defined above, $R^{20}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl and $R^{21}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl $(C_{9-12})$bicycloaryl$(C_{0-6})$alkyl or hetero$(C_{8-12})$bicycloaryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl is substituted by $-X^4OR^{22}$, $-X^4SR^{22}$, $-X^4S(O)R^{22}$, $-X^4S(O)_2R^{22}$, $-X^4C(O)R^{22}$, $-X^4C(O)OR^{22}$, $-X^4C(O)NR^{22}R^{23}$, $-X^4NR^{22}R^{23}$, $-X^4NR^{23}C(O)R^{22}$, $-X^4NR^{23}C(O)OR^{22}$, $-X^4NR^{23}C(O)NR^{22}R^{23}$ or $-X^4NR^{23}C(NR^{23})NR^{22}R^{23}$, wherein $X^4$ is as defined above, $R^{22}$ is $(C_{3-6})$cycloalkyl$(C_{0-6})$alkyl, hetero$(C_{3-6})$cycloalkyl$(C_{0-6})$alkyl, phenyl$(C_{0-6})$alkly or hetero$(C_{5-6})$aryl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP$ $(O)(OR^3)OR^{12}$, —$X^4OC(O)R^{13}$, —$X^4NR^{12}C(O)R^{13}$, —$X^4S(O)R^{13}$, —$X^4S(O)_2R^{13}$ and —$X^4C(O)R^{13}$, wherein $X^4$, $R^{12}$ and $R^{13}$ are as defined above; and the N-oxide derivatives, prodrug derivatives, protected derivatives, individual isomers and mixtures of isomers; and the pharmaceutically acceptable salts thereof.

In another particular embodiment, the present invention relates to a pharmaceutical composition which contains a compound of Formula I or a N-oxide derivative, prodrug derivative, individual isomer or mixture of isomers or a pharmaceutically acceptable salt thereof in admixture with one or more suitable excipients.

In another particular embodiment, the present invention relates to a method of treating a disease in an animal in which inhibition of a cysteine protease can prevent, inhibit or ameliorate the pathology and/or symptomatology of the disease, which method comprises administering to the animal a therapeutically effective amount of compound of Formula I or a N-oxide derivative, prodrug derivative, individual isomer or mixture of isomers or a pharmaceutically acceptable salt thereof.

In another particular embodiment, the present invention relates processes for preparing compounds of Formula I and the N-oxide derivatives, prodrug derivative, protected derivatives, individual isomers and mixtures of isomers, and the pharmaceutically acceptable salts thereof as set forth in "Detailed Description of the Invention".

In another particular embodiment, the present invention relates a compound of Formula (III):

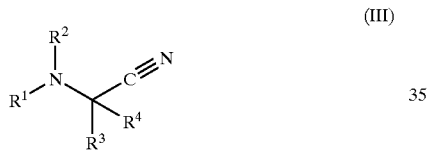

(III)

in which:

$R^1$ is a group of Formula (a) or (b):

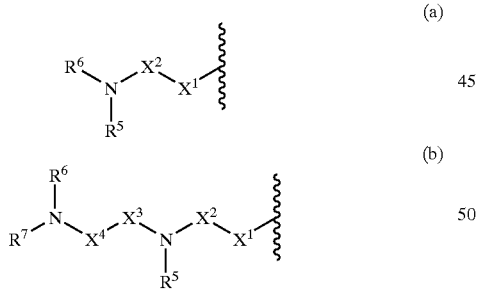

wherein:

$X^1$ and $X^3$ independently are —C(O)— or —S(O)$_2$—,
$X^2$ is —$CR^8R^9$—, —$CH_2CR^8R^9$— or —$CR^8R^9CH_2$—
and $X^4$ is —$CHR^{10}$—, —$CH_2CHR^{10}$— or —$CHR^{10}OCH_2$—, wherein:
$R^8$ is hydrogen or $(C_{1-6})$alkyl,
$R^9$ is (i) $(C_{1-6})$alkyl or halo-substituted$(C_{1-6})$alkyl optionally substituted with —$OR^{11}$, —$SR^{11}$, —$S(O)R^{11}$, —$S(O)_2R^{11}$, —$C(O)R^{11}$, —$C(O)OR^{11}$, —$NR^{11}R^{12}$, —$NR^{12}C(O)OR^{11}$, —$C(O)NR^{11}R^{12}$, —$S(O)_2NR^{11}R^{12}$, —$NR^{12}C(O)NR^{11}R^{12}$ or —$NR^{12}C(NR^{12})NR^{11}R^{12}$, wherein $R^{11}$ is hydrogen, $(C_{1-6})$alkyl, $(C_{3-12})$cycloalkyl $(C_{0-3})$alkyl, hetero$(C_{3-12})$cycloalkyl$(C_{0-3})$alkyl, $(C_{6-12})$aryl$(C_{0-3})$alkyl or hetero$(C_{5-12})$aryl$(C_{0-3})$ alkyl and $R^{12}$ is hydrogen or $(C_{1-6})$alkyl, or (ii) $(C_{3-12})$cycloalkyl$(C_{0-3})$alkyl, hetero$(C_{3-12})$ cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl $(C_{0-3})$alkyl or hetero$(C_{8-12})$polycycloaryl$(C_{0-3})$ alkyl optionally substituted with —$R^{13}$, —$X^5OR^{13}$, —$X^5SR^{13}$, —$S(O)R^{13}$, —$S(O)_2R^{13}$, —$C(O)R^{13}$, —$C(O)OR^{13}$, —$X^5NR^{13}R^{14}$, —$X^5NR^{14}C(O)OR^{13}$, —$C(O)NR^{13}R^{14}$, —$S(O)_2NR^{13}R^{14}$, —$NR^{14}C(O)NR^{13}R^{14}$ or —$NR^{14}C(NR^{14})NR^{13}R^{14}$, wherein $X^5$ is a bond or methylene, $R^{13}$ is $(C_{3-12})$cycloalkyl$(C_{0-3})$alkyl, hetero$(C_{3-12})$cycloalkyl$(C_{0-3})$alkyl, $(C_{6-12})$aryl $(C_{0-3})$alkyl, hetero$(C_{5-12})$aryl$(C_{0-3})$alkyl, $(C_{9-12})$ polycycloaryl$(C_{0-3})$alkyl or hetero$(C_{8-12})$ polycycloaryl$(C_{0-3})$alkyl and $R^{14}$ is hydrogen or $(C_{1-6})$alkyl, or (iii) together with $R^5$ when $X^2$ is —$CHR^9$— forms trimethylene, tetramethylene or phenylene-1,2-dimethylene, optionally substituted with 1 to 2 of hydroxy, oxo, $(C_{1-4})$alkyl or methylene; wherein any 1 to 3 annular atoms of any aromatic ring with available valences comprising $R^9$ are optionally independently substituted with halo, nitro, cyano, $(C_{1-6})$alkyl, halo-substituted$(C_{1-6})$alkyl, —$OR^{15}$, —$C(O)R^{15}$, —$C(O)OR^{15}$, —$C(O)NR^{15}R^{15}$, —$S(O)_2NR^{15}R^{15}$, —$X^5NR^{15}R^{15}$, —$X^5NR^{15}C(O)OR^{15}$, —$X^5NR^{15}C(O)NR^{15}$ or —$X^5NR^{15}C$ $(NR^{15}NR^{15}R^{15}$, wherein $X^5$ is as defined above and each $R^{15}$ independently is hydrogen or $(C_{1-6})$alkyl, and
$R^{10}$ is hydrogen or $(C_{1-4})$alkyl;
$R^5$ and $R^7$ are independently hydrogen, $(C_{1-6})$alkyl or as defined above; and
$R^6$ is —$X^6X^7R^{16}$, wherein $X^6$ is —C(O)— or —$S(O)_2$—, $X^7$ is a bond, —O— or —$NR^{17}$—, wherein $R^{17}$ is hydrogen or $(C_{1-6})$alkyl, and $R^{16}$ is (i) $(C_{1-6})$alkyl or halo-substituted$(C_{1-6})$alkyl optionally substituted with —$OR^{11}$, —$SR^{11}$, —$S(O)R^{11}$, —$S(O)_2R^{11}$, —$C(O)R^{11}$, —$C(O)OR^{11}$, —$NR^{11}R^{12}$, —$NR^{12}C(O)OR^{11}$, —$C(O)NR^{11}R^{12}$, —$NR^{12}C(O)$ $NR^{11}R^{12}$ or —$NR^{12}C(NR^{12})NR^{11}R^{12}$, wherein $R^{11}$ and $R^{12}$ are as defined above, or (ii) $(C_{3-6})$cycloalkyl $(C_{0-3})$alkyl, hetero$(C_{3-6})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl$(C_{0-3})$alkyl or hetero$(C_{8-12})$ polycycloaryl$(C_{0-3})$alkyl optionally substituted with 1 to 2 of —$R^{13}$, —$X^5OR^{13}$, —$X^5SR^{13}$, —$S(O)R^{13}$, —$S(O)_2R^{13}$, —$C(O)OR^{13}$, —$X^5NR^{13}R^{14}$, —$X^5NR^{14}C(O)OR^{13}$, —$C(O)NR^{13}R^{14}$, —$NR^{14}C$ $(O)NR^{13}R^{14}$ or —$NR^{14}C(NR^{14})NR^{13}R^{14}$, wherein $X^5$, $R^{13}$ and $R^{14}$ are as defined above; wherein any 1 to 3 annular atoms of any aromatic ring with available valences comprising $R^{16}$ optionally independently are substituted with halo, nitro, cyano, $(C_{1-6})$alkyl, halo-substituted$(C_{1-6})$alkyl, —$OR^{15}$, —$C(O)R^{15}$, —$C(O)OR^{15}$, —$C(O)NR^{15}R^{15}$, —$S(O)_2NR^{15}R^{15}$, —$X^5NR^{15}R^{15}$, —$X^5NR^{15}C(O)$ $R^{15}$, —$X^5NR^{15}C(O)NR^{15}R^{15}$ or —$X^5NR^{15}C(NR^{15})$ $NR^{15}R^{15}$, wherein $X^5$ and $R^{15}$ are as defined above;
$R^2$ is hydrogen or $(C_{1-6})$alkyl or as defined below;
$R^3$ is hydrogen, $(C_{1-10})$alkyl or as defined below; and
$R^4$ is (i) hydrogen, (ii) $(C_{1-6})$alkyl or halo-substituted $(C_{1-6})$alkyl optionally substituted with —$OR^{11}$, —$SR^{11}$, —$S(O)R^{11}$, —$S(O)_2R^{11}$, —$C(O)R^{11}$, —$C(O)$ OR$^{11}$, —NR$^{11}$R$^{12}$, —NR$^{12}$C(O)OR$^{11}$, —C(O)NR$^{11}$R$^{12}$, —NR$^{12}$C(O)NR$^{11}$R$^{12}$ or —NR$^{12}$C(NR$^{12}$)NR$^{11}$R$^{12}$, wherein R$^{11}$ and R$^{12}$ are as defined above, or (iii) (C$_{3-12}$)cycloalkyl(C$_{0-3}$)alkyl, hetero(C$_{3-12}$)cycloalkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)polycycloaryl(C$_{0-3}$)alkyl or hetero(C$_{8-12}$)polycycloaryl(C$_{0-3}$)alkyl optionally substituted with —R$^{13}$, —X$^5$OR$^{13}$, —X$^5$SR$^{13}$, —S(O)R$^{13}$, —S(O)$_2$R$^{13}$, —C(O)OR$^{13}$, —X$^5$NR$^{13}$R$^{14}$, —X$^5$NR$^{14}$C(O)OR$^{13}$, —C(O)NR$^{13}$R$^{14}$, —NR$^{14}$C(O)NR$^{13}$R$^{14}$ or —NR$^{14}$C(NR$^{14}$)NR$^{13}$R$^{14}$, wherein X$^5$, R$^{13}$ and R$^{14}$ are as defined above or (iv) together with R$^2$ forms trimethylene, tetramethylene or phenylene-1,2-dimethylene, optionally substituted with hydroxy, oxo, (C$_{1-4}$)alkyl or methylene or (v) together with R$^3$ forms ethylene, trimethylene or tetramethylene; wherein any 1 to 3 annular atoms of any aromatic ring with available valences comprising R$^4$ optionally independently are substituted with halo, nitro, cyano, (C$_{1-6}$)alkyl, halo-substituted(C$_{1-6}$)alkyl, —OR$^{15}$, —C(O)R$^{15}$, —C(O)OR$^{15}$, —C(O)NR$^{15}$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$)NR$^{15}$R$^{15}$, wherein X$^5$ and R$^{15}$ are as defined above; and the N-oxide derivatives, prodrug derivatives, protected derivatives, individual isomers and mixtures of isomers; and the pharmaceutically acceptable salts thereof.

In another particular embodiment, the present invention relates to a method of treating a disease in an animal in which cathepsin S activity contributes to the pathology and/or symptomatology of the disease, which method comprising administering to the animal a therapeutically effective amount of a compound of Formula (I):

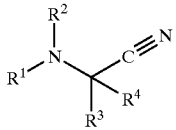
(I)

in which:

R$^1$ is a group of Formula (a) or (b):

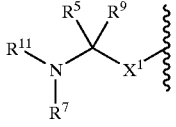
(a)

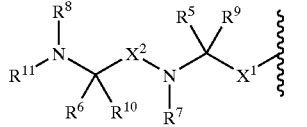
(b)

wherein:

X$^1$ and X$^2$ independently are —C(O)— or —CH$_2$S(O)$_2$—;

R$^5$ and R$^6$ are hydrogen or (C$_{1-6}$)alkyl;

R$^7$ and R$^8$ are hydrogen or (C$_{1-6}$)alkyl or as defined below;

R$^9$ and R$^{10}$ independently are (i) (C$_{1-6}$)alkyl optionally substituted with cyano, halo or nitro or (ii) a group selected from —X$^3$NR$^{12}$R$^{12}$, —X$^3$NR$^{12}$C(O)OR$^{12}$, —X$^3$NR$^{12}$C(O)NR$^{12}$R$^{12}$, —X$^3$NR$^{12}$C(NR$^{12}$)NR$^{12}$R$^{12}$, —X$^3$OR$^{12}$, —X$^3$SR$^{12}$, —X$^3$C(O)OR$^{12}$, —X$^3$C(O)NR$^{12}$R$^{12}$, —X$^3$S(O)$_2$NR$^{12}$R$^{12}$, —X$^3$P(O)(OR$^{12}$)OR$^{12}$, —X$^3$OP(O)(OR$^{12}$)OR$^{12}$, —X$^3$NR$^{12}$C(O)R$^{13}$, —X$^3$S(O)R$^{13}$, —X$^3$S(O)$_2$R$^{13}$, —X$^3$C(O)R$^{13}$, —X$^3$C(O)R$^{14}$, —X$^3$C(O)OR$^{14}$, —X$^3$OC(O)R$^{14}$, —X$^3$NR$^{15}$C(O)R$^{14}$, —X$^3$NR$^{15}$C(O)OR$^{14}$, —X$^3$C(O)NR$^{14}$R$^{15}$, —X$^3$S(O)$_2$NR$^{14}$R$^{15}$, —X$^3$NR$^{15}$C(O)NR$^{14}$R$^{15}$, —X$^3$NR$^{15}$C(NR$^{15}$)NR$^{14}$R$^{15}$, —X$^4$SR$^{14}$—X$^4$S(O)R$^{14}$, —X$^4$S(O)$_2$R$^{14}$, —X$^4$OR$^{14}$, or —X$^4$NR$^{14}$R$^{15}$, wherein X$^3$ is (C$_{1-6}$)alkylene, X$^4$ is a bond or (C$_{1-6}$)alkylene, R$^{12}$ at each occurrence independently is hydrogen, (C$_{1-6}$)alkyl or halo-substituted (C$_{1-3}$)alkyl, R$^{13}$ is (C$_{1-6}$)alkyl or halo-substituted (C$_{1-3}$)alkyl, R$^{14}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl (C$_{9-12}$)polycycloaryl(C$_{0-6}$)alkyl or hetero(C$_{8-12}$)polycycloaryl(C$_{0-6}$)alkyl and R$^{15}$ is hydrogen or (C$_{1-6}$)alkyl, and wherein within R$^{14}$ said cycloalkyl, heterocycloalkyl, aryl, heteroaryl, polycycloaryl or heterpolycycloaryl ring optionally is substituted by a group selected from —R$^{16}$, —X$^4$OR$^{16}$, —X$^4$SR$^{16}$, —X$^4$S(O)R$^{16}$, —X$^4$S(O)$_2$R$^{16}$, —X$^4$C(O)R$^{16}$, —X$^4$C(O)OR$^{16}$, —X$^4$OC(O)R$^{16}$, —X$^4$NR$^{16}$R$^{17}$, —X$^4$NR$^{17}$C(O)R$^{16}$, —X$^4$NR$^{17}$C(O)OR$^{16}$, —X$^4$C(O)NR$^{16}$R$^{17}$, —X$^4$S(O)$_2$NR$^{16}$R$^{17}$, —X$^4$NR$^{17}$C(O)NR$^{16}$R$^{17}$ or —X$^4$NR$^{17}$C(NR$^{17}$)NR$^{16}$R$^{17}$, wherein X$^4$ is a bond or (C$_{1-6}$)alkylene, R$^{16}$ is hydrogen or (C$_{1-6}$)alkyl and R$^{17}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)polycycloaryl(C$_{0-6}$)alkyl, or (iii) a group selected from (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl and hetero(C$_{8-12}$)polycycloaryl(C$_{0-6}$)alkyl, wherein said cycloalkyl, heterocycloalkyl, aryl, heteroaryl, polycycloaryl or heterpolycycloaryl ring optionally is substituted by a group selected from —R$^{16}$, —X$^4$OR$^{16}$, —X$^4$SR$^{16}$, —X$^4$S(O)R$^{16}$, —X$^4$S(O)$_2$R$^{16}$, —X$^4$C(O)R$^{16}$, —X$^4$C(O)OR$^{16}$, —X$^4$OC(O)R$^{16}$, —X$^4$NR$^{16}$R$^{17}$, —X$^4$NR$^{17}$C(O)R$^{16}$, —X$^4$NR$^{17}$C(O)OR$^{16}$, —X$^4$C(O)NR$^{16}$R$^{17}$, —X$^4$S(O)$_2$NR$^{16}$R$^{17}$, —X$^4$NR$^{17}$C(O)NR$^{16}$R$^{17}$ or —X$^4$NR$^{17}$C(NR$^{17}$)NR$^{16}$R$^{17}$, wherein X$^4$, R$^{16}$ and R$^{17}$ are as defined above; wherein within R$^9$ and/or R$^{10}$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^4$NR$^{12}$R$^{12}$, —X$^4$NR$^{12}$C(O)OR$^{12}$, —X$^4$NR$^{12}$C(O)NR$^{12}$R$^{12}$, —X$^4$NR$^{12}$C(NR$^{12}$)NR$^{12}$R$^{12}$, —X$^4$OR$^{12}$, —X$^4$SR$^{12}$, —X$^4$C(O)OR$^{12}$, —X$^4$C(O)NR$^{12}$R$^{12}$, —X$^4$S(O)$_2$NR$^{12}$R$^{12}$, —X$^4$P(O)(OR$^4$)OR$^{12}$, —X$^4$OP(O)(OR$^{12}$)OR$^{12}$, —X$^4$OC(O)R$^{13}$, —X$^4$NR$^{12}$C(O)R$^{13}$, —X$^4$S(O)R$^{13}$, —X$^4$S(O)$_2$R$^{13}$ and —X$^4$C(O)R$^{13}$, wherein X$^4$, R$^{12}$ and R$^{13}$ are as defined above, or R$^9$ taken together with R$^7$ and/or R$^{10}$ taken together with R$^8$ form trimethylene, tetramethylene or phenylene-1,2-dimethylene, optionally substituted with hydroxy, oxo or methylene; and R$^{11}$ is —X$^5$X$^6$R$^{18}$, wherein X$^5$ is —C(O)—, —C(O)C(O)— or —S(O)$_2$—, X$^6$ is a bond, —O— or —NR$_{19}$—, wherein R$^{19}$ is hydrogen or (C$_{1-6}$)alkyl, and R$^{18}$ is (i) (C$_{1-10}$)alkyl optionally substituted by cyano, halo, nitro, —NR$^{12}$R$^{12}$, —NR$^{12}$C(O)OR$^{12}$, —NR$^{12}$C(O)NR$^{12}$R$^{12}$, —NR$^{12}$C(NR$^{12}$)NR$^{12}$R$^{12}$, —$OR^{12}$, —$SR^{12}$, —$C(O)OR^{12}$, —$C(O)NR^{12}R^{12}$, —$S(O)_2NR^{12}R^{12}$, —$P(O)(OR^{12})OR^{12}$, —$OP(O)(OR^{12})OR^{12}$, —$NR^{12}C(O)R^{13}$, —$S(O)R^{13}$, —$S(O)_2R^{13}$, —$C(O)R^{13}$, —$OR^{20}$, —$SR^{20}$, —$S(O)R^{20}$, —$S(O)_2R^{20}$, —$C(O)R^{20}$, —$C(O)OR^{20}$, —$C(O)NR^{20}R^{21}$, —$NR^{12}R^{21}$, —$NR^{21}C(O)R^{20}$, —$NR^{21}C(O)OR^{20}$, —$NR^{21}C(O)NR^{20}R^{21}$ or —$NR^{21}C(NR^{21})NR^{20}R^{21}$, wherein $R^{12}$ and $R^{13}$ are as defined above, $R^{20}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl $(C_{9-12})$bicycloaryl$(C_{0-6})$alkyl or hetero$(C_{8-12})$bicycloaryl$(C_{0-6})$alkyl and $R^{21}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$ alkyl, hetero$(C_{5-12})$aryl$(C_{0-6})$alkyl, $(C_{9-12})$ bicycloaryl$(C_{0-6})$alkyl or hetero$(C_{8-12})$bicycloaryl $(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl wherein said cycloalkyl, heterocycloalkyl, phenyl or heteroaryl is substituted by $X^4OR^{22}$, —$X^4SR^{22}$, —$X^4S(O)R^{22}$, —$X^4S(O)_2R^{22}$, —$X^4C(O)R^{22}$, —$X^4(O)OR^{22}$, —$X^4C(O)NR^{22}R^{23}$, —$X^4NR^{22}R^{23}$, —$X^4NR^{23}C(O)R^{22}$, $X^4NR^{23}C(O)OR^{22}$, —$X^4NR^{23}C(O)NR^{22}R^{23}$ or —$X^4NR^{23}C(NR^{23})NR^{22}R^{23}$, wherein $X^4$ is as defined above $R^{22}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{12}R^{12}$, —$X^4NR^{12}C(O)OR^{12}$, —$X^4NR^{12}C(O)NR^{12}R^{12}$, —$X^4NR^{12}C(NR^{12})NR^{12}R^{12}$, —$X^4OR^{12}$, —$X^4SR^{12}$, —$X^4C(O)OR^{12}$, —$X^4C(O)NR^{12}R^{12}$, —$X^4S(O)_2NR^{12}R^{12}$, —$X^4P(O)(OR^3)OR^{12}$, —$X^4OP(O)(OR^3)OR^{12}$, —$X^4OC(O)R^{13}$, —$X^4NR^{12}C(O)R^{13}$, —$X^4S(O)R^{13}$, —$X^4S(O)_2R^{13}$, and —$X^4C(O)R^{13}$, wherein $X^4$, $R^{12}$ and $R^{13}$ are as defined above;

$R^2$ is hydrogen or $(C_{1-6})$alkyl or as defined below;

$R^3$ is hydrogen, $(C_{1-6})$alkyl or as defined below; and $R^4$ is (i) hydrogen or $(C_{1-6})$alkyl, wherein said alkyl is optionally substituted with cyano, halo nitro —$NR^{12}R^{12}$, —$NR^{12}C(O)R^{12}$, —$NR^{12}C(O)NR^{12}R^{12}$, —$NR^{12}C(NR^{12})NR^{12}R^{12}$, —$OR^{12}$, —$SR^{12}$, —$C(O)OR^{12}$, —$C(O)NR^{12}R^{12}$, —$S(O)_2NR^{12}R^{12}$, —$P(O)(OR^{12})OR^{12}$, —$OP(O)(OR^{12})OR^{12}$, —$NR^{12}C(O)R^{13}$, —$S(O)R^{13}$, —$S(O)_2R^{13}$, —$C(O)R^{13}$, —$OR^{14}$, —$SR^{14}$, —$S(O)R^{14}$, —$S(O)_2R^{14}$, —$C(O)R^{14}$, —$C(O)OR^{14}$, —$OC(O)R^{14}$, —$NR^{14}R^{15}$, —$NR^{15}C(O)R^{14}$, —$NR^{15}C(O)OR^{14}$, —$C(O)NR^{14}R^{15}$, —$S(O)_2NR^{14}R^{15}$, —$NR^{15}C(O)NR^{14}R^{15}$ or —$NR^{15}C(NR^{15})NR^{14}R^{15}$, wherein $R^{12}$, $R^{13}$, $R^{14}$ and $R^{15}$ are as defined above, or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{16}$, —$X^4OR^{16}$, —$X^4SR^{16}$, —$X^4S(O)R^{16}$, —$X^4S(O)_2R^{16}$, —$X^4C(O)R^{16}$, —$X^4C(O)OR^{16}$, —$X^4OC(O)R^{16}$, —$X^4NR^{16}R^{17}$, —$X^4NR^{17}C(O)R^6$, —$X^4NR^{17}C(O)OR^{16}$, —$X^4C(O)NR^{16}R^{17}$, —$X^4S(O)_2NR^{16}R^{17}$, —$X^4NR^{17}C(O)NR^{16}R^{17}$ or —$X^4NR^{17}C(NR^{17})NR^{16}R^{17}$, wherein $X^4$, $R^{16}$ and $R^{17}$ are as defined above; wherein within $R^9$ and/or $R^{10}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $X^4NR^{12}R^{12}$, —$X^4NR^{12}C(O)OR^{12}$, —$X^4NR^{12}C(O)NR^{12}R^{12}$, —$X^4NR^{12}C(NR^{12})NR^{12}R^{12}$, —$X^4OR^{12}$, —$X^4SR^{12}$, —$X^4C(O)OR^{12}$, —$X^4C(O)NR^{12}R^{12}$, —$X^4S(O)_2NR^{12}R^{12}$, —$X^4P(O)(OR^3)OR^{12}$, —$X^4OP(O)(OR^3)OR^{12}$, —$X^4OC(O)R^{13}$, —$X^4NR^{12}C(O)R^{13}$, —$X^4S(O)R^{13}$, —$X^4S(O)_2R^{13}$ and —$X^4C(O)R^{13}$, wherein $X^4$, $R^{12}$ and $R^{13}$ are as defined above, or $R^4$ and $R^2$ taken together form trimethylene, tetramethylene or phenylene-1,2-dimethylene, optionally substituted with hydroxy, oxo or methylene, or $R^4$ and $R^3$ together with the carbon atom to which both $R^4$ and $R^3$ are attached form $(C_{3-8})$cycloalkylene or $(C_{3-8})$heterocycloalkylene; or an N-oxide derivative, prodrug derivative, individual isomer and mixtures of isomers; or a pharmaceutically acceptable salt thereof, but excluding compounds of the formula

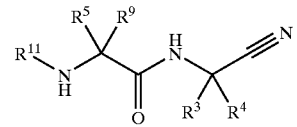

in which $R^3$ and $R^4$ are each hydrogen or $(C_{1-6})$alkyl, or together with the carbon atom to which they are both attached form $(C_{3-5})$cycloalkylene; $R^5$ is hydrogen or $(C_{1-6})$alkyl; $R^9$ is $(C_{6-12})$aryl$(C_{1-6})$alkyl, hetero$(C_{5-12})$aryl$(C_{1-6})$alkyl, $(C_{4-5})$alkyl or cyclohexylmethyl; and $R^{11}$ is $C(O)R^{18}$ wherein $R^{18}$ is hetero$(C_{3-12})$cycloalkyl, $C_{6-12}$)aryl$(C_{0-6})$alkyl or hetero$(C_{5-12})$aryl$(C_{0-6})$alkyl.

In another particular embodiment, the present invention relates to the use of a compound of Formula (I):

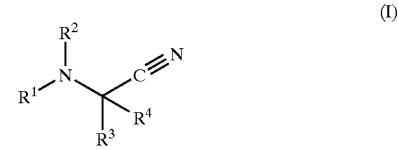

(I)

in which:

$R^1$ is a group of Formula (a) or (b):

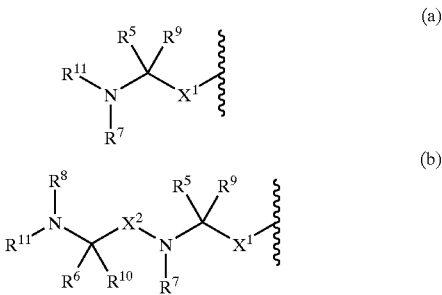

wherein:

$X^1$ and $X^2$ independently are —$C(O)$— or —$CH_2S(O)_2$—;

$R^5$ and $R^6$ are hydrogen or $(C_{1-6})$alkyl;

$R^7$ and $R^8$ are hydrogen or $(C_{1-6})$alkyl or as defined below;

$R^9$ and $R^{10}$ independently are (i) $(C_{1-6})$alkyl optionally substituted with cyano, halo or nitro or (ii) a group selected from $-X^3NR^{12}R^{12}$, $-X^3NR^{12}C(O)OR^{12}$, $-X^3NR^{12}C(O)NR^{12}R^{12}$, $-X^3NR^{12}C(NR^{12})NR^{12}R^{12}$, $-X^3OR^{12}$, $-X^3SR^{12}$, $-X^3C(O)OR^{12}$, $-X^3C(O)NR^{12}R^{12}$, $-X^3S(O)_2NR^{12}R^{12}$, $-X^3P(O)(OR^{12})OR^{12}$, $-X^3OP(O)(OR^{12})OR^{12}$, $-X^3NR^{12}C(O)R^{13}$, $-X^3S(O)R^{13}$, $-X^3S(O)_2R^{13}$, $-C(O)R^{13}$, $-X^3C(O)R^{14}$, $-X^3C(O)OR^{14}$, $-X^3OC(O)R^{14}$, $-X^3NR^{15}C(O)R^{14}$, $-X^3NR^{15}C(O)OR^{14}$, $-X^3C(O)NR^{14}R^{15}$, $-X^3S(O)_2NR^{14}R^{15}$, $-X^3NR^{15}C(O)NR^{14}R^{15}$, $-X^3NR^{15}C(NR^{15})NR^{14}R^{15}$, $-X^4SR^{14}$, $-X^4S(O)R^{14}$, $-X^4S(O)_2R^{14}$, $-X^4OR^{14}$, or $-X^4NR^{14}R^{15}$, wherein $X^3$ is $(C_{1-6})$alkylene, $X^4$ is a bond or $(C_{1-6})$alkylene, $R^{12}$ at each occurrence independently is hydrogen, $(C_{1-6})$alkyl or halo-substituted $(C_{1-3})$alkyl, $R^{13}$ is $(C_{1-6})$alkyl or halo-substituted $(C_{1-3})$alkyl, $R^{14}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkly $(C_{9-12})$polycycloaryl$(C_{0-6})$alkyl or hetero$(C_{8-12})$polycycloaryl$(C_{0-6})$alkyl and $R^{15}$ is hydrogen or $(C_{1-6})$alkyl, and wherein within $R^{14}$ said cycloalkyl, heterocycloalkyl, aryl, heteroaryl, polycycloaryl or heterpolycycloaryl ring optionally is substituted by a group selected from $-R^{16}$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-X^4NR^{17}C(O)OR^{16}$, $-X^4C(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$ is a bond or $(C_{1-6})$alkylene, $R^{16}$ is hydrogen or $(C_{1-6})$alkyl and $R^{17}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl hetero$(C_{8-12})$polycycloaryl$(C_{0-6})$alkyl, or (iii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^{16}$, $-X^4OR^{16}$, $-X^4SR^{16}$, $-X^4S(O)R^{16}$, $-X^4S(O)_2R^{16}$, $-X^4C(O)R^{16}$, $-X^4C(O)OR^{16}$, $-X^4OC(O)R^{16}$, $-X^4NR^{16}R^{17}$, $-X^4NR^{17}C(O)R^{16}$, $-XNR^{17}C(O)OR^{16}$, $-X^4C(O)NR^{16}R^{17}$, $-X^4S(O)_2NR^{16}R^{17}$, $-X^4NR^{17}C(O)NR^{16}R^{17}$ or $-X^4NR^{17}C(NR^{17})NR^{16}R^{17}$, wherein $X^4$, $R^{16}$ and $R^{17}$ are as defined above; wherein within $R^9$ and/or $R^{10}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^4)OR^{12}$, $-X^4OP(O)(OR^{12})OR^{12}$, $-X^4OC(O)R^3$, $-X^4NR^{12}C(O)R^{13}$, $-X^4S(O)R^{13}$, $-X^4S(O)_2R^{13}$ and $-X^4C(O)R^{13}$, wherein $X^4$, $R^{12}$ and $R^{13}$ are as defined above, or $R^9$ taken together with $R^7$ and/or $R^{10}$ taken together with $R^8$ form trimethylene, tetramethylene or phenylene-1,2-dimethylene, optionally substituted with hydroxy, oxo or methylene; and $R^{11}$ is $-X^5X^6R^{18}$, wherein $X^5$ is $-C(O)-$, $-C(O)C(O)-$ or $-S(O)_2-$, $X^6$ is a bond, $-O-$ or $-NR^{19}-$, wherein $R^{19}$ is hydrogen or $(C_{1-6})$alkyl, and $R^{18}$ is (i) $(C_{1-10})$alkyl optionally substituted by cyano, halo, nitro, $-NR^{12}R^{12}$, $-NR^{12}C(O)R^{12}$, $-NR^{12}C(O)NR^{12}R^{12}$, $-NR^{12}C(NR^{12})NR^{12}R^{12}$, $OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{20}$, $-SR^{20}$, $-S(O)R^{20}$, $-S(O)_2R^{20}$, $-C(O)R^{20}$, $-C(O)OR^{20}$, $-C(O)NR^{20}R^{21}$, $-NR^{20}R^{21}$, $-NR^{21}C(O)R^{20}$, $-NR^{21}C(O)OR^{20}$, $-NR^{12}C(O)NR^{20}R^{21}$ or $-NR^{21}C(NR^{21})NR^{20}R^{21}$, wherein $R^{12}$ and $R^{13}$ are as defined above, $R^{20}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkly $(C_{9-12})$bicycloaryl$(C_{0-6})$alkyl or hetero$(C_{8-12})$bicycloaryl$(C_{0-6})$alkyl and $R^{21}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl $(C_{0-6})$ or hetero$(C_{8-12})$bicycloaryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkly wherein said cycloalkyl, heterocycloalkyl, phenyl or heteroaryl is substituted by $-X^4OR^{22}$, $-X^4SR^{22}$, $-X^4S(O)R^{22}$, $-X^4S(O)_2R^{22}$, $-X^4C(O)R^{22}$, $-X^4C(O)OR^{22}$, $-X^4C(O)NR^{22}R^{23}$, $-X^4NR^{22}R^{23}$, $-X^4NR^{23}C(O)R^{22}$, $-X^4NR^{23}C(O)OR^{22}$, $-X^4NR^{23}C(O)NR^{22}R^{23}$ or $-X^4NR^{23}C(NR^{23})NR^{22}R^{23}$, wherein $X^4$ is as defined above $R^{22}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{23}$ at each occurrence independently is hydrogen or $(C_{1-6})$alkyl; wherein within $R^{11}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^4NR^{12}R^{12}$, $-X^4NR^{12}C(O)OR^{12}$, $-X^4NR^{12}C(O)NR^{12}R^{12}$, $-X^4NR^{12}C(NR^{12})NR^{12}R^{12}$, $-X^4OR^{12}$, $-X^4SR^{12}$, $-X^4C(O)OR^{12}$, $-X^4C(O)NR^{12}R^{12}$, $-X^4S(O)_2NR^{12}R^{12}$, $-X^4P(O)(OR^3)OR^{12}$, $-X^4OP(O)(OR^3)OR^{12}$, $-X^4OC(O)R^{13}$, $-X^4NR^{12}C(O)R^{13}$, $-X^4S(O)R^{13}$, $-X^4S(O)_2R^{13}$ and $-X^4C(O)R^{13}$, wherein $X^4$, $R^{12}$ and $R^{13}$ are as defined above;

$R^2$ is hydrogen or $(C_{1-6})$alkyl or as defined below;

$R^3$ is hydrogen, $(C_{1-6})$alkyl or as defined below; and $R^4$ is(i) hydrogen or $(C_{1-6})$alkyl, wherein said alkyl is optionally substituted with cyano, halo, nitro, $-NR^{12}R^{12}$, $-NR^{12}C(O)OR^{12}$, $-NR^{12}C(O)NR^{12}R^{12}$, $-NR^{12}C(NR^{12})NR^{12}R^{12}$, $-OR^{12}$, $-SR^{12}$, $-C(O)OR^{12}$, $-C(O)NR^{12}R^{12}$, $-S(O)_2NR^{12}R^{12}$, $-P(O)(OR^{12})OR^{12}$, $-OP(O)(OR^{12})OR^{12}$, $-NR^{12}C(O)R^{13}$, $-S(O)R^{13}$, $-S(O)_2R^{13}$, $-C(O)R^{13}$, $-OR^{14}$, $-SR^{14}$, $-S(O)R^{14}$, $-S(O)_2R^{14}$, $-C(O)R^{14}$, $-C(O)OR^{14}$, $-OC(O)R^{14}$, $-NR^{14}R^{15}$, $-NR^{15}C(O)R^{14}$, $-NR^{15}C(O)OR^{14}$, $-C(O)NR^{14}R^{15}$, $-S(O)_2NR^{14}R^{15}$, $-NR^{15}C(O)NR^{14}R^{15}$ or $-NR^{15}C(NR^{15})NR^{14}R^{15}$, wherein $R^{12}$, $R^{13}$, $R^{14}$ and $R^{15}$ are as defined above, or (ii) a group selected from $(C_{3-12})$cycloalkyl$(C_{0-6})$alkyl, hetero$(C_{3-12})$cycloalkyl$(C_{0-6})$ alkyl, $(C_{6-12})$aryl$(C_{0-6})$alkyl, hetero$(C_{5-12})$aryl$(C_{0-6})$ alkyl, $(C_{9-12})$polycycloaryl$(C_{0-6})$alkyl and hetero $(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{16}$, —$X^4OR^{16}$, —$X^4SR^{16}$, —$X^4S(O)R^{16}$, —$X^4S(O)_2R^{16}$, —$X^4C(O)R^{16}$, —$X^4C(O)OR^{16}$, $X^4OC(O)R^{16}$, —$X^4NR^{16}R^{17}$, —$X^4NR^{17}C(O)R^{16}$, —$X^4NR^{17}C(O)OR^{16}$, —$X^4C(O)NR^{16}R^{17}$, —$X^4S(O)_2NR^{16}R^{17}$, —$X^4NR^{17}C(O)NR^{16}R^{17}$ or —$X^4NR^{17}C(NR^{17})NR^{16}R^{17}$, wherein $X^4$, $R^{16}$ and $R^{17}$ are as defined above; wherein within $R^9$ and/or $R^{10}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{12}R^{12}$, —$X^4NR^{12}C(O)R^{12}$, —$X^4NR^{12}C(O)NR^{12}R^{12}$, —$X^4NR^{12}C(NR^{12})NR^{12}R^{12}$, —$X^4OR^{12}$, —$X^4SR^{12}$, —$X^4C(O)OR^{12}$, —$X^4C(O)NR^{12}R^{12}$, —$X^4S(O)_2NR^{12}R^{12}$, —$X^4P(O)(OR^3)OR^{12}$, —$X^4OP(O)(OR^3)OR^{12}$, —$X^4OC(O)R^{13}$, —$X^4NR^{12}C(O)R^{13}$, —$X^4S(O)R^{13}$, —$X^4S(O)_2R^{13}$ and —$X^4C(O)R^{13}$, wherein $X^4$, $R^{12}$ and $R^{13}$ are as defined above, or $R^4$ and $R^2$ taken together form trimethylene, tetramethylene or phenylene-1,2-dimethylene, optionally substituted with hydroxy, oxo or methylene, or $R^4$ and $R^3$ together with the carbon atom to which both $R^4$ and $R^3$ are attached form $(C_{3-8})$cycloalkylene or $(C_{3-8})$heterocycloalkylene; or an N-oxide derivative, prodrug derivative, individual isomer and mixtures of isomers; or a pharmaceutically acceptable salt thereof, but excluding compounds of the formula

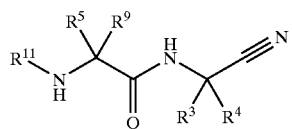

in which $R^3$ and $R^4$ are each hydrogen or $(C_{1-6})$alkyl, or together with the carbon atom to which they are both attached form $(C_{3-5})$cycloalkylene; $R^5$ is hydrogen or $(C_{1-6})$alkyl; $R^9$ is $(C_{6-12})$aryl$(C_{1-6})$alkyl, hetero$(C_{5-12})$aryl$(C_{1-6})$alkyl, $(C_{4-5})$alkyl or cyclohexylmethyl; and $R^{11}$ is $C(O)R^{18}$ wherein $R^{18}$ is hetero$(C_{3-12})$cycloalkyl, $(C_{6-12})$aryl$(C_{0-6})$alkyl or hetero$(C_{5-12})$aryl $(C_{0-6})$alkyl, in the manufacture of a medicament for treating a disease in an animal in which cathepsin S activity contributes to the pathology and/or symptomatology of the disease.

In another particular embodiment, the present invention relates to a method of treating a disease in an animal in which cathepsin S activity contributes to the pathology and/or symptomatology of the disease, which method comprising administering to the animal a therapeutically effective amount of a compound of Formula (III):

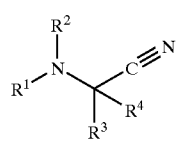

(III)

in which:
$R^1$ is a group of Formula (a) or (b):

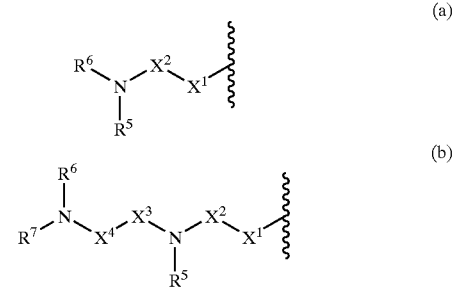

wherein:
$X^1$ and $X^3$ independently are —C(O)— or —S(O)$_2$—,
$X^2$ is —CR$^8$R$^9$—, —CH$_2$CR$^8$R$^9$— or —CR$^8$R$^9$CH$_2$— and $X^4$ is —CHR$^{10}$—, —CH$_2$CHR$^{10}$— or —CHR$^{10}$CH$_2$—, wherein:
$R^8$ is hydrogen or $(C_{1-6})$alkyl,
$R^9$ is (i) $(C_{1-6})$alkyl or halo-substituted$(C_{1-6})$alkyl optionally substituted with —OR$^{11}$, —SR$^{11}$, —S(O)R$^{11}$, —S(O)$_2$R$^{11}$, —C(O)R$^{11}$, —C(O)OR$^{11}$, —NR$^{11}$R$^{12}$, —NR$^{12}$C(O)OR$^{11}$, —C(O)NR$^{11}$R$^{12}$, —S(O)$_2$NR$^{11}$R$^{12}$, —NR$^{12}$C(O)NR$^{11}$R$^{12}$ or —NR$^{12}$C(NR$^{12}$)NR$^{11}$R$^{12}$, wherein $R^{11}$ is hydrogen, $(C_{1-6})$alkyl, $(C_{3-12})$cycloalkyl$(C_{0-3})$alkyl, hetero$(C_{3-12})$cycloalkyl$(C_{0-3})$alkyl, $(C_{6-12})$aryl$(C_{0-3})$alkyl or hetero$(C_{5-12})$aryl$(C_{0-3})$alkyl and $R^{12}$ is hydrogen or $(C_{1-6})$alkyl, or (ii) $(C_{3-12})$cycloalkyl$(C_{0-3})$alkyl, hetero$(C_{3-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl $(C_{0-3})$alkyl or hetero$(C_{8-12})$polycycloaryl$(C_{0-3})$alkyl optionally substituted with —R$^{13}$, —X$^5$OR$^3$, —X$^5$SR$^{13}$, —S(O)R$^{13}$, —S(O)$_2$R$^{13}$, —C(O)R$^{13}$, —C(O)OR$^{13}$, —X$^5$NR$^{13}$R$^{14}$, —X$^5$NR$^{14}$C(O) OR$^{13}$, —C(O)NR$^{13}$R$^{14}$, —S(O)$_2$NR$^{13}$R$^{14}$, —NR$^{14}$C(O)NR$^{13}$R$^{14}$ or —NR$^{14}$C(NR$^{14}$) NR$^{13}$R$^{14}$, wherein $X^5$ is a bond or methylene, $R^{13}$ is $(C_{3-12})$cycloalkyl$(C_{0-3})$alkyl, hetero$(C_{3-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl$(C_{0-3})$alkyl or hetero$(C_{8-12})$polycycloaryl$(C_{0-3})$alkyl and $R^{14}$ is hydrogen or $(C_{1-6})$alkyl, or (iii) together with $R^5$ when $X^2$ is —CHR$^9$— forms trimethylene, tetramethylene or phenylene-1,2-dimethylene, optionally substituted with 1 to 2 of hydroxy, oxo, $(C_{1-4})$alkyl or methylene; wherein any 1 to 3 annular atoms of any aromatic ring with available valences comprising $R^9$ are optionally independently substituted with halo, nitro, cyano, $(C_{1-6})$alkyl, halo-substituted$(C_{1-6})$alkyl, —OR$^{15}$, —C(O)R$^{15}$, —C(O)OR$^5$, —C(O)NR$^{15}$R$^{15}$, —S(O)$_2$NR$^{15}$R$^{15}$, —X$^5$NR$^{15}$R$^{15}$, —X$^5$NR$^{15}$C(O) OR$^{15}$, —X$^5$NR$^{15}$C(O)NR$^{15}$R$^{15}$ or —X$^5$NR$^{15}$C (NR$^{15}$NR$^{15}$R$^{15}$, wherein $X^5$ is as defined above and each $R^{15}$ independently is hydrogen or $(C_{1-6})$alkyl, and
$R^{10}$ is hydrogen or $(C_{1-4})$alkyl;
$R^5$ and $R^7$ are independently hydrogen, $(C_{1-6})$alkyl or as defined above; and
$R^6$ is —X$^6$X$^7$R$^{16}$, wherein $X^6$ is —C(O)— or —S(O)$_2$—, $X^7$ is a bond, —O— or —NR$^{17}$—, wherein $R^{17}$ is hydrogen or $(C_{1-6})$alkyl, and $R^{16}$ is (i) $(C_{1-6})$alkyl or halo-substituted$(C_{1-6})$alkyl optionally substituted with —OR$^{11}$, —SR$^{11}$, —S(O)R$^{11}$, —S(O)$_2$R$^{11}$, —C(O)R$^{11}$, —C(O)OR$^{11}$, —NR$^{11}$R$^{12}$, —NR$^{12}$C(O)OR$^{11}$, —C(O)NR$^{11}$R$^{12}$, —NR$^{12}$C(O)NR$^{11}$R$^{12}$ or —NR$^{12}$C(NR$^{12}$)NR$^{11}$R$^{12}$, wherein R$^{11}$ and R$^{12}$ are as defined above, or (ii) (C$_{3-6}$)cycloalkyl (C$_{0-3}$)alkyl, hetero(C$_{3-6}$)cycloalkyl(C$_{0-3}$)alkyl, (C$_{6-12}$)aryl(C$_{0-3}$)alkyl, hetero(C$_{5-12}$)aryl(C$_{0-3}$)alkyl, ( C$_{9-12}$)polycycloaryl(C$_{0-3}$)alkyl or hetero(C$_{8-12}$)polycycloaryl(C$_{0-3}$)alkyl optionally substituted with 1 to 2 of —R$^{13}$, —X$^5$OR$^{13}$, —X$^5$SR$^{13}$, —S(O)R$^{13}$, —S(O)$_2$R$^{13}$, —C(O)OR$^{13}$, —X$^5$NR$^{13}$R$^{14}$, —X$^5$NR$^{14}$C(O)OR$^{13}$, —C(O)NR$^{13}$R$^{14}$, —NR$^{14}$C(O)NR$^{13}$R$^{14}$ or —NR$^{14}$C(NR$^{14}$)NR$^{13}$R$^{14}$, wherein X$^5$, R$^{13}$ and R$^{14}$ are as defined above; wherein any 1 to 3 annular atoms of any aromatic ring with available valences comprising R$^{16}$ optionally independently are substituted with halo, nitro, cyano, (C$_{1-6}$)alkyl, halo-substituted(C$_{1-6}$)alkyl, —OR$^{15}$, —C(O)R$^{15}$, —C(O)OR$^{15}$, —C(O)NR$^{15}$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$)NR$^{15}$R$^{15}$, wherein X$^5$ and R$^{15}$ are as defined above;

R$^2$ is hydrogen or (C$_{1-6}$)alkyl or as defined below;

R$^3$ is hydrogen, (C$_{1-10}$)alkyl or as defined below; and

R$^4$ is (i) hydrogen, (ii) (C$_{1-6}$)alkyl or halo-substituted(C$_{1-6}$)alkyl optionally substituted with —OR$^{11}$, —SR$^{11}$, —S(O)R$^{11}$, —S(O)$_2$R$^{11}$, —C(O)R$^{11}$, —C(O)OR$^{11}$, —NR$^{11}$R$^{12}$, —NR$^{12}$C(O)OR$^{11}$, —C(O)NR$^{11}$R$^{12}$, —NR$^{12}$C(O)NR$^{11}$R$^{12}$ or —NR$^{12}$C(NR$^{12}$)NR$^{11}$R$^{12}$, wherein R$^{11}$ and R$^{12}$ are as defined above, or (iii) (C$_{3-12}$)cycloalkyl(C$_{0-3}$)alkyl, hetero(C$_{3-12}$)cycloalkyl (C$_{0-3}$)alkyl, (C$_{6-12}$)aryl(C$_{0-3}$)alkyl, hetero(C$_{5-12}$)aryl (C$_{0-3}$)alkyl, (C$_{9-12}$)polycycloaryl(C$_{0-3}$)alkyl or hetero (C$_{8-12}$)polycycloaryl(C$_{0-3}$)alkyl optionally substituted with —R$^{13}$, —X$^5$OR$^{13}$, —X$^5$SR$^{13}$, —S(O)R$^{13}$, —S(O)$_2$R$^{13}$, —C(O)OR$^{13}$, —X$^5$NR$^{13}$R$^{14}$, —X$^5$NR$^{14}$C(O)OR$^{13}$, —C(O)NR$^{13}$R$^{14}$, —NR$^{14}$C(O)NR$^{13}$R$^{14}$ or —NR$^{14}$C(NR$^{14}$)NR$^{13}$R$^{14}$, wherein X$^5$, R$^{13}$ and R$^{14}$ are as defined above or (iv) together with R$^2$ forms trimethylene, tetramethylene or phenylene-1,2-dimethylene, optionally substituted with hydroxy, oxo, (C$_{1-4}$)alkyl or methylene or (v) together with R$^3$ forms ethylene, trimethylene or tetramethylene; wherein any 1 to 3 annular atoms of any aromatic ring with available valences comprising R$^4$ optionally independently are substituted with halo, nitro, cyano, (C$_{1-6}$)alkyl, halo-substituted(C$_{1-6}$)alkyl, —OR$^5$, —C(O)R$^{15}$, —C(O)OR$^{15}$, —C(O)NR$^5$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$)NR$^{15}$R$^{15}$, wherein X$^5$ and R$^{15}$ are as defined above; or an N-oxide derivative, prodrug derivative, individual isomer and mixtures of isomers; or a pharmaceutically acceptable salt thereof, but excluding compounds of the formula

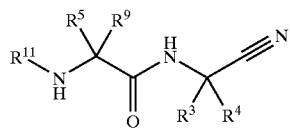

in which R$^3$ and R$^4$ are each hydrogen or (C$_{1-6}$)alkyl, or together with the carbon atom to which they are both attached form (C$_{3-5}$)cycloalkylene; R$^5$ is hydrogen or (C$_{1-6}$)alkyl; R$^9$ is (C$_{6-12}$)aryl(C$_{1-6}$)alkyl, hetero(C$_{5-12}$) aryl(C$_{1-6}$)alkyl, (C$_{4-5}$)alkyl or cyclohexylmethyl; and R$^{11}$ is C(O)R$^{18}$ wherein R$^{18}$ is hetero(C$_{3-12}$)cycloalkyl, (C$_{6-12}$)aryl(C$_{0-6}$)alkyl or hetero(C$_{5-12}$)aryl($_{0-6}$)alkyl.

In another particular embodiment, the present invention relates to the use of a compound of Formula (III):

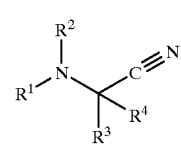

(III)

in which:

R$^1$ is a group of Formula (a) or (b):

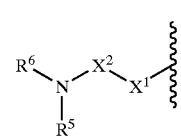

(a)

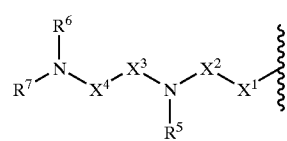

(b)

wherein:

X$^1$ and X$^3$ independently are —C(O)— or —S(O)$_2$—,
X$^2$ is —CR$^8$R$^9$—, —CH$_2$CR$^8$R$^9$— or —CR$^8$R$^9$CH$_2$— and X$^4$ is —CHR$^{10}$—, —CH$_2$CHR$^{10}$— or —CHR$^{10}$CH$_2$—, wherein:

R$^8$ is hydrogen or (C$_{1-6}$)alkyl,

R$^9$ is (i) (C$_{1-6}$)alkyl or halo-substituted(C$_{1-6}$)alkyl optionally substituted with —OR$^{11}$, —SR$^{11}$, —S(O)R$^{11}$, —S(O)$_2$R$^{11}$, —C(O)R$^{11}$, —C(O) OR$^{11}$, —NR$^{11}$R$^{12}$, —NR$^{12}$C(O)OR$^{11}$, —C(O) NR$^{11}$R$^{12}$, —S(O)$_2$NR$^{11}$R$^{12}$, —NR$^{12}$C(O) NR$^{11}$R$^{12}$ or —NR$^{12}$C(NR$^{12}$)NR$^{11}$R$^{12}$, wherein R$^{11}$ is hydrogen, (C$_{1-6}$)alkyl, (C$_{3-12}$)cycloalkyl (C$_{0-3}$)alkyl, hetero(C$_{3-12}$)cycloalkyl(C$_{0-3}$)alkyl, (C$_{6-12}$)aryl(C$_{0-3}$)alkyl or hetero(C$_{5-12}$)aryl(C$_{0-3}$) alkyl and R$^{12}$ is hydrogen or (C$_{1-6}$)alkyl, or (ii) (C$_{3-12}$)cycloalkyl(C$_{0-3}$)alkyl, hetero(C$_{3-12}$) cycloalkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)polycycloaryl (C$_{0-3}$)alkyl or hetero(C$_{8-12}$)polycycloaryl(C$_{0-3}$) alkyl optionally substituted with —R$^{13}$, —X$^5$OR$^{13}$, —X$^5$SR$^{13}$, —S(O)R$^{13}$, —S(O)$_2$R$^{13}$, —C(O)R$^{13}$, —C(O)OR$^{13}$, —X$^5$NR$^{13}$R$^{14}$, —X$^5$NR$^{14}$C(O)OR$^{13}$, —C(O)NR$^{13}$R$^{14}$, —S(O)$_2$NR$^{13}$R$^{14}$, —NR$^{14}$C(O)NR$^{13}$R$^{14}$ or —NR$^{14}$C(NR$^{14}$)NR$^{13}$R$^{14}$, wherein X$^5$ is a bond or methylene, R$^{13}$ is (C$_{3-12}$)cycloalkyl(C$_{0-3}$)alkyl, hetero(C$_{3-12}$)cycloalkyl(C$_{0-3}$)alkyl, (C$_{6-12}$)aryl (C$_{0-3}$)alkyl, hetero(C$_{5-12}$)aryl(C$_{0-3}$)alkyl, (C$_{9-12}$) polycycloaryl(C$_{0-3}$)alkyl or hetero(C$_{8-12}$) polycycloaryl(C$_{0-3}$)alkyl and R$^{14}$ is hydrogen or (C$_{1-6}$)alkyl, or (iii) together with R$^5$ when X$^2$ is —CHR$^9$— forms trimethylene, tetramethylene or phenylene-1,2-dimethylene, optionally substituted with 1 to 2 of hydroxy, oxo, (C$_{1-4}$)alkyl or methylene; wherein any 1 to 3 annular atoms of any aromatic ring with available valences comprising R$^9$ are optionally independently substituted with halo, nitro, cyano, $(C_{1-6})$alkyl, halo-substituted$(C_{1-6})$alkyl, —OR$^{15}$, —C(O)R$^{15}$, —C(O)OR$^{15}$, —C(O)NR$^{15}$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$NR$^{15}$R$^{15}$, wherein X$^5$ is as defined above and each R$^{15}$ independently is hydrogen or $(C_{1-6})$alkyl, and R$^{10}$ is hydrogen or $(C_{1-4})$alkyl;

R$^5$ and R$^7$ are independently hydrogen, $(C_{1-6})$alkyl or as defined above; and R$^6$ is —X$^6$X$^7$R$^{16}$, wherein X$^6$ is —C(O)— or —S(O)$_2$—, X$^7$ is a bond, —O— or —NR$^{17}$—, wherein R$^{17}$ is hydrogen or $(C_{1-6})$alkyl, and R$^{16}$ is (i) $(C_{1-6})$alkyl or halo-substituted$(C_{1-6})$alkyl optionally substituted with —OR$^{11}$, —SR$^{11}$, —S(O)R$^{11}$, —S(O)$_2$R$^{11}$, —C(O)R$^{11}$, —C(O)OR$^{11}$, —NR$^{11}$R$^{12}$, —NR$^{12}$C(O)OR$^{11}$, —C(O)NR$^{11}$R$^{12}$, —NR$^{12}$C(O)NR$^{11}$R$^{12}$ or —NR$^{12}$C(NR$^{12}$)NR$^{11}$R$^{12}$, wherein R$^{11}$ and R$^{12}$ are as defined above, or (ii) $(C_{3-6})$cycloalkyl$(C_{0-3})$alkyl, hetero$(C_{3-6})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl$(C_{0-3})$alkyl or hetero$(C_{8-12})$polycycloaryl$(C_{0-3})$alkyl optionally substituted with 1 to 2 of —R$^{13}$, —X$^5$OR$^{13}$, —X$^5$SR$^{13}$, —S(O)R$^{13}$, —S(O)$_2$R$^{13}$, —C(O)OR$^{13}$, —X$^5$NR$^{13}$R$^{14}$, —X$^5$NR$^{14}$C(O)OR$^{13}$, —C(O)NR$^{13}$R$^{14}$, —NR$^{14}$C(O)NR$^{13}$R$^{14}$ or —NR$^{14}$C(NR$^{14}$)NR$^{13}$R$^{14}$, wherein X$^5$, R$^{13}$ and R$^{14}$ are as defined above; wherein any 1 to 3 annular atoms of any aromatic ring with available valences comprising R$^{16}$ optionally independently are substituted with halo, nitro, cyano, $(C_{1-6})$alkyl, halo-substituted$(C_{1-6})$alkyl, —OR$^{15}$, —C(O)R$^{15}$, —C(O)OR$^{15}$, —C(O)NR$^{15}$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$)NR$^{15}$R$^{15}$, wherein X$^5$ and R$^{15}$ are as defined above;

R$^2$ is hydrogen or $(C_{1-6})$alkyl or as defined below;

R$^3$ is hydrogen, $(C_{1-10})$alkyl or as defined below; and

R$^4$ is (i) hydrogen, (ii) $(C_{1-6})$alkyl or halo-substituted $(C_{1-6})$alkyl optionally substituted with —OR$^{11}$, —SR$^{11}$, —S(O)R$^{11}$, —S(O)$_2$R$^{11}$, —C(O)R$^{11}$, —C(O)OR$^{11}$, —NR$^{11}$R$^{12}$, —NR$^{12}$C(O)OR$^{11}$, —C(O)NR$^{11}$R$^{12}$, —NR$^{12}$C(O)NR$^{11}$R$^{12}$ or —NR$^{12}$C(NR$^{12}$)NR$^{11}$R$^{12}$, wherein R$^{11}$ and R$^{12}$ are as defined above, or (iii) $(C_{3-12})$cycloalkyl$(C_{0-3})$alkyl, hetero$(C_{3-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$polycycloaryl$(C_{0-3})$alkyl or hetero$(C_{8-12})$polycycloaryl$(C_{0-3})$alkyl optionally substituted with —R$^{13}$, —X$^5$OR$^{13}$, —X$^5$SR$^{13}$, —S(O)R$^{13}$, —S(O)$_2$R$^{13}$, —C(O)OR$^{13}$, —X$^5$NR$^{13}$R$^{14}$, —X$^5$NR$^{14}$C(O)R$^{13}$, —C(O)NR$^{13}$R$^{14}$, —NR$^{14}$C(O)NR$^3$R$^{14}$ or —NR$^{14}$C(NR$^{14}$)NR$^{13}$R$^{14}$, wherein X$^5$, R$^{13}$ and R$^{14}$ are as defined above or (iv) together with R$^2$ forms trimethylene, tetramethylene or phenylene-1,2-dimethylene, optionally substituted with hydroxy, oxo, $(C_{1-4})$alkyl or methylene or (v) together with R$^3$ forms ethylene, trimethylene or tetramethylene; wherein any 1 to 3 annular atoms of any aromatic ring with available valences comprising R$^4$ optionally independently are substituted with halo, nitro, cyano, $(C_{1-6})$alkyl, halo-substituted$(C_{1-6})$alkyl, —OR$^{15}$, —C(O)R$^{15}$, —C(O)OR$^{15}$, —C(O)NR$^{15}$R$^{15}$, —S(O)$_2$NR$^{15}$R$^{15}$, —X$^5$NR$^{15}$R$^{15}$, —X$^5$NR$^{15}$C(O)OR$^{15}$, —X$^5$NR$^{15}$C(O)NR$^{15}$R$^{15}$ or —X$^5$NR$^{15}$C(NR$^{15}$)NR$^{15}$R$^{15}$, wherein X$^5$ and R$^{15}$ are as defined above; or an N-oxide derivative, prodrug derivative, individual isomer and mixtures of isomers; or a pharmaceutically acceptable salt thereof, but excluding compounds of the formula

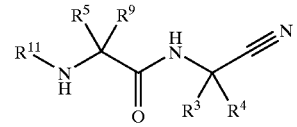

in which R$^3$ and R$^4$ are each hydrogen or $(C_{1-6})$alkyl, or together with the carbon atom to which they are both attached form $(C_{3-8})$cycloalkylene; R$^5$ is hydrogen or $(C_{1-6})$alkyl; R$^9$ is $(C_{6-12})$aryl$(C_{1-6})$alkyl, hetero$(C_{5-12})$aryl$(C_{1-6})$alkyl, $(C_{4-5})$alkyl or cyclohexylmethyl; and R$^{11}$ is C(O)R$^{18}$ wherein R$^{18}$ is hetero$(C_{3-12})$cycloalkyl, $(C_{6-12})$aryl$(C_{0-6})$alkyl or hetero$(C_{5-12})$aryl$(C_{0-6})$alkyl, in the manufacture of a medicament for treating a disease in an animal in which cathepsin S activity contributes to the pathology and/or symptomatology of the disease.

DETAILED DESCRIPTION OF THE INVENTION

Definitions

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by straight or branched chain arrangement of the constituent carbon atoms and may be saturated or partially unsaturated with two or more double or triple bonds.

"Alkyl" indicated alone means a straight or branched, saturated or unsaturated aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl indicated as part of a larger radical (e.g., as in arylalkyl) means a straight or branched, saturated or unsaturated aliphatic divalent radical having the number of atoms indicated or when 0 atoms are indicated means a bond (e.g., $(C_{0-3})$alkyl of $(C_{3-12})$cycloalkyl$(C_{0-3})$alkyl means a bond, methylene, ethylene, trimethylene, 1-methylethylene, or the like).

"Alkylene", unless indicated otherwise, means a straight or branched, saturated or unsaturated, aliphatic, divalent radical having the number of carbon atoms indicated (e.g. $(C_{1-6})$alkylene includes methylene (—CH$_2$—), ethylene (—CH$_2$CH$_2$—), trimethylene (—CH$_2$CH$_2$CH$_2$—), 2-methyltrimethylene (—CH$_2$CH(CH$_3$)CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). For example, the instance wherein R$^5$ is hydrogen and R$^9$ taken together with R$^7$ forms optionally substituted trimethylene is illustrated by the following:

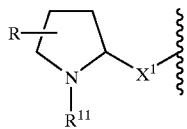

in which R is an optional hydroxy or oxo group and $X^1$ and $R^{11}$ are as defined in the Summary of the Invention.

"Alkylidene" means a straight or branched saturated or unsaturated, aliphatic, divalent radical having the number of carbon atoms indicated (e.g. $(C_{1-6})$alkylidene includes methylene ($:CH_2$), ethylidene ($CHCH_3$), isopropylidene ($C(CH_3)_2$), propylidene ($CHCH_2CH_3$), allylidene ($CHCHCH_2$), and the like).

"Amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, etc.) and non-mammals (e.g., birds, etc.).

"Aryl" means a monocyclic or bicyclic ring assembly (fused or linked by a single bond) containing the total number of ring carbon atoms indicated, wherein each ring is comprised of 6 ring carbon atoms and is aromatic or when fused with a second ring forms an aromatic ring assembly. For example, $(C_{6-12})$aryl includes phenyl, naphthyl and biphenylyl.

"Aromatic" means a moiety wherein the constituent atoms make up an unsaturated ring system, all atoms in the ring system are sp2 hybridized and the total number of pi electrons is equal to 4n+2.

"Carbamoyl" means the radical —$C(O)NH_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carboxy" means the radical —$C(O)OH$. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic ring, bicyclic ring assembly (directly linked by a single bond or fused) or bridged polycyclic ring assembly containing the number of annular carbon atoms indicated, and any carbocyclic ketone, thioketone or iminoketone derivative thereof (e.g., $(C_{3-12})$cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthalenyl, oxocyclohexyl, dioxocyclohexyl, thiocyclohexyl, 2-oxobicyclo[2.2.1]hept-1-yl, etc.).

"Cycloalkylene" means a saturated or partially unsaturated, monocyclic ring or bridged polycyclic ring assembly containing the number of annular carbon atoms indicated, and any carbocyclic ketone, thioketone or iminoketone derivative thereof. For example, the instance wherein $R^9$ and $R^5$ together with the carbon atom to which both $R^9$ and $R^5$ are attached form $(C_{3-8})$cycloalkylene" includes, but is not limited to, the following:

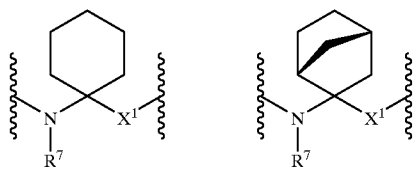

in which $X^1$ and $R^7$ are as defined in the Summary of the Invention.

"Disease" specifically includes any unhealthy condition of an animal or part thereof and includes an unhealthy condition which may be caused by, or incident to, medical or veterinary therapy applied to that animal, i.e., the "side effects" of such therapy.

"Guanidino" means the radical —$NHC(NH)NH_2$. Unless indicated otherwise, the compounds of the invention containing guanidino moieties include protected derivatives thereof. Suitable protecting groups for amino moieties include acetyl, tert-butoxycarbonyl, benzyloxycarbonyl, and the like.

"Halo" means fluoro, chloro, bromo or iodo.

"Halo-substituted alkyl", as a group or part of a group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dicloromethyl, difluoromethyl, trifluromethyl, 2,2,2-trifluoroethyl, perfluoroethyl, 2,2,2-trifluoro-1,1-dichloroethyl, and the like).

"Heteroaryl" means aryl, as defined in this Application, provided that one or more of the ring member carbon atoms indicated, is replaced by heteroatom moiety selected from —N, —NR—, —O— or —S—, wherein R is hydrogen, $(C_{1-6})$alkyl or a protecting group, and each ring contained therein is comprised of 5 to 6 ring member atoms. For example, hetero$(C_{5-12})$aryl as used in this Application includes benzofuryl, benzooxazolyl, benzothiazolyl, [2,4'] bipyridinylyl, carbazolyl, carbolinyl, chromenyl, cinnolinyl, furazanyl, furyl, imidazolyl, indazolyl, indolyl, indolizinyl, isobenzofuryl, isochromenyl, isooxazolyl, isoquinolyl, isothiazolyl, naphthyridinyl, oxazolyl, perimidinyl, 2-phenylpyridyl, phthalazinyl, pteridinyl, purinyl, pyrazinyl, pyradazinyl, pyrazolyl, pyridyl, pyrimidinyl, pyrrolizinyl, pyrrolidinyl, pyrrolyl, pyranyl, quinazolinyl, quinolizinyl, quinolyl, quinoxalinyl, tetrazolyl, thiazolyl, 4-thiazol-4-ylphenyl, thienyl, xanthenyl, and the like. Suitable protecting groups include tert-butoxycarbonyl, benzyloxycarbonyl, benzyl, 4-methoxybenzyl, 2-nitrobenzyl, and the like.

"Heterocycloalkyl" means cycloalkyl, as defined herein, provided that one or more of the ring member carbon atoms indicated is replaced by heteroatom moiety selected from —N, —NR—, —O—, —S— or —$S(O)_2$, wherein R is hydrogen, $(C_{1-6})$alkyl or a protecting group, and any carbocyclic ketone, thioketone or iminoketone derivative thereof (e.g. the term hetero$(C_{5-12})$cycloalkyl includes [1,4'] bipiperidinylyl, dihydrooxazolyl, morpholinyl, 1-morpholin-4-ylpiperidinyl, piperazinyl, piperidyl, pirazolidinyl, pirazolinyl, pyrrolinyl, pyrrolidinyl, quinuclidinyl, and the like). Suitable protecting groups include tert-butoxycarbonyl, benzyloxycarbonyl, benzyl, 4-methoxybenzyl, 2-nitrobenzyl, and the like. For example, a compound of Formula I wherein $R^1$ is piperidin-4-ylcarbonyl may exist as either the unprotected or a protected derivative, e.g. wherein $R^1$ is 1-tert-butoxycarbonylpiperidin-4-ylcarbonyl, and both the unprotected and protected derivatives fall within the scope of the invention.

"Heterocycloalkylene" means cycloalkylene, as defined in this Application, provided that one or more of the ring member carbon atoms indicated, is replaced by heteroatom moiety selected from —N, —NR—, —O—, —S— or —S(O)$_2$—, wherein R is hydrogen or (C$_{1-6}$)alkyl. For example, the instance wherein R$^3$ and R$^4$ together with the carbon atom to which both R$^3$ and R$^4$ are attached form hetero(C$_{3-8}$)cycloalkylene" includes, but is not limited to, the following:

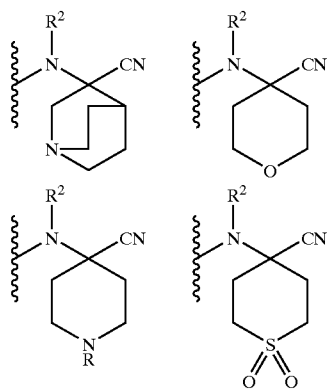

in which R is hydrogen, (C$_{1-6}$)alkyl or a protecting group and R$^2$ is as defined in the Summary of the Invention.

"Heteropolycycloaryl" means polycycloaryl, as defined herein, except one or more of the annular carbon atoms indicated are replaced by a heteroatom moiety selected from —N, —NR—, —O—, —S— or —S(O)$_2$—, wherein R is hydrogen, (C$_{1-6}$)alkyl or a protecting group, and any carbocyclic ketone, thioketone or iminoketone derivative thereof (e.g., hetero(C$_{8-12}$)polycycloaryl includes 3,4-dihydro-2H-quinolinyl, 5,6,7,8-tetrahydroquinolinyl, 3,4-dihydro-2H-[1,8]naphthyridinyl, morpholinylpyridyl, piperidinylphenyl, 1,2,3,4,5,6-hexahydro-[2,2']bipyridinylyl, 2,4-dioxo-3,4-dihydro-2H-quinazolinyl, 3-oxo-2,3-dihydrobenzo[1,4]oxazinyl, etc.).

"Heteroatom moiety" includes —N, —NR—, —O—, —S— or —S(O)$_2$—, wherein R is hydrogen, (C$_{1-6}$)alkyl or a protecting group.

"Hydroxy" means the radical —OH. Unless indicated otherwise, the compounds of the invention containing hydroxy radicals include protected derivatives thereof. Suitable protecting groups for hydroxy moieties include benzyl and the like. For example, a compound of Formula I wherein the R$^9$ contains a hydroxy moiety exist as either the unprotected or a protected derivative, e.g., wherein R$^9$ is benzyloxybenzyl, and both the unprotected and protected derivatives fall within the scope of the invention.

"Iminoketone derivative" means a derivative containing the moiety —C(NR)—, wherein R is hydrogen or (C$_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereo isomers". Stereo isomers that are not mirror images of one another are termed "diastereomers" and stereo isomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has 2$^{n-1}$ enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereo isomers are well known in the art (e.g., see "Advanced Organic Chemistry", 3rd edition, March, Jerry, John Wiley & Sons, New York, 1985). It is understood that the names and illustration used in this Application to describe compounds of Formula I are meant to be encompassed all possible stereo isomers. Thus, for example, the name 1-(1-cyano-1-methylethylcarbamoyl)-3-methylbutylcarbamate is meant to include 1S-(1-cyano-1-methylethylcarbamoyl)-3-methylbutylcarbamate and 1R-(1-cyano-1-methylethylcarbamoyl)-3-methylbutylcarbamate and any mixture, racemic or otherwise, thereof.

"Ketone derivative" means a derivative containing the moiety —C(O)—.

"Methylene" means the divalent radical —CH$_2$— or CH$_2$:, wherein its free valances can be attached to different atoms or the same atom. For example, the instance wherein R$^9$ together with R$^7$ forms trimethylene substituted methylene includes the following:

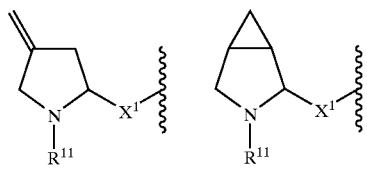

in which X$^{11}$ and R$^{11}$ are as defined in the Summary of the invention, and may be referred to as 2,2-methylene and 1,2-methylene, respectively.

"Nitro" means the radical —NO$_2$.

"Optional" or "optionally" means that the subsequently described event or circumstance may or may not occur, and that the description includes instances where the event or circumstance occurs and instances in which it does not. For example, the phrase "any 1 to 3 annular atoms of any aromatic ring with available valences comprising R$^6$ optionally independently is substituted" means that the aromatic ring referred to may or may not be substituted in order to fall within the scope of the invention.

"N-oxide derivatives" means a derivatives of compound of Formula I in which nitrogens are in an oxidized state (i.e., O←N) and which possess the desired pharmacological activity.

"Oxo" means the radical O.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, ammonium hydroxide, aluminum hydroxide and calcium hydroxide. Acceptable organic bases include ethanolamine, diethanolamine, triethanolamine, tromethamine, N-methylglucamine and the like.

"Phenylene-1,2-dimethylene" means the divalent radical —$CH_2C_6H_4CH_2$—, wherein the methylene moieties are attached at the 1- and 2-positions of the phenylene moiety. For example, a group of Formula (a), wherein $R^9$ together with $R^7$ form optionally substituted phenylene-1,2-dimethylene is illustrated by the following formula:

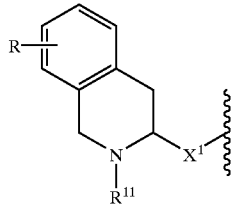

in which R is an optional hydroxy or ($C_{1-4}$)alkyl group and $X^1$ and $R^{11}$ are as defined in the Summary of the Invention.

"Polycycloaryl" means a bicyclic ring assembly (directly linked by a single bond or fused) containing the number of ring member carbon atoms indicated, wherein at least one, but not all, of the fused rings comprising the radical is aromatic, and any carbocyclic ketone, thioketone or iminoketone derivative thereof (e.g., ($C_{9-12}$)polycycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydronaphthalenyl, and the like).

"Prodrug" means a compound which is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates. Suitable esters of compounds of Formula (I) containing a carboxy group, are for example those described by F. J. Leinweber, Drug Metab. Res., 1987, 18, page 379. An especially useful class of esters of compounds of Formula (I) containing a hydroxy group, may be formed from acid moieties selected from those described by Bundgaard et. al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula I in which a reactive site or sites are blocked with protecting groups. Protected derivatives of compounds of Formula I are useful in the preparation of compounds of Formula I or in themselves may be active cysteine protease inhibitors. A comprehensive list of suitable protecting groups can be found in T. W. Greene, *Protecting Groups in Organic Synthesis*, John Wiley & Sons, Inc. 1981.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Ureido" means the radical —$NHC(O)NH_2$. Unless indicated otherwise, the compounds of the invention containing ureido moieties include protected derivatives thereof. Suitable protecting groups for ureido moieties include acetyl, tert-butoxycarbonyl, benzyloxycarbonyl, and the like. For example, a compound of Formula I wherein the $R^9$ contains an ureido moiety may exist as either the unprotected or a protected derivative and the like, and both the unprotected and protected derivatives fall within the scope of the invention.

Presently Preferred Embodiments

While the broadest definition of the invention is set forth in the Summary of the Invention, certain aspects of the invention are preferred. Preferred are compounds of Formula I in which:

$R^1$ represents a group of Formula (a) wherein within Formula (a):
  $X^1$ is —C(O)—;
  $R^5$ represents hydrogen or ($C_{1-6}$)alkyl, preferably hydrogen;

$R^7$ represents hydrogen or methyl, preferably hydrogen, $R^9$ represents (i) $(C_{1-6})$alkyl optionally substituted with —$OR^{14}$, —$SR^{14}$, —$S(O)R^{14}$, —$S(O)_2R^{14}$, —$C(O)R^{14}$, —$C(O)OR^{14}$, —$OC(O)R^{14}$, —$NR^{14}R^{15}$, —$NR^{15}C(O)R^{14}$, —$NR^{15}C(O)OR^{14}$, —$C(O)NR^{14}R^{15}$, —$S(O)_2NR^{14}R^{15}$, —$NR^{15}C(O)NR^{14}R^{15}$ or —$NR^{15}C(NR^{15})NR^{14}R^{15}$, wherein $R^{14}$ is $(C_{3-10})$cycloalkyl$(C_{0-6})$alkyl, hetero$(C_{3-10})$cycloalkyl$(C_{0-6})$alkyl, $(C_{6-10})$aryl$(C_{0-6})$alkyl, hetero$(C_{5-10})$aryl$(C_{0-6})$alkyl, $(C_{9-10})$polycycloaryl$(C_{0-6})$alkyl or hetero$(C_{8-10})$polycycloaryl$(C_{0-6})$alkyl and $R^{15}$ is hydrogen or $(C_{1-6})$alkyl, and wherein within $R^{14}$ said cycloalkyl, heterocycloalkyl, aryl, heteroaryl, polycycloaryl or heterpolycycloaryl ring optionally is substituted by a group selected from —$R^{16}$, —$X^3OR^{16}$, —$X^3SR^{16}$, —$X^3S(O)R^{16}$, —$X^3S(O)_2R^{16}$, —$X^3C(O)R^{16}$, —$X^3(O)OR^{16}$, —$X^3OC(O)R^{16}$, $X^3NR^{16}R^{17}$, —$X^3NR^{17}C(O)R^{16}$, —$X^3NR^{17}C(O)OR^{16}$, —$X^3C(O)NR^{16}R^{17}$, —$X^3S(O)_2NR^{16}R^{17}$, —$X^3NR^{17}C(O)NR^{16}R^{17}$ or —$X^3NR^{17}C(NR^{17})NR^{16}R^{17}$, wherein $X^3$ is a bond or $(C_{1-6})$alkylene, $R^{16}$ is hydrogen or $(C_{1-6})$alkyl and $R^{17}$ is $(C_{3-10})$cycloalkyl$(C_{0-6})$alkyl, hetero$(C_{3-10})$cycloalkyl$(C_{0-6})$alkyl, $(C_{6-10})$aryl$(C_{0-6})$alkyl, hetero$(C_{5-10})$aryl$(C_{0-6})$alkyl, $(C_{9-10})$polycycloaryl$(C_{0-6})$alkyl or hetero$(C_{8-10})$polycycloaryl$(C_{0-6})$alkyl, or (ii) a group selected from $(C_{3-10})$cycloalkyl$(C_{0-6})$alkyl, hetero$(C_{3-10})$cycloalkyl$(C_{0-6})$alkyl, $(C_{6-10})$aryl$(C_{0-6})$alkyl, hetero$(C_{5-10})$aryl$(C_{0-6})$alkyl, $(C_{9-10})$polycycloaryl$(C_{0-6})$alkyl and hetero$(C_{8-10})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{16}$, —$X^3OR^{16}$, —$X^3SR^{16}$, —$X^3S(O)R^{16}$, —$X^3S(O)_2R^{16}$, —$X^3C(O)R^{16}$, —$X^3C(O)OR^{16}$, —$X^3OC(O)R^{16}$, —$X^3NR^{16}R^{17}$, —$X^3NR^{17}C(O)_2R^{16}$, —$X^3NR^{17}C(O)OR^{16}$, —$X^3C(O)NR^{16}R^{17}$, —$X^3S(O)_2NR^{16}R^{17}$, —$X^3NR^{17}C(O)NR^{16}R^{17}$ or —$X^3NR^{17}C(NR^{17})NR^{16}R^{17}$, wherein $X^3$, $R^{16}$ and $R^{17}$ are as defined above; wherein within $R^9$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3R^{12}$, —$X^3SR^{12}$, —$X^3C(O)R^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3OC(O)R^{13}$, —$X^3NR^{12}C(O)R^{13}$, —$X^3S(O)R^{13}$, —$X^3S(O)_2R^{13}$ and —$X^3C(O)R^{13}$, wherein $X^3$ is as defined above, $R^{12}$ at each occurrence independently is hydrogen, $(C_{1-6})$alkyl or halo-substituted $(C_{1-3})$alkyl and $R^{13}$ is $(C_{1-6})$alkyl or halo-substituted $(C_{1-3})$alkyl; and $R^{11}$ represents —$X^4X^5R^{18}$, wherein $X^4$ is —$C(O)$— or —$S(O)_2$—, $X^5$ is a bond, —O— or —$NR^{19}$—, wherein $R^{19}$ is hydrogen or $(C_{1-6})$alkyl, and $R^{18}$ is (i) $(C_{1-10})$alkyl or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl is substituted by —$X^9OR^{24}$, —$X^9C(O)R^{24}$, —$X^9C(O)OR^{24}$, —$X^9C(O)NR^{24}R^{25}$, —$X^9NR^{24}R^{25}$, —$X^9NR^{25}C(O)R^{24}$, —$X^9NR^{25}C(O)OR^{24}$, —$X^9NR^{25}C(O)NR^{24}R^{25}$ or —$X^9NR^{25}C(NR^{25})NR^{24}R^{25}$, wherein $X^9$ is a bond or $(C_{1-6})$alkylene, $R^{24}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{25}$ is hydrogen or $(C_{1-6})$alkyl, wherein within $R^{11}$ any alicyclic or aromatic ring system present may be substituted further by 1 to 5 substituents independently selected from $(C_{1-6})$alkyl, halo, halo-substituted $(C_{1-4})$alkyl, —$OR^{12}$, —$X^3SR^{12}$, —$C(O)OR^{12}$ and —$X^3NR^{12}C(O)OR^{12}$, wherein $X^3$ is a bond or $(C_{1-6})$alkylene and $R^{14}$ is hydrogen or $(C_{1-6})$alkyl.

Within Formula (a), $R^{11}$ particularly represents —$X^4X^5R^{18}$, wherein $X^4$ is —$C(O)$—, $X^5$ is a bond and $R^{18}$ is (i) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl or (ii) phenyl$(C_{0-6})$alkyl or hetero$(C_{5-6})$aryl$(C_{0-6})$alkyl, wherein said phenyl or heteroaryl is substituted by —$X^9OR^{24}$, —$X^9C(O)R^{24}$, —$X^9C(O)OR^{24}$, —$X^9C(O)NR^{24}R^{25}$, —$X^9NR^{24}R^{25}$, —$X^9NR^{25}C(O)R^{24}$, —$X^9NR^{25}C(O)OR^{24}$, —$X^9NR^{25}C(O)NR^{24}R^{25}$ or —$X^9NR^{25}C(NR^{25})NR^{24}R^{25}$ wherein $X^9$ is a bond or $(C_{1-6})$alkylene, $R^{24}$ is phenyl$(C_{0-6})$alkyl or hetero$(C_{5-6})$aryl$(C_{0-6})$alkyl and $R^{25}$ is hydrogen or $(C_{1-6})$alkyl, wherein within $R^{11}$ any aromatic ring system present may be substituted further by 1 to 5 substituents independently selected from $(C_{1-6})$alkyl, halo, halo-substituted $(C_{1-4})$alkyl, —$OR^{12}$, —$X^3SR^{12}$, —$C(O)OR^{12}$ and —$X^3NR^{12}C(O)OR^{12}$ wherein $X^3$ is a bond or $(C_{1-6})$alkylene and $R^{12}$ is hydrogen or $(C_{1-6})$alkyl.

Within Formula (a), $R^{11}$ more particularly represents benzoyl, furylcarbonyl, phenyloxybenzoyl, pyridylthienylcarbonyl, benzoylbenzoyl, thienylcarbonyl, morpholinylcarbonyl, phenyluriedobenzoyl, cyclohexenylcarbonyl or piperazinylcarbonyl, wherein within $R^{11}$ any aromatic ring system present may be substituted further by 1 to 2 substituents independently selected from $(C_{1-6})$alkyl, tert-butoxycarbonylamino, tert-butoxycarbonylaminomethyl, bromo, chloro, ethoxy, fluoro, hydroxy, methoxy and methylsulfanyl.

Within Formula (a), $R^9$ particularly represents (i) $(C_{1-6})$alkyl optionally substituted with —$OR^{14}$ or —$SR^{14}$, wherein $R^{14}$ is $(C_{3-6})$cycloalkyl$(C_{0-6})$alkyl, phenyl$(C_{0-6})$alkyl, biphenylyl$(C_{0-6})$alkyl or hetero$(C_{5-6})$aryl$(C_{0-6})$alkyl, or (ii) a group selected from $(C_{3-6})$cycloalkyl$(C_{0-6})$alkyl, phenyl$(C_{0-6})$alkyl, biphenylyl$(C_{0-6})$alkyl or hetero$(C_{5-10})$aryl$(C_{0-6})$alkyl; wherein within $R^9$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^3NR^{12}R^{12}$, —$X^3NR^{12}C(O)OR^{12}$, —$X^3NR^{12}C(O)NR^{12}R^{12}$, —$X^3NR^{12}C(NR^{12})NR^{12}R^{12}$, —$X^3OR^{12}$, —$X^3SR^{12}$, —$X^3C(O)OR^{12}$, —$X^3C(O)NR^{12}R^{12}$, —$X^3S(O)_2NR^{12}R^{12}$, —$X^3P(O)(OR^3)OR^{12}$, —$X^3OP(O)(OR^3)OR^{12}$, —$X^3OC(O)R^{13}$, —$X^3OC(O)R^{13}$, —$X^3NR^{12}C(O)R^{13}$, —$X^3(O)R^{13}$, —$X^3S(O)_2R^{13}$ and —$X^3C(O)R^{13}$, wherein $X^3$ is a bond or $(C_{1-6})$alkylene, $R^{12}$ at each occurrence independently is hydrogen, $(C_{1-3})$alkyl or halo-substituted $(C_{1-3})$alkyl and $R^{13}$ is $(C_{1-3})$alkyl or halo-substituted $(C_{1-3})$alkyl.

Within Formula (a), $R^9$ more particularly represents cyclohexylmethyl, wherein said cyclohexyl may be substituted by 1 to 5 radicals independently selected from $(C_{1-4})$alkyl, $(C_{1-6})$alkylidene or —$X^3OC(O)R^{13}$, or phenylmethylsulfanylmethyl or phenylsulfanylethyl, wherein said phenyl may be substituted by 1 to 5 radicals independently selected from $(C_{1-4})$alkyl, cyano, halo, halo-substituted $(C_{1-4})$alkyl, nitro, —$OR^{12}$, —$SR^{12}$ and —$C(O)OR^{12}$, wherein $R^{12}$ is hydrogen, $(C_{1-3})$alkyl or halo-substituted $(C_{1-3})$alkyl and $R^{13}$ is $(C_{1-6})$alkyl or halo-substituted $(C_{1-3})$alkyl.

Within Formula (a), $R^9$ more particularly presents a group having the following formula:

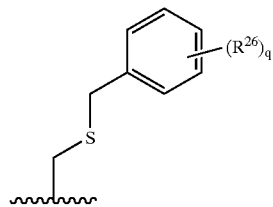

in which q is 0 to 5 and $R^{26}$ at each occurrence is independently selected from $(C_{1-4})$alkyl, cyano, halo, halo-substituted $(C_{1-4})$alkyl, nitro, —$OR^{12}$, —$SR^{12}$ and —C(O)$OR^{12}$, wherein $R^{12}$ is hydrogen, $(C_{1-3})$alkyl or halo-substituted $(C_{1-3})$alkyl and $R^{13}$ is $(C_{1-6})$alkyl or halo-substituted $(C_{1-3})$alkyl.

Within Formula (a), $R^9$ preferably represents benzylsulfanylmethyl, 2-bromobenzylsulfanylmethyl, 2-chlorobenzylsulfanyl, 2-(2-chlorophenylsulfanyl)ethyl, cyclohexyl, 4-ethylidenecyclohexyl, 2-iodobenzylsulfanylmethyl, 2-methylbenzylsulfanylmethyl, 3-methyl-3-trifluorocarbonyloxycyclohexylmethyl, 4-methylenecyclohexylmethyl or 2-nitrobenzylsulfanylmethyl.

$R^2$ preferably represents hydrogen;

$R^3$ preferably is hydrogen or $(C_{1-4})$alkyl, typically hydrogen, or taken with $R^4$ together with the carbon atom to which both $R^3$ and $R^4$ are attached form $(C_{3-8})$cycloalkylene (e.g. cyclopropylene or cyclohexylene).

$R^4$ preferably is hydrogen or taken with $R^3$ together with the carbon atom to which both $R^3$ and $R^4$ are attached form $(C_{3-8})$cycloalkylene (e.g. cyclopropylene or cyclohexylene).

Compounds of Formula II specifically include those in which $R^9$ represents $(C_{6-12})$aryl$(C_{0-6})$alkyl, hetero$(C_{5-12})$aryl$(C_{0-6})$alkyl, —$X^4OR^{14}$, —$X^4SR^{14}$, —$X^4S(O)R^{14}$ or —$X^4NR^{14}R^{15}$, wherein $X^4$ is a bond or $(C_{1-6})$alkylene, $R^4$ is $(C_{6-12})$aryl$(C_{0-6})$alkyl or hetero$(C_{5-12})$aryl$(C_{0-6})$alkyl and $R^{15}$ is hydrogen or $(C_{1-6})$alkyl, and wherein within $R^9$ said aryl or heteroaryl ring optionally is substituted by 1 to 5 radicals independently selected from $(C_{1-6})$alkyl, cyano, halo, halo-substituted $(C_{1-4})$alkyl, nitro, —$X^4NR^{12}R^{12}$, —$X^4OR^{12}$, —$X^4C(O)R^{12}$, —$X^4SR^{12}$, wherein $X^4$ is a bond or $(C_{1-6})$alkylene, $R^{12}$ at each occurrence independently is hydrogen, $(C_{1-6})$alkyl or halo-substituted $(C_{1-3})$alkyl, and $R^{13}$ is $(C_{1-6})$alkyl or halo-substituted $(C_{1-3})$alkyl.

Compounds of Formula II particularly include those in which $R^9$ represents benzyl, benzyloxymethyl, benzylsulfanylethyl, benzylsulfanylmethyl, benzylsulfinylmethyl, indolylmethyl, naphthylmethyl, phenethyl, phenoxyethyl, phenylamino, pyridylmethyl, pyridylsulfanylethyl, phenylsulfanylethyl, thiazolyl or thienyl, wherein within $R^9$ the aromatic ring may be substituted further by 1 to 5 radicals independently selected from $(C_{1-6})$alkyl, cyano, halo, halo-substituted $(C_{1-4})$alkyl, nitro, —$X^4NR^{12}R^{12}$, —$X^4OR^{12}$, —$X^4C(O)R^{12}$, —$X^4SR^{12}$, wherein $X^4$ is a bond or $(C_{1-6})$alkylene, $R^{12}$ at each occurrence independently is hydrogen, $(C_{1-6})$alkyl or halo-substituted $(C_{1-3})$alkyl, and $R^{13}$ is $(C_{1-6})$alkyl or halo-substituted $(C_{1-3})$alkyl.

Compounds of Formula II more particularly include those in which $R^9$ represents 4-aminobenzyl, benzyl, benzyloxymethyl, 2-benzylsulfanylethyl, benzylsulfanylmethyl, 2-bromobenzylsulfanylmethyl, 4-tert-butylbenzylsulfanylmethyl, 2-chlorobenzyl, 4-chlorobenzyl, 2-chlorobenzylsulfanylmethyl, 4-chlorobenzylsulfanylmethyl, 2-(2-chlorophenylsulfanyl)ethyl, 4-cyanobenzyl, 3,4-dichlorobenzylsulfanylmethyl, 1,6-dichlorobenzyl, 3,5-dimethylbenzylsulfanylmethyl, 2-fluorobenzyl, 4-fluorobenzyl, 2-fluorobenzylsulfanylmethyl, 1-formylindol-3-ylmethyl, indol-3-ylmethyl, 2-iodobenzylsulfanylmethyl, 2-methylbenzylsulfanylmethyl, 3-methylbenzylsulfanylmethyl, 3-methylbenzylsulfanylmethyl, 4-methylbenzylsulfanylmethyl, 2-(2-methylphenylsulfanyl)ethyl, 4-methoxybenzyl, 4-methoxybenzylsulfanylmethyl, 4-methoxybenzylsulfinylmethyl, naphth-2-ylmethyl, naphth-2-ylmethylsulfanylmethyl, 3-nitrobenzyl, 1-nitrobenzylsulfanylmethyl, 2-nitrobenzylsulfanylmethyl, 3-nitrobenzylsulfanylmethyl, 4-nitrobenzylsulfanylmethyl, 4-nitrobenzyl, pentafluorobenzylsulfanylmethyl, phenylamino, phenethyl, phenethyloxy, 2-phenoxyethyl, 2-phenoxyethyl 2-phenylsulfanylethyl, pyrid-4-ylmethyl, pyrid-2-ylmethylsulfanylmethyl, pyrid-3-ylmethylsulfanylmethyl, pyrid-4-ylmethylsulfanylmethyl, 2-pyrid-2-ylsulfanylethyl, 2-pyrid-4-ylsulfanylethyl, thiazol-5-yl, thien-2-ylmethyl, 4-trifluoromethylbenzylsulfanylmethyl, 3-trifluoromethylbenzylsulfanylmethyl, 3-trifluoromethoxybenzylsulfanylmethyl, 4-trifluoromethoxybenzylsulfanylmethyl or 4-trifluorosulfanylbenzylsulfanylmethyl, Reference to the preferred embodiments set forth above is meant to include all combinations of particular and preferred groups.

Further preferred are compounds of Formula I selected from a group consisting of:

N-(2-benzylsulfanyl-1R-cyanomethylcarbamoylethyl)-4-hydroxybenzamide;

N-[2-(2-bromobenzylsulfanyl)-1R-cyanomethylcarbamoylethyl]benzamide;

N-[1R-cyanomethylcarbamoyl-2-(2-iodobenzylsulfanyl)ethyl]benzamide;

N-[1R-cyanomethylcarbamoyl-2-(2-cyanobenzylsulfanyl)ethyl]morpholine-4-carboxamide;

N-[3-(2-chlorophenylsulfanyl)-1R-cyanomethylcarbamoylpropyl]benzamide;

N-[1R-cyanomethylcarbamoyl-2-(2-nitrobenzylsulfanyl)ethyl]morpholine- 4-carboxamide N-[1R-cyanomethylcarbamoyl-2-(2-methylbenzylsulfanyl)ethyl]morpholine-4-carboxamide; and N-[1R-cyanomethylcarbamoyl-2-(2-methylbenzylsulfanyl)ethyl]benzamide.

Pharmacology and Utility

The compounds of the invention are cysteine protease inhibitors, in particular the compounds of the invention inhibit the activity of cathepsins B, L, K and/or S and, as such, are useful for treating diseases in which cathepsin B, L, K and/or S activity contributes to the pathology and/or symptomatology of the disease. For example, the compounds of the invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of the invention are useful in treating bone resorption disorders, e.g., osteoporosis. The compounds of the invention also are useful in treating autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to asthma, and allogeneic immune responses, including, but not limited to, organ transplants or tissue grafts.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 10, 11, 12 and 13, infra.

Nomenclature

The compounds of Formula I and the intermediates and starting materials used in their preparation are named in accordance with IUPAC rules of nomenclature in which the characteristic groups have decreasing priority for citation as the principle group as follows: acids, esters, amides and amidines. For example, a compound of Formula I in which $R^1$ is a group of Formula (a), wherein $X^1$ is carbonyl, $R^5$ and $R^7$ are each hydrogen, $R^9$ is benzyl and $R^{11}$ is tert-butoxycarbonyl and $R^2$, $R^3$ and $R^4$ are each hydrogen; that is, a compound having the following structure:

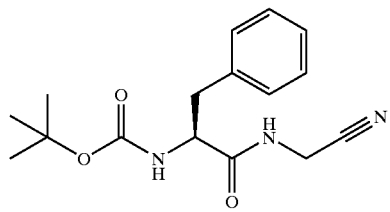

is named tert-butyl 1S-cyanomethylcarbamoyl-2-phenylethylcarbamate and a compound of Formula I in which $R^1$ is a group of Formula (a), wherein $X^1$ is carbonyl, $R^5$ and $R^7$ are each hydrogen, $R^9$ is cyclohexylmethyl and $R^{11}$ is morpholin-4-ylcarbonyl and $R^2$, $R^3$ and $R^4$ are each hydrogen; that is, a compound having the following structure:

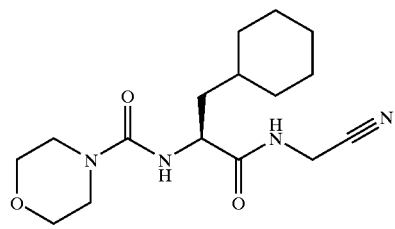

is named N-(1S-Cyanomethylcarbamoyl-2-cyclohexylethyl) morpholine-4-carboxamide.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from 0. 1 micrograms per kilogram body weight (µg/kg) per day to 10 milligram per kilogram body weight (mg/kg) per day, typically 1 µg/kg/day to 1 mg/kg/day. Therefore, a therapeutically effective amount for a 80 kg human patient may range from 10 µg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 15.

Chemistry

Processes for Making Compounds of Formula I:

Compounds of Formula I can be prepared by proceeding as in the following Scheme 1:

Scheme 1

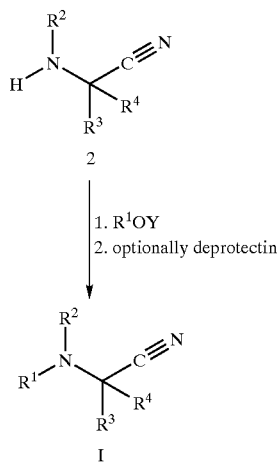

in which Y is hydrogen or an activating group (e.g., 2,5-dioxopyrrolidin-1-yl (NBS), and the like) and each $R^1$, $R^2$, $R^3$ and $R^4$ are as defined in the Summary of the Invention.

Compounds of Formula I can be prepared by reacting a compound of Formula 2, or a protected derivative thereof, with a compound of the formula $R^1OY$, or a protected derivative thereof, and then optionally deprotecting. The reaction is carried out in the presence of a suitable acylation catalyst (e.g., triethylamine) and in a suitable solvent (e.g., acetonitrile, N,N-dimethylformamide (DMF), methylene chloride, or any suitable combination thereof) at 10 to 30° C., preferably at about 25° C., and requires 24 to 30 hours to complete. When Y is hydrogen the reaction can be effected in the presence of a suitable coupling agent (e.g., benzotriazole-1-yloxytrispyrrolidinophosphonium hexafluorophosphate (PyBOP®), 1-(3-dimethylaminopropyl)-3-ethylcarbodiimide hydrochloride (EDC), 0-benzotriazol-1-yl-N,N,N',N'-tetramethyluronium hexafluorophosphate (HBTU), 1,3-dicyclohexylcarbodiimide (DCC), or the like) and base (e.g., N,N-diisopropylethylamine, triethylamine, or the like) and requires 2 to 15 hours to complete. Alternatively, when Y is hydrogen the reaction can be carried out by treating the compound of formula $R^1OH$ with N-methylmorpholine and isobutyl chloroformate in a suitable solvent (e.g., THF, or the like) at between 0 and 5° C. for 30 minutes to an hour and then introducing the compound of Formula 2 to the reaction mixture and allowing the reaction to proceed for 12 to 15 hours.

Deprotection can be effected by any means which removes the protecting group and gives the desired product in reasonable yield. A detailed description of the techniques applicable to the creation of protecting groups and their removal can be found in T. W. Greene, *Protecting Groups in Organic Synthesis*, John Wiley & Sons, Inc. 1981. A detailed description of the preparation of a compound of Formula I according to Scheme 1 is set forth in Examples 4, 5, 6 and 8, infra.

Alternatively, compounds of Formula I can be prepared by reacting a compound of Formula 2 with a compound of the formula $R^1$—SS, wherein SS is a suitable solid support (e.g., thiophenol resin, or the like). The reaction can be carried out in the presence of a suitable acylation catalyst (e.g., 4-dimethylaminopyridine, or the like) and in a suitable solvent (e.g., dry pyrimidine, or the like) and requires 60 to 70 hours to complete. Compounds of Formula I can be prepared by proceeding as in the following reaction Scheme 2:

Scheme 2

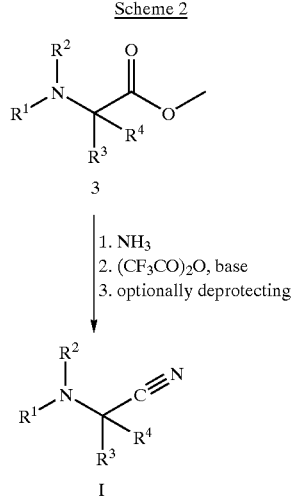

in which each $R^1$, $R^2$, $R^3$ and $R^4$ are as defined in the Summary of the Invention.

Compounds of Formula I can be prepared by treating a compound of Formula 3, or a protected derivative thereof, with ammonia to provide a corresponding amide, then reacting the amide with a suitable dehydrating agent (e.g., trifluoroacetic anhydride, cyanuric chloride, thionyl chloride, phosphonyl chloride, and the like) and optionally deprotecting. The reaction with the ammonia is carried out in a suitable solvent (e.g., methanol) at between 0 and 5° C. and requires 6 to 10 days to complete. The reaction with the dehydrating agent is carried out in the presence of a suitable base (e.g, triethylamine) and in a suitable solvent (e.g., tetrahydrofuran (THF), and the like) at between 0 and 50° C. and requires I to 2 hours to complete. A detailed description of the preparation of a compound of Formula I according to Scheme 2 is set forth in Examples 7 and 8, infra.

Additional Processes for Preparing Compounds of Formula I:

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, etc.). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0 to 80° C.

Prodrug derivatives of the compounds of Formula I can be prepared by methods known to those of ordinary skill in the art (e.g., for further details see Saulnier et al.(1994), *Bioorganic and Medicinal Chemistry Letters*. 4:1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, etc.).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis*, John Wiley & Sons, Inc. 1981.

Compounds of Formula I can be prepared as their individual stereo isomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereo isomers of compounds from their racemic mixture can be found in Jean Jacques Andre Collet, Samuel H. Wilen, Enantiomers, Racemates and Resolutions, Honh Wiley & Sons, Inc. (1981).

In summary, an aspect of the invention is a process for preparing a compound of Formula I, which process comprises:

(A) reacting a compound of Formula 2:

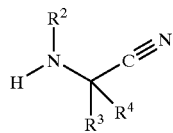

2 or a protected derivative thereof with a compound of the formula $R^1OY$, or a protected derivative thereof, in which Y is hydrogen or an activating group and each $R^1$, $R^2$, $R^3$ and $R^4$ are as defined in the Summary of the Invention; or (B) reacting a compound of Formula 3:

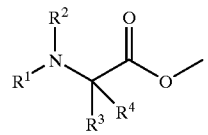

3 with ammonia to provide a corresponding amide and then reacting the amide with trifluoroacetic anhydride, in which each $R^1$, $R^2$, $R^3$ and $R^4$ are as defined in the Summary of the Invention (C) optionally deprotecting a protected derivative of a compound of Formula I to provide a corresponding unprotected derivative;

(D) optionally converting a compound of Formula I into a pharmaceutically acceptable salt;

(E) optionally converting a salt form of a compound of Formula I to non-salt form;

(F) optionally converting an unoxidized form of a compound of Formula I into a pharmaceutically acceptable N-oxide;

(G) optionally converting an N-oxide form of a compound of Formula I its unoxidized form;

(H) optionally converting a non-derivatized compound of Formula I into a pharmaceutically prodrug derivative; and (I) optionally converting a prodrug derivative of a compound of Formula I to its non-derivatized form.

Processes for Preparing Intermediates:

Compounds of Formula 2 can be prepared by reacting a compound of Formula 4:

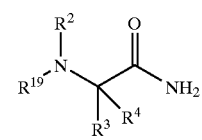

4 in which $R^{19}$ is an amino protecting group and each $R^2$, $R^3$ and $R^4$ are as defined in the Summary of the Invention, with thionyl chloride and then deprotecting. The reaction with the thionyl chloride is carried out in the presence of a suitable base (e.g, triethylamine) and in a suitable solvent (e.g, DMF) at between 0 and 5° C. and requires 30 minutes to an hour to complete. Alternatively, compounds of Formula 2 can be prepared by reacting a compound of Formula 4 with trifluoroacetic anhydride. The deprotection can be effected by any means which removes the protecting group and gives the desired product in reasonable yield. A detailed description of the preparation of a compound of Formula 2 according to above-described procedure is set forth in Example 1, infra.

Compounds of Formula 4 can be prepared by treating a corresponding alkanoyl halide with ammonia. The treatment is carried out in a suitable solvent (e.g., dichloromethane, 5% aqueous sodium carbonate, and the like, or any suitable combination thereof) at 10 to 30° C. and requires 30 minutes to an hour to complete. The alkanoyl halide intermediates can be prepared from the corresponding alkanoic acid by treating with thionyl chloride in a suitable solvent (e.g., dichloromethane) under nitrogen for 30 minutes to an hour. A detailed description of the preparation of a compound of Formula 2 according to the above-described procedures is set forth in Example 1, infra.

Compounds of the formula $R^1$—SS can be prepared by reacting a compound of Formula 5(a) or 5(b):

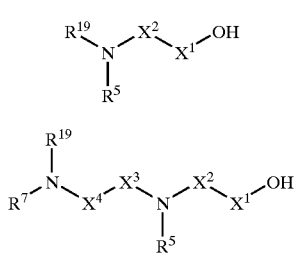

in which $R^{19}$ is an amino protecting group (e.g., tert-butoxycarbonyl, fluoren-9-ylmethoxycarbonyl, or the like) and each $X^1$, $X^2$, $X^3$, $R^5$ and $R^7$ are as defined for Formula I in the Summary of the Invention, with a suitable solid support resin (e.g, Wang (4-benzyloxybenzyl alcohol) resin, thiophenol resin, or the like), deprotecting to provide, respectively, a compound of Formula 6(a) or 6(b):

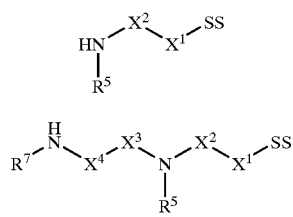

in which SS is a solid support and then reacting the compound of Formula 6(a) or 6(b) with a compound of the formula $R^6OH$ (e.g., benzoic acid, indole-5-carboxylic acid, methanesulfonic acid, or the like).

The reaction between the compound of Formula 5(a) or 5(b) and the resin is carried out in the presence of a suitable coupling agent (e.g., benzotriazole-1-yloxytrispyrrolidinophosphonium hexafluorophosphate (e.g., diisopropylcarbodiimide (DIC), PyBOP®, EDC, HBTU, DCC, or the like) and acylation catalyst (e.g., N,N-diisopropylethylamine, triethylamine, 4-dimethylaminopyridine, 1-hydroxybenzotriazole hydrate, or the like) in a suitable solvent (e.g., methylene chloride, DMF, or the like) and requires approximately 3 to 20 hours to complete. Deprotection can be effected by any means which removes the protecting group and gives the desired product in reasonable yield. The reaction between the compound of Formula 6(a) or 6(b) is carried out with a suitable coupling agent and acylation catalyst. A detailed description of the preparation of a compound of the formula $R^1$—SS according to the above-described procedures is set forth in Examples 2(A–C) and 4(A–C), infra.

Compounds of the formula $R^1OH$ can be prepared by treating a compound of formula $R^1$—SS with a suitable acid (e.g., trifluoroacetic acid, or the like) in a suitable solvent (e.g, methylene chloride, or the like). Alternatively, compounds of the formula $R^1OH$ in which $X^1$ is —C(O)— and $X^2$ is —CHR$^9$— can be prepared by alkylating an organometallic compound of Formula 7(a) or 7(b):

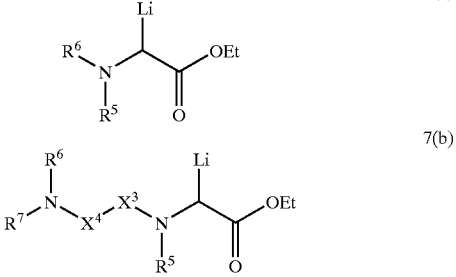

with a compound of the formula $R^9$ L, in which L is a leaving group and each $X^3$, $X^4$, $R^5$, $R^6$, $R^7$ and $R^9$ are as defined for Formula I in the Summary of the Invention, and then converting the resulting ethyl ester to the corresponding acid. The alkylation is carried out in a suitable solvent (e.g., THF) at −78° C. to 0° C. and requires 1 to 2 hours to complete. Conversion the acid can be effected by treating the ester with lithium hydroxide for approximately 15 hours. The organometallic compound is generated by treating a corresponding organo compound with an appropriate base (e.g., N,N-diisopropylethylamine, triethylamine, and the like) and n-butyllithium or tert-butyllithium at −80 to −70° C., preferably at about −78° C., for approximately 30 minutes to an hour. A detailed description of the preparation of a compound of the formula $R^1OH$ according to the above-described procedures is set forth in Example 3, infra.

EXAMPLES

Reference 1

Lithium 2S-Amino-3-cyclohexylpropionate

A solution of methyl 2S-amino-3-cyclohexylpropionate hydrochloride (8.03 mmol, 1 eq) in dichloromethane (80 mL) and saturated NaHC$_{0-3}$ solution (80 mL) was cooled to 0° C. and then the organic layer was treated with a solution of 1.93 M phosgene in toluene (8.3 mL, 2 eq). The mixture was stirred for 10 minutes and then the aqueous was separated and extracted with dichloromethane (3×27 mL). The combined organic layers were dried over sodium sulfate, filtered and concentrated. A portion of the residue (767 μM, 1.0 eq) was stirred under nitrogen together with morpholine (767 μM, 1.0 eq) in dry THF (1 mL) for 12 hours. The mixture was concentrated in vacuo and the residue dissolved in ethyl acetate (1 mL). The solution was washed with water (3×1 mL), dried over sodium sulfate and concentrated. The residue was dissolved in methanol (2 mL) and water (37 μL) and the solution was treated with lithium hydroxide monohydrate (19 mg, 1.05 eq) and then stirred for 12 hours. The solution was adjusted to pH 11 with additional lithium hydroxide monohydrate, heated at 60° C. for 4 hours and then the concentrated in vacuo to provide lithium 2S-morpholin-4-ylcarbonylamino-3-cyclohexylpropionate.

Proceeding as in Reference 1 provided the following compounds:

lithium 2S-piperidin-1-ylcarbonylamino-3-cyclohexylpropionate;

lithium 2S-(4-tert-butoxycarbonylpiperazin-1-ylcarbonylamino)-3-cyclohexylpropionate;

lithium 2S-(4-benzylpiperazin-1-ylcarbonylamino)-3-cyclohexylpropionate;

lithium 2S-(4-ethoxycarbonylpiperazin-1-ylcarbonylamino)-3-cyclohexylpropionate;

lithium 2S-(4-fur-2-ylcarbonylpiperazin-1-ylcarbonylamino)-3-cyclohexylpropionate;

Reference 2

3-Cyclohexyl-2S-(3-methoxybenzyloxycarbonylamino)propionic Acid

A mixture of 2S-amino-3-cyclohexylpropionic acid (2.95 mmol, 1.0 eq) and sodium hydroxide (5.9 mmol, 2 eq) in a 1:1 mixture of THF/water (14 mL) was treated with 3-methoxybenzyloxyformyl chloride (2.95 mmol, 1.0 eq), stirred for 3 hours and then treated with N,N-diethyl ethylenediamine (2.95 mmol, 1.0 eq). The mixture was stirred for approximately 12 hours, adjusted to pH 2 with 1M hydrochloric acid solution (13 mL) and then extracted with ethyl acetate (2×9 mL). The extract was washed with 1 M hydrochloric acid solution (6 mL), dried over sodium sulfate and concentrated to provide 3-cyclohexyl-2S-(3-methoxybenzyloxycarbonylamino)propionic acid as a yellow oil.

Example 1 tert-Butyl 1S-cyanomethylcarbamoyl-2-phenylethylcarbamate

Compound 1

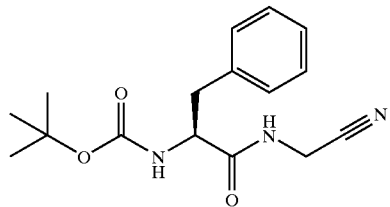

A mixture comprised of 2S-tert-butoxycarbonylamino-3-phenylpropionic acid (28.9 g, 0.109 mol), aminoacetonitrile hydrochloride (10.1 g, 0.109 mol), triethylamine (61 mL, 0.436 mol), DMF (40 mL) and acetonitrile (360 mL) was stirred at room temperature for 27 hours. The mixture was filtered, concentrated to a volume of 100 mL and poured into ice water (1000 mL). The mixture was stirred until a precipitate had formed. The precipitate was collected, washed with water and dried. The dry product was recrystallized from 55% ethanol/water (80 mL). The crystals were collected and recrystallized from 65% ethanol/water (70 mL). The crystals were collected and dried to provide tert-butyl 1S-cyanomethylcarbamoyl-2-phenylethylcarbamate (20.3 g, 0.067 mol) as white needles; $^1$H MNR: δ 1.39 (s, 9H), δ 3.06 (d, 2H, J=7 Hz), δ 4.08 (m, 2H), δ 4.34 (dd, 1H, J=13, 7 Hz), δ 4.97 (d, 1H, J=8 Hz), δ 6.59 (m, 1H), δ 7.23 (m, 5H); ES-MS m/z 304 (MH+).

Proceeding as in Example 1 provided the following compounds of Formula I:

benzyl 5S-tert-butoxycarbonylamino-5-cyanomethylcarbamoylpentylcarbamate (Compound 2); $^1$H MNR: δ 1.37 (m, 15H), δ 1.63 (m, 1H), δ 1.78 (m, 1H), δ 3.14 (dd, 2H, J=13, 6 Hz), δ 4.07 (m, 2H), δ 5.06 (s, 2H), δ 5.42 (br s, 1H), δ 7.32 (m, 5H), δ 7.48 (br s, 1H); ES-MS m/z 419 (MH+);

cyclohexyl 3S-tert-butoxycarbonylamino-N-cyanomethylsuccinamate (Compound 3); $^1$H MNR: δ 1.35 (m, 17H), δ 1.72 (m, 1H), δ 1.83 (m, 1H), δ 2.66 (dd, 1H, J=18, 7 Hz), δ 2.96 (dd, 1H, J=18, 5 Hz), 64.15 (dd, 2H, J=6, 2Hz), δ 4 50 (m, 1H), δ 4.77 (m, 1H), δ 564 (br s, 1H), δ 7.11 (br s, 1H); ES-MS m/z 354 (MH+);

tert-butyl 1S-cyanomethylcarbamoyl-2-(1-formyl-1H-indol-3-yl)ethylcarbamate (Compound 4); $^1$H MNR: δ 1.44 (s, 9H), δ 3.23 (m, 2H), δ 4.08 (m, 2H), δ 4.46 (m, 1), δ 4.95 (br s, 1H), δ 7.38 (m, 4H), δ 7.62 (br s, 1H); ES-MS m/z 371 (MH+);

tert-butyl 2-(3-benzyloxymethyl-3H-imidazol-4-yl)-1S-cyanomethylcarbamoylethylcarbamate (Compound 5); $^1$H MNR: δ 1.39 (s, 9H), δ 3.09 (d, 2H, J=7 Hz), δ 4.00 (d, 2H, J=6 Hz), δ 4.42 (m, 1H), δ 4.45 (s, 2H), δ 5.29 (m, 2H), δ 5.58 (br d, 1H, J=8 Hz), δ 6.79 (s, 1H), δ 7.29 (m, 1H), δ 7.49 (s, 1H), δ 7.93 (br s); ES-MS m/z 414 (MH+);

tert-butyl 2-(4-benzyloxyphenyl)-1S-cyanomethylcarbamoylethylcarbamate (Compound 6); $^1$H MNR: δ 1.40 (s, 9H), δ 3.01 (t, 2H, J=6 Hz), δ 4.07 (t, 2H, J=6 Hz), δ 4.29 (m, 1H), δ 4.90 (br s, 1H), δ 5.02 (s, 2H), δ 6.40 (br s, 1H), δ 6.92 (d, 2H), J=8 Hz), δ 7.09 (d, 2H, J=8 Hz), δ 7.37 (m, 5H); ES-MS m/z 410 (MH+); and tert-butyl 1S-cyanomethylcarbamoyl-2-cyclohexylethylcarbamate (Compound 7); $^1$H MNR: δ 0.94 (m, 2H), δ 1.20 (m, 3H), δ 1.44 (m, 11H), δ 1.71 (m, 6H), δ 4.15 (m, 2H), δ 4.30 (m, 1H), δ 4.87 (br s, 1H), δ 7.04 (br s); ES-MS m/z 210 (M-BuCO$_2$).

Example 2

N-(2-benzylsulfanyl-1R-cyanomethylcarbamoylethyl)benzamide

Compound 8

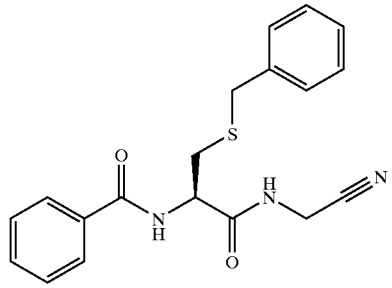

A mixture comprised of 2R-benzoylamino-3-benzylsulfanylpropionic acid (0.508 g, 1.61 mmol), aminoacetonitrile hydrochloride (0.149 g, 1.61 mmol), PyBOP® (0.838 g, 1.61 mmol), N,N-diisopropylethylamine (0.84 mL, 4.83 mmol) and DMF (10 mL) was stirred at room temperature for 2.5 hours. The mixture was concentrated and the residue was taken up into dichloromethane. The dichloromethane mixture was washed with 1N hydrochloric acid, water and aqueous sodium bicarbonate, dried (MgSO$_4$), filtered and concentrated. Product was purified from the residue by silica gel chromatography using 5% methanol in dichloromethane to provide N-(2-benzylsulfanyl-1R-cyanomethylcarbamoyl)ethyl)benzamide (541 mg, 1.53 mmol) as an oil. MS: m/e 353.8 (theory 353.1); Proton NMR Spectrum (DMSO-d$_6$): δ 8.85 (t, 1H), δ 8.75 (d, 1H), δ 7.99 (d, 2H), 7.5 (m, 3H), δ 7.3 (m, 5H), δ 4.7 (m, 1H), δ 4.15 (d, 2H), δ 3.75 (s, 2H), δ 2.8 (m, 2H) ppm.

Proceeding as in Example 2 provided the following compounds of Formula I:

N-[1R-cyanomethylcarbamoyl-2-(4-methylbenzylthioethyl)]benzamide (Compound 9); MS: m/e 367.9 (theory 367.1); NMR Spectrum (DMSO-d$_6$): δ 8.82 (t, 1H), δ 8.69 (d, 1H), δ 7.88 (d, 2H), δ 7.5 (m, 3H), δ 7.16 (d, 2H), δ 7.08 (d, 2H), δ 4.7 (m, 1H), δ 4.2 (d, 2H), δ 3.7 (s, 2H), δ 2.75 (m, 2H), δ 2.1 (s, 3H) ppm;

N-[1R-cyanomethylcarbamoyl)-2-(4-methoxybenzylthioethyl)]benzamide (Compound 10); MS: m/e 383.9 (theory 383.1); NMR Spectrum (DMSO-d$_6$): δ 8.8 (t, 1H) δ 8.65 (d, 1H)δ 7.9 (d, 2H), δ 7.5 (m, 3H), δ 7.25 (d, 2H), δ 6.8 (d, 2H), δ 4.7 (m, 1H), δ 4.2 (d, 2H), δ 3.7 (s, 3H), δ 3.3 (s, 2H), δ 2.8 (m, 2H) ppm;

N-[2-benzyloxy-1S-cyanomethylcarbamoylethyl]benzamide (Compound 11); MS: m/e 337.8 (theory 337.1); NMR Spectrum (DMSO-d$_6$): δ 8.82 (t, 1H)δ 8.67 (d, J=7.8 Hz, 1H) δ 7.91 (d, J=7 Hz, 2H), δ 7.5 (m, 3H), δ 7.3 (m, 5H), δ 4.8 (m, 1H) δ 4.54 (s, 2H), δ 4.17 (d, 2H), δ 3.7 (m, 2H) ppm;

benzyl 1-cyanomethylcarbamoyl-3-methylthiopropylcarbamate (Compound 12); MS: m/e 321.8 (theory 321.1); NMR Spectrum (DMSO-d$_6$): δ 8.7 (t, 1H) δ 7.6 (d, 1H) δ 7.3 (m, 5H), δ 5.0 (q, 2H), δ 4.1 (m, 3H), δ 3.3 (d, 2H), δ 2.4 (m, 2H), δ 1.9 (s, 3H) ppm;

N-[1S-cyanomethylcarbamoyl-3-methylthiopropyl]benzamide (Compound 13); MS: m/e 291.7 (theory 291.1); NMR Spectrum (DMSO-d$_6$): δ 8.7 (t, J=5.6 Hz, 1H), δ 8.6 (d, J=7.7 Hz, 1H), δ 7.9 (m, 2H), δ 7.5 (m, 3H), δ 4.5 (m, 1H), δ 4.11 (d, J=5.6 Hz, 2H), δ 2.5 (m, 2H), δ 2.03 (s, 3H), δ 2.0 (m, 2H) ppm;

benzyl 2-benzylthio-1R-cyanomethylcarbamoylethylcarbamate (Compound 14); MS: m/e 383.8 (theory 383.1); NMR Spectrum (DMSO-d$_6$): δ 8.8 (t, 1H), δ 7.8 (d, 1H), δ 7.4 (m, 10H), δ 5.1 (q, 2H), δ 4.1 (m, 1H), δ 4.2 (s, 2H), δ 3.8 (s, 2H), δ 2.8 (m, 1H), δ 2.6 (m, 1H) ppm;

methyl 4-benzyloxycarbonylamino-4S-cyanomethylcarbamoylbutyrate (Compound 15); MS: m/e 333.6 (theory 333.1); NMR Spectrum (DMSO-d$_6$): δ 8.7 (t, 1H), δ 7.7 (d, 1H), δ 7.4 (m, 5H), δ 5.0 (q, 2H), δ 4.0 (m, 1H), δ 3.55 (s, 3H), δ 3.3 (d, 2H) δ 2.3 (t, 2H), δ 1.8 (m, 2H) ppm;

tert-butyl 2-benzyloxy-1S-cyanomethylcarbamoylethylcarbamate (Compound 16); MS: m/e+Na 355.7 (theory 355.1); NMR Spectrum (DMSO-d$_6$): δ 8.7 (t, 1H), δ 7.0 (d, 1H), δ 7.3 (m, 5H), δ 4.45 (s, 2H), δ 4.2 (m, 1H), δ 4.1 (d, 2H), δ 3.55 (m, 2H), δ 1.4 (s, 9H) ppm;

benzyl 2-benzyloxy-1S-cyanomethylcarbamoylethylcarbamate (Compound 17); NMR Spectrum (DMSO-d$_6$): δ 8.8 (t, 1H), δ 7.7 (d, 1H), δ 7.4 (m, 10H), δ 5.0 (q, 2H), δ 4.5 (s, 2H), δ 4.3 (m, 1H), δ 4.1 (s, 2H), δ 3.6 (m, 2H) ppm;

N-(1-cyanomethylcarbamoylpent-3-ynyl)benzamide (Compound 18); MS: m/e 269.7 (theory 269.1); NMR Spectrum (DMSO-d$_6$): δ 8.8 (t, 1H), δ 8.65 (d, 1H), δ 7.9 (d, 2H), δ 7.5 (m, 3H), δ 4.5 (m, 1H), δ 4.1 (d, 2H), δ 2.5 (m, 2H), δ 1.7 (s, 3H) ppm;

N-(1S-cyanomethylcarbamoyl-2-naphthalen-1-ylethyl)benzamide (Compound 19); $^1$H MNR: δ 3.45 (dd, 1H, J=14, 9 Hz), δ 3.73 (dd, 1H, J=17, 6 Hz), δ 3.90 (dd, 1H, J=19, 6 Hz) δ 4.04 (dd, 1H, J=14, 6 Hz), δ 4.98 (m, 1H), δ 6.67 (m, 1H), δ 6.93 (m, 1H), δ 7.46 (m, 9H), δ 7.74 (m, 2H), δ 8.23 (m, 1H, J=8 Hz); ES-MS m/z 358 (MH+);

N-[2-(4-chlorophenyl)-1S-cyanomethylcarbamoylethyl]benzamide (Compound 20); $^1$MNR: δ 3.19 (m, 2H), δ 3.96 (dd, 1H, J=19, 4 Hz), δ 4.10 (dd, 1H, J=20, 6 Hz), δ 4.98 (m, 1H), δ 6.79 (d, H, J=7 Hz), δ 7.07 (m, 2H), δ 7.22 (m, 2H), δ 7.43 (m, 4H), δ 7.69 (m, 1H), δ 8.08 (d, 1H, J=8 Hz); ES-MS m/z 342 (MH+);

N-(1S-cyanomethylcarbamoyl)-2-naphthalen-2-ylethylbenzamide (Compound 21); $^1$H MNR: δ 3.29 (d, 2H, J=7 Hz), δ 3.81 (dd, 2H, J=18, 6 Hz), δ 3.98 (dd, 1H, J=18, 6 Hz), δ 5.09 (dd, 1H, J=15, 7 Hz), δ 6.74 (br d, 1H, J=7 Hz), δ 7.37 (m, 6H), δ 7.68 (m, 6H); ES-MS m/z 358 (MH+);

N-[1-cyanomethylcarbamoyl-2-(4-cyanophenyl)ethyl]benzamide (Compound 22); $^1$H MNR: δ 3.18 (dd, 1H, J=14, 7 Hz), δ 3.30 (dd, 1H, J=15, 7 Hz), δ 4.03 (dd, 1H, J=17, 6 Hz), δ 4.15 (dd, 1H, J=19, 6 Hz), δ 4.93 (dd, 1H, J=15, 8 Hz), δ 6.81 (d, 1H, J=10 Hz), δ 7.30 (m, 2H), δ 7.43 (m, 3H), δ 7.55 (m, 2H), δ 7.67 (d, 2H, J=8 Hz); ES-MS m/z 333 (MH+);

N-{1S-cyanomethylcarbamoyl-2-[4-(2,6-dichlorobenzyloxy)phenyl]ethyl}benzamide (Compound 23); $^1$H MNR: δ 3.15 (m, 2H), δ 4.08 (t, 2H, J=6 Hz), δ 4.84 (dd, 1H, J=16, 7 Hz), δ 5.24 (m, 3H), δ 6.87 (d, 1H, J=8 Hz), δ 6.98 (m, 4H), δ 7.18 (d, 2H, J=9 Hz), δ 7.32 (m, 4H), δ 7.78 (d, 2H, J=8 Hz); ES-MS m/z 482 (MH+);

cyclohexyl 4-benzoylamino-4S-cyanomethylcarbamoylbutyrate (Compound 24); $^1$H MNR: δ 1.37 (m, 5H), δ 1.53 (m, 2H), δ 1.68 (m, 2H), δ 1.83 (m, 1H), δ 2.17 (m, 2H), δ 2.42 (m, 1H), δ 2.66 (m, 1H), δ 4.15 (m, 2H), δ 4.68 (m, 2H), δ 7.47 (m, 3H), δ 7.79 (m, 2H); ES-MS m/z 372 (MH+);

N-[2-(4-benzoylphenyl)-1S-cyanomethylcarbamoylethyl]benzamide (Compound 25); $^1$H MNR: δ 3.27 (m, 2H), δ 4.00 (dd, 1H, J=15, 6 Hz), δ 4.13 (m, 1H, J=17, 6 Hz), δ 4.23 (d, 1H, J=6 Hz), δ 4.97 (dd, 1H, J=15, 8 Hz), δ 6.96 (d, 1H, J=9 Hz), δ 7.46 (m, 9H), δ 7.71 (m, 5H); ES-MS m/z 412 (MH+);

N-(1S-cyanomethylcarbamoyl-2-phenylethyl)benzamide (Compound 26); $^1$H NMR: δ 3.15 (dd, 1H, J=12, 6 Hz), δ 3.25 (dd, 1H, J=15, 6 Hz), δ 4.08 (t, 2H, J=6 Hz), δ 4.84 (dd, 1H, J=15, 6 Hz), δ 6.68 (br s, 1H), δ 6.77 (br s, 1H), δ 7.29 (m, 5H), δ 7.41 (m, 2H), δ 7.53 (m, 1H), δ 7.67 (d, 2H, J=9 Hz); ES-MS m/z 308 (MH+);

N-[1S-cyanomethylcarbamoyl-2-(1H-indol-3-yl)ethyl]benzamide (Compound 27); $^1$H MNR: δ 3.25 (dd, 1H, J=16, 8 Hz), δ 3.52 (dd, 1H, J=16, 6 Hz), δ 3.95 (dd, 1H, J=18, 4 Hz), δ 4.07 (dd, 1H, J=18, 6 Hz), δ 4.93 (m, 1H), δ 6.44 (br s, 1H), δ 6.85 (d, 1H, J=5 Hz), δ 7.22 (m, 3H), δ 7.38 (m, 3H), δ 7.50 (m, 1H), δ 7.67 (m, 2H, J=8 Hz), δ 7.74 (d, 1H, J=8 Hz), δ 8.18 (br s, 1H); ES-MS m/z 347 (MH+);

N-[1S-cyanomethylcarbamoyl-2-(4-fluorophenylethyl)]benzamide (Compound 28); $^1$H NMR: δ 3.15 (m, 2H), δ 3.97 (dd, 1H, J=18, 6 Hz), δ 4.11 (dd, 1H, J=18, 6 Hz), δ 4.90 (dd, 1H, J=15, 8 Hz), δ 6.95 (m, 3H), δ 7.20 (m, 2H), δ 7.46 (m, 3H), δ 7.68 d, 1H, J=8 Hz); ES-MS m/z 326 (MH+);

N-[2-(2-chlorophenyl)-1S-cyanomethylcarbamoylethyl]benzamide (Compound 29); $^1$H MNR: δ 3.34 (m, 2H), δ 4.04 (dd, 1H, J=16, 6 Hz), δ 4.17 (dd, 1H, J=16, 6 Hz), δ 4.93 (dd, 1H, J=16, 6 Hz), δ 6.85 (m, 1H), δ 7.24 (m, 4H), δ 7.44 (m, 3H), δ 7.72 (m, 2H); ES-MS m/z 342 (MH+);

N-[1S-cyanomethylcarbamoyl-2-(4-methoxyphenylethyl)]benzamide (Compound 30); $^1$H MNR: δ 3.13 (m, 2H), δ 3.76 (m, 4H), δ 4.06 (dd, 1H, J=11, 6 Hz), δ 4.80 (m, 1H), δ 6.83 (m, 4H), δ 7.16 (d, 1H, J=9 Hz), δ 7.46 (m, 2H), δ 7.66 (m, 2H); ES-MS m/z 338 (MH+);

N-[2-(4-benzyloxyphenyl)-1-cyanomethylcarbamoylethyl]benzamide (Compound 31); $^1$H MNR: δ 3.07 (m, 2H), δ 3.90 (m, 1H), δ 4.02 (m, 1H), δ 4.94 (s, 2H), δ 4.95 (m, 1H), δ 6.70 (m, 1H), δ 6.85 (m, 2H), δ 7.09 (m, 2H), δ 7.38 (m, 7H), δ 7.72 (m, 3H); ES-MS m/z 414 (MH+);

benzyl N-(1S-cyanomethylcarbamoyl-2-cyclohexylethyl) isophthalamate (Compound 32); $^1$H MNR: δ 0.86 (m, 2H), δ 1.09 (m, 2H), δ 1.39 (m, 5H), δ 1.67 (m, 4H), δ 3.04 (m, 1H), δ 3.63 (m, 1H), δ 4.11 (m, 1H), δ 4.60 (m, 1H), δ 4.77 (m, 1H), δ 5.33 (s, 2H), δ 7.38 (m, 5H), δ 8.01 (d, 1H, J=9 Hz), δ 8.14 (m, 2H), δ 8.45 (d, 1H, J=12 Hz); ES-MS m/z 448 (MH+);

benzyl N-(1-cyanomethylcarbamoyl-2-cyclohexylethyl) terephthalamate (Compound 33); $^1$H MNR: δ 0.89 (m, 2H), δ 1.13 (m, 3H), δ 1.38 (m, 4H), δ 1.66 (m, 4H), δ 3.10 (m, 1H), δ 3.64 (m, 1H), δ 4.10 (m, 1H), δ 4.80 (dd, 1H, J=15, 8 Hz), δ 5.34 (d, 2H, J=2 Hz), δ 7.37 (m, 5H), δ 7.84 (d, 2H, J=7 Hz), δ 8.03 (m, 2H); ES-MS m/z 448 (MH+);

N-[1-cyanomethylcarbamoyl-2-(2-fluorophenyl)ethyl]benzamide (Compound 34); $^1$H MNR: δ 3.23 (m, 2H), δ 4.06 (dd, 1H, J=18, 6 Hz), δ 4.15 (dd, 1H, J=18, 6 Hz), δ 4.91 (dd, 1H, J=15, 8 Hz), δ 7.01 (m, 2H), δ 7.23 (m, 1H), δ 7.41 (m, 2H), δ 7.52 (m, 2H), δ 7.68 (d, 2H, J=8 Hz); ES-MS m/z 326 (MH+);

N-(2-benzylthio-1R-cyanomethylcarbamoylethyl)-2-(3,5-dimethoxyphenyl)thiazole-4-carboxamide (Compound 35); MS: Calcd. 496; Found M+1=497;

N-(1S-cyanomethylcarbamoyl-2-cyclohexylethyl-2-(3,5-dimethoxyphenyl)thiazole-4-carboxamide (Compound 36); MS: Calcd. 456; Found M+1=457;

N-(1-cyanomethylcarbamoylpent-3-enyl)benzamide (Compound 37); MS: m/e 271.8 (theory 271.1); NMR Spectrum (DMSO-d$_6$): δ 8.7 (t, 1H), δ 8.657 (d, 1H), δ 7.9 (d, 2H), δ 7.5 (m, 3H), δ 5.4 (m, 2H), δ 4.5 (m, 1H), δ 4.1 (d, 2H), δ 2.5 (m, 2H), δ 2.6)d, 3H) ppm;

4-tert-butyl-N-(1S-cyanomethylcarbamoyl-2-cyclohexylethyl)benzamide (Compound 38); $^1$H NMR (CDCl$_3$): δ 8.02 (br s, 1H), δ 7.73 (d, 2H, J=8.7 Hz), δ 7.43 (d, 2H, J=8.5 Hz), δ 7.05 (br d, 1H, J=8.5 Hz), δ 4.79 (dd, 1H, J=15.1, 8.7 Hz), δ 4.10 (dd, 2H, J=19.9 Hz, 5.6 Hz), δ 1.51–1.82 (m, 5H), δ 1.30 (s, 9H), δ 0.83–1.72 (m, 8H), EI MS (M$^+$=369.9);

N-[1S-cyanomethylcarbamoyl-2-cyclohexylethyl]pyrimidine-5-carboxamide (Compound 39); $^1$H NMR (CDCl$_3$): δ 9.33 (s, 1H), δ 8.77 (s, 1H), δ 8.56 (s, 1H), δ 8.14 (br d, 1H, J=8.7 Hz), δ 7.30 (br s, 1H), δ 4.69 (dd, 1H, J=14.9, 9.2 Hz), δ 4.15 (t, 2H, J=3.9 Hz), δ 0.76–2.30 (m, 13H); EI MS (M$^+$=315.9);

N-(1-cyanomethylcarbamoyl-2-cyclohexylethyl) naphthalene-1-carboxamide (Compound 40); $^1$H NMR (CDCl$_3$): δ 8.19 (br d, 1H, J=10.0 Hz), δ 7.81–7.96 (m, 3H), δ 7.47–7.62 (m, 3H), δ 7.35–7.44 (m, 1H), δ 6.69 (d, 1H, J=8.7 Hz), δ 4.90 (dd, 1H), J=15.4, 9.0), δ 4.03 (d, 2H, J=4.9 Hz), δ 0.79–1.89 (m, 13H); EI MS (M$^+$=364.0);

N-(1S-cyanomethylcarbamoyl-2-cyclohexylethyl)-4-fluorobenzamide (Compound 41); $^1$H NMR (CDCl$_3$): δ 7.70–7.83 (m, 2H), δ 7.43 (br s, 1H), δ 7.11 (t, 2H, J=8.7 Hz), δ 6.66 (br d, 1H, J=8.5 Hz), δ 4.69 (dd, 1H, J=15.5, 9.4 Hz), δ 4.14 (dd, 2H, J=19.6, 8.4 Hz), δ 0.67–1.88 (m, 13H); EI MS (M$^+$=331.6);

N-(1S-cyanomethylcarbamoyl-2-cyclohexylethyl)-4-hydroxybenzamide (Compound 42); $^1$H NMR (CDCl$_3$): δ 7.64 (d, 2H, J=9.0 Hz), δ 7.39 (br s, 1H), δ 6.83 (d, 2H, J=9.5 Hz), δ 6.43 (br d, 1H, J=11.2 Hz), δ 4.64 (dd, 1H, J=16.8, 5.6 Hz), δ 4.14–4.09 (m, 2H), δ 0.81–1.89 (m, 13H); EI MS (M+=329.8);

N-(1S-cyanomethylcarbamoyl-2-cyclohexylethyl) naphthalene-2-carboxamide (Compound 43); $^1$H NMR (CDCl$_3$): δ 8.29 (s, 1H), δ 7.76–7.94 (m, 5H), δ 7.51–7.61(m, 2H), δ 6.57 (br d, 1H, J=19.6 Hz), δ 4.73 (dd, 1H, J=19.6, 11.2 Hz), δ 4.17 (dd, 2H, J=13.3, 8.4 Hz), δ 0.80–2.03 (m, 13H); EI MS (M+=363.9);

N-(1S-cyanomethylcarbamoyl-2-cyclohexylethyl)-4-trifluoromethylbenzamide (Compound 44); $^1$H NMR (CDCl$_3$): δ 7.86–7.91 (m, 2H), δ 7.70–7.75 (m, 2H), δ 6.85 (br s, 1H), δ 6.48 (br d, 1H, J=8.4 Hz), δ 4.65 (dd, 1H, J=19.6, 11.2 Hz), δ 4.09–4.20 (m, 2H), δ 0.86–1.74 (m, 13H); EI MS (M+=381.9);

N-(1S-cyanomethylcarbamoyl-2-cyclohexylethyl)-4-methoxybenzamide (Compound 45); $^1$H NMR (CDCl$_3$): δ 7.70–7.73 (m, 3H), δ 6.94 (d, 2H, J=8.5 Hz), δ 6.29 (br s, 1H), δ 4.57–4.69 (m, 1H), δ 4.08–4.17 (m, 2H), δ 3.85 (s, 3H), δ 0.78–1.73 (m, 13H); EI MS (M+=343.9);

N-cyanomethyl-3-cyclohexyl-2S-methylsulfonylaminopropionamide (Compound 46); $^1$H NMR (CDCl$_3$): δ 7.05 (br s, 1H), δ 5.29 (br d, 1H, J=8.7 Hz), δ 4.12–4.20 (m, 1H), δ 3.44 (d, 2H, J=9.7 Hz), δ 3.01 (s, 3H), δ 0.81–1.92 (m, 13H);

N-(1S-cyanomethylcarbamoyl-2-cyclohexylethyl) acetamide (Compound 47); $^1$H NMR (CDCl$_3$): δ 7.51 (br s, 1H), δ 6.15 (br d, 1H, J=8.0 Hz), δ 4.49 (dd, 1H, J=17.8, 11.4 Hz), δ 4.11 (t, 2H, J=18.6 Hz), δ 2.02 (s, 3H), δ 0.72–1.80 (m, 13H); EI MS (M+=251.6);

N-(1-cyanomethylcarbamoyl-2-cyclohexylethyl)-3-fluorobenzamide (Compound 48); $^1$H NMR (CDCl$_3$): δ 7.19–7.55 (m, 5H), δ 6.72 (br s, 1H, J=8.7 Hz), δ 4.69 (dd, 1H, J=10.8, 3.8 Hz), δ 4.14 (dd, 2H, J=2.8, 15.7 Hz), δ 0.86–1.86 (m, 13H); EI MS (M+=331.9);

4-chloro-N-(1-cyanomethylcarbamoyl-2-cyclohexylethyl)benzamide (Compound 49); $^1$H NMR (CDCl$_3$): δ 8.78 (br s, 1H), δ 8.58 (br d, 1H, J=8.0 Hz), δ 7.85 (d, 2H, J=9.0 Hz), δ 7.48 (d, 2H, J=9.2 Hz), δ 4.64 (dd, 1H, J=7.4, 14.1 Hz), δ 4.16 (dd, 2H, J=3.1, 6.1 Hz), δ 0.87–1.85 (m, 13H); EI MS (M+=347.9);

N-(1-cyanomethylcarbamoyl-2-cyclohexylethyl)-2-trifluoromethylbenzamide (Compound 50); $^1$H NMR (CDCl$_3$): δ 7.42–7.78 (m, 5H), δ 6.56 (br d, 1H, J=9.0 Hz), δ 4.81 (dd, 1H, J=15.4, 9.2 Hz), δ 4.10 (t, 2H, J=5.7 Hz), δ 0.80–1.79 (m, 13H); EI MS (M+=382.0);

N-(1-cyanomethylcarbamoyl-2-cyclohexylethyl)-2-fluorobenzamide (Compound 51); $^1$H NMR (CDCl$_3$): δ 8.00 (t, 1H, J=8.4 Hz), δ 7.64 (br s, 1H), δ 7.50 (dd, 1H, J=8.1, 2.5 Hz), δ 7.24–7.30 (m, 1H), δ 7.07–7.18 (m, 2H), δ 4.76 (dd, 1H, J=17.2, 8.2 Hz), δ 4.16 (dd, 2H, J=18.0, 6.2 Hz), δ 0.81–1.89 (m, 13H); EI MS (M+=331.9);

N-(1-cyanomethylcarbamoyl-2-cyclohexylethyl)-4-trifluoromethoxybenzamide (Compound 52); $^1$H NMR (CDCl$_3$): δ 7.01–8.02 (m, 6H), δ 4.75 (br d, 1H, J=14.6 Hz), δ 4.14 (dd, 2H, J=6.0, 18.2 Hz), δ 0.78–1.90 (m, 13H); EI MS (M+=398.0);

N-(1-cyanomethylcarbamoyl-2-cyclohexylethyl)-2,6-difluorobenzamide (Compound 53); $^1$H NMR (CDCl$_3$): δ 7.66 (br s, 1H), δ 7.39 (t, 1H, J=8.7 Hz), δ 6.95 (t, 2H, J=8.7 Hz), δ 6.74 (br d, 1H, J=8.5 Hz), δ 4.85 (dd, 1H, J=14.9, 9.2 Hz), δ 0.86–1.87 (m, 13H); EI MS (M+= 349.9);

N-(1-cyanomethylcarbamoyl-2-cyclohexylethyl)-2,3-difluorobenzamide Compound 54); $^1$H NMR (CDCl$_3$): δ 8.04 (dd, 1H, J=15.3, 8.7 Hz), δ 7.55 (br s, 1H), δ 6.84–7.07 (m, 3H), δ 4.74 (dd, 1H, J=16.6, 7.9 Hz), δ 4.16 (dd, 2H, J=18.0, 5.9 Hz), δ 0.82–1.89 (m, 13H); EI MS (M+=349.9);

N-(1-cyanomethylcarbamoyl-2-cyclohexylethyl)-2,5-difluorobenzamide (Compound 55); $^1$H NMR (CDCl$_3$): δ 7.69 (m, 1H), δ 7.37 (br s, 1H), δ 7.08–7.27 (m, 3H), δ 4.71 (dd, 1H, J=15.1, 6.1 Hz), δ 4.16 (dd, 2H, J=18.0, 6.2 Hz), δ 0.84–1.90)(m, 13H); EI MS (M+=350.1);

N-(1-cyanomethylcarbamoyl-2-cyclohexylethyl)-2,4-difluorobenzamide (Compound 56); $^1$H NMR (CDCl$_3$): δ 7.80 (br s, 1H), δ 7.65 (t, 1H), δ 7.14–7.36 (m, 3H), δ 4.79 (dd, 1H, J=14.9, 7.2 Hz), δ 4.15 (dd, 2H, J=18.2, 5.9 Hz), δ 0.80–1.81)(m, 13H); EI MS (M+=349.9);

N-(1-cyanomethylcarbamoyl-2-cyclohexylethyl)-3,4-dimethoxybenzamide (Compound 57); $^1$H NMR (CDCl$_3$): δ 7.66 (br s, 1H), δ 7.28–7.41 (m, 2H), δ 6.86 (d, 1H, J=8.4 Hz), δ 6.73 (br d, 1H, J=7.9 Hz), δ 4.71 (dd, 1H, J=14.1, 8.4 Hz), δ 4.14 (dd, 2H, J=17.3, 5.9 Hz), δ 3.91 (s, 6H), δ 0.81–1.88 (m, 13H); EI MS (M+=374);

N-(1-cyanomethylcarbamoyl-2-cyclohexylethyl)-3 5-dimethoxybenzamnide (Compound 58); $^1$H NMR (CDCl$_3$): δ 7.41 (br s, 1H), δ 6.88 (d, 2H, J=2.4 Hz), δ 6.59 (t, 2H, J=2.2 Hz), δ 4.67 (dd, 1H, J=16.8, 3.0 Hz), δ 4.12 (dd, 2H, J=17.3, 5.7 Hz), δ 3.81 (s, 6H), δ 0.82–1.88 (m, 13H); EI MS (M+=374);

N-(1-cyanomethylcarbamoyl-2-thiazol-5-ylethyl) benzamide (Compound 59); $^1$H NMR (CDCl$_3$): δ 8.30 (d, 2H, J=8.7 Hz), δ 7.72 (br s, 1H), δ 7.38–7.67 (m, 4H), δ 7.13 (t, 2H, J=8.0 Hz), δ 4.96 (dd, 1H, J=12.3, 5.9 Hz), δ 4.02 (t, 2H, J=10.5 Hz), δ 3.48 (dd, 2H, J=15.7, 5.4 Hz);

N-(1-cyanomethylcarbamoyl-2-thien-2-ylethyl) benzamide (Compound 60); $^1$H NMR (CDCl$_3$): 67.71 (d, 2H, J=8.5 Hz), δ 7.39–7.55 (m, 4H), δ 7.14 (d, 1H, J=11.2 Hz), δ 6.85–6.96 (m, 3H), δ 4.94 (dd, 1H, J=14.6, 6.9 Hz), δ 4.09 (m, 2H), δ 3.41 (t, 2H, J=6.2 Hz); EI MS (M+=313.8);

N-(1S-cyanomethylcarbamoyl-2-cyclohexylethyl) benzamide (Compound 61); Proton NMR (300 MHz, CDCl$_3$): δ 7.79 (d, J=7 Hz, 2H), δ 7.67 (bt, 1H), δ 7.44 (m, 3H), δ 6.75 (bd, 1H), δ 4.74 (m, 1H), δ 4.10 (m, 2H), δ 1.50–1.88 (m, 8H), δ 0.83–1.44 (m, 5H). MS (electrospray): mH+ 313.9 (100%); and N-cyanomethyl-3-cyclohexyl-2S-trifluoromethylsulfonylaminopropionamide (Compound 62).

Example 3 tert-Butyl 5-amino-1S-cyanomethylcarbamoylpentylcarbamate

Compound 63

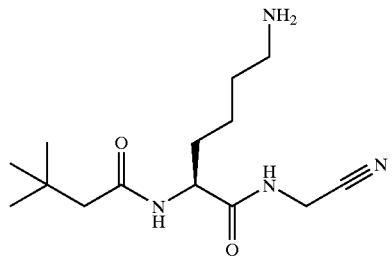

A solution comprised of benzyl 5S-tert-butoxycarbonylamino-5-cyanomethylcarbamoylpentylcarbamate (77 mg, 184 mmol), prepared as in Example 1, in ethanol (2 mL) was treated with ammonium formate (116 mg, 1.84 mmol) and 10% wt palladium on carbon (77 mg). The mixture was stirred for 15 hours and then filtered through Celite. The filter cake washed with ethanol and the combined filtrates were concentrated on a rotary evaporator to provide tert-butyl 5-amino-1S-cyanomethylcarbamoylpentylcarbamate (61 mg, 184 mmol) as a white solid. $^1$H NMR (DMSO-d$_6$): δ 1.42 (m, 17H), δ 2.63 (m, 2H), δ 3.09 (m, 2H); ES-MS m/z 323 (MK+).

Example 4

N-(1S-Cyanomethylcarbamoyl-2-cyclohexylethyl) isophthalamic acid

Compound 64

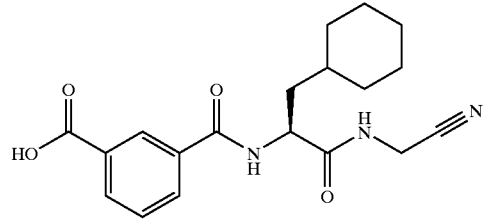

A solution comprised of benzyl N-(1S-cyanomethylcarbamoyl-2-cyclohexylethyl)isophthalamate (82.4 mg, 184 μmol, 1.0 eq), prepared as in Example 2, in ethanol (2 mL) was treated with ammonium formate (116 mg, 1.84 mmol, 10.0 eq) and 10% wt palladium on carbon (82.4 mg). The mixture was stirred for 15 hours and filtered through Celite. The filter cake was washed with ethanol and the combined filtrates were concentrated on a rotary evaporator to provide N-(1S-cyanomethylcarbamoyl-2-cyclohexylethyl)terephthalamic acid (61 mg, 170.7 μmol) as a white solid. $^1$H NMR (MeOH-d$_4$): δ 0.96 (m, 2H), δ 1.26 (m, 2H), δ 1.38 (m, 4H), δ 1.76 (m, 5H), δ 3.23 (d, 1H, J=8 Hz), δ 3.72 (t, 1H, J=7 Hz), δ 4.50 (m, 1H), δ 7.50 (m, 1H), δ 7.97 (m, 1H), δ 8.13 (m, 1H), δ 8.46 (m, 1H); ES-MS m/z 359 (MD+).

Proceeding as in Example 4 provided the following compounds of Formula I:

N-(1-cyanomethylcarbamoyl-2-cyclohexylethyl) terephthalamic acid (Compound 65); $^1$H NMR (MeOH-d$_4$): δ 0.96 (m, 2H), δ 1.32 (m, 5H), δ 1.81 (m, 6H), δ 3.12 (m, 2H), δ 4.92 (m, 1H), δ 7.87 (m, 2H), δ 8.02 (m, 2H); ES-MS m/z 359 (MD+);

N-[1-cyanomethylcarbamoyl-2-(2,6-dichlorophenyl) ethyl]benzamide (Compound 66); $^1$H MNR: δ 3.45 (m, 1H), δ 3.56 (m, 1H), δ 4.13 (m, 2H), δ 5.03 (m, 1H), δ 7.30 (m, 5H), δ 7.63 (m, 3H); ES-MS m/z 376 (MH+); and N-(1-cyanomethylcarbamoyl-2-cyclohexylethyl) phthalamic acid (Compound 67); $^1$H NMR (MeOH-d$_4$): δ 0.94 (d, 2H, J=7 Hz), δ 0.97 (d, 2H, J=7 Hz), δ 1.28 (d, 2H, J=7 Hz), δ 1.47 (m, 1H), δ 1.73 (m, 6H), δ 3.09 (t, 1H; J=6 Hz), δ 3.29 (m, 1H), δ 4.45 d, 1H, J=11, 5 Hz), δ 7.36 (m, 1H), δ 7.58 (m, 2H), δ 7.72 (m, 1H); ES-MS m/z 359 MD+).

Example 5

N-(1S-Cyanomethylcarbamoyl-2-cyclohexylethyl) morpholine-4-carboxamide

Compound 68

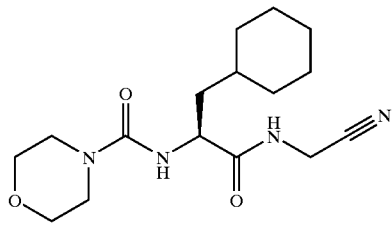

A mixture of lithium 2S-amino-3-cyclohexylpropionate (260 μmol, 1.0 eq), provided as in Reference 1, EDC(286 μmol, 1.1 eq), HOBt (312 μmol, 1.2 eq) and triethylamine (911 μmol, 3.5 eq) in dry dichloromethane (1 mL) was stirred under a nitrogen atmosphere for 5 minutes and then treated with aminoacetonitrile hydrochloride (520 μmol, 2.0 eq). The mixture was stirred 15 hours and then diluted with ethyl acetate (1 mL). The dilution was washed with 1 M hydrochloric acid (2×1 mL), saturated NaHCO$_3$ (1 mL) and saturated NaCl (1 mL), dried over Na$_2$SO$_4$, filtered and concentrated on a rotary evaporator to provide N-(1S-cyanomethylcarbamoyl-2-cyclohexylethyl)morpholine-4-carboxamide. 1H NMR (CDCl$_3$) 0.95 (m, 2H); 1.23 (m, 4H); 1.62 (m, 7H); 3.35 (m, 4H); 3.68 (m, 4H), 4.05 (dd, 2H, J=16, 6 Hz); 4.17 (dd, 2H, J=18, 6 Hz ); 4.27 (m, 1H); 5.01 (d, 1H, J=8 Hz); 7.93 (t, 1H, J=6 Hz); ES-MS m/z 323 (MH+).

Proceeding as in Example 5 provided the following compounds of Formula I:

N-(1S-cyanomethylcarbamoyl-2-cyclohexylethyl) piperidine-1-carboxamide (Compound 69); $^1$H NMR 0.95 (CDCl$_3$) (m, 2H); 1.24 (m, 6H); 1.60 (m, 11H); 3.54 (m, 4H); 4.11 (m, 2H); 4.33 (m, 1H); 4.75 (d, 1H, J=8 Hz); 7.88 (t, 1H, J=6 Hz); ES-MS m/z 321 (MH+);

tert-butyl 4-(1S-cyanomethylcarbamoyl-2-cyclohexylethylcarbamoyl)piperazine-1-carboxylate (Compound 70); $^1$H NMR (CDCl$_3$) 0.89 (m, 2H); 1.23 (m, 4H); 1.44 (s, 9H); 1.66 (m, 7H); 3.36 (s, 4H); 3.40 (s, 4H); 4.03 (dd, 1H, J=18, 5 Hz); 4.14 (dd, 1H, J=18, 6 Hz); 4.38 (dd, 1H, J=15, 8 Hz); 5.32 (d, 1H, J=8 Hz); 8.21 (t, 1H, J=6 Hz); ES-MS m/z 422 (MH+);

N-(1S-cyanomethylcarbamoyl-2-cyclohexylethyl)-4-benzylpiperazine-1-carboxamide (Compound 71); $^1$H NMR (CDCl$_3$) (0.96 (m, 2H); 1.24 (m, 4H); 1.70 (m, 7H); 2.44 (t, 4H, J=5 Hz); 3.37 (t, 4H,1 J=5 Hz); 3.52 (s, 2H); 4.06 (dd, 1H, J=18, 6 Hz); 4.15)dd, 1H, J=18, 6 Hz); 4.32 (m, 1H); 7.30 (m, 5H); 7.72 (t, 1H, J=6 Hz); ES-MS m/z 412 (MH+);

3-methoxybenzyl 1S-cyanomethylcarbamoyl-2-cyclohexylethylcarbamic (Compound 72); $^1$H NMR 0.96 (m, 2H); 1.24 (m, 4H); 1.70 (m, 7H); 3.78 (s, 3H); 4.12 (m, 2H); 4.21 (m, 1H); 5.11 (m, 2H); 6.89 (m, 3H), 7.32 (m, 1H); ES-MS m/z 374 (MH+);

ethyl 4-(1S-cyanomethylcarbamoyl-2-cyclohexylethylcarbamoyl)piperazine-1-carboxylate (Compound 73); and N-(1S-cyanomethylcarbamoyl-2-cyclohexylethyl)-4-fur-2-ylcarbonylpiperazine-1-carboxamide (Compound 74).

Example 6

N-Cyanomethyl-3-cyclohexyl-2S-(3-phenethylureido)propionamide

Compound 75

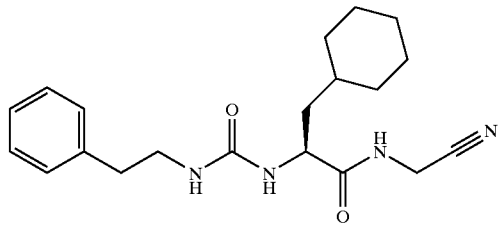

A solution of tert-butyl 1S-cyanomethylcarbamoyl-2-cyclohexylethylcarbamate (103 mmol, 1 eq), provided as in Example 1, in diethyl ether (323 mL) was treated with toluenesulfonic acid monohydrate (206 mmol, 2.0 eq, azeotroped on a rotary evaporator with 2-propanol 3 times, until a white solid had formed) for 12 hours. The supernatant was decanted and the solid was washed extensively with diethyl ether until a powder had formed. A portion of the resulting acid salt (789 μmol, 1 eq) was suspended in dry acetonitrile (1 mL) and then treated with phenethylisocyanate (789 μmol, 1.0 eq) and 4-methylmorpholine (789 μmol, 1 eq) for 12 hours. The mixture was concentrated in vacuo and the residue dissolved in methylene chloride. The solution was stirred with 100 mg Argonaut PS-trisamine resin (345 μmol, 0.4 eq) for 2 hours. The mixture was filtered, diluted with ethyl acetate (1 mL), washed with 1M hydrochloric acid (1 mL), saturated sodium bicarbonate solution and saturated NaCl solution, dried over sodium sulfate, filtered and concentrated to provide N-cyanomethyl-3-cyclohexyl-2S-(3-phenethylureido)propionamide.

Proceeding as in Example 6 provided N-cyanomethyl-3-cyclohexyl-2S-(3-isopropylureido)propionamide (Compound 76).

Proceeding in a fashion analogous to the procedures exemplified above provided the following compounds of Formula I:

N-[1S-cyanomethylcarbamoyl-3-phenylpropyl] benzamide (Compound 77);

N-[1S-cyanomethylcarbamoyl-2-(4-hydroxyphenylethyl)]benzamide (Compound 78);

N-(1-cyanomethylcarbamoyl-2-cyclohexylethyl)-3-hydroxybenzamide (Compound 79); NMR 300 mHz (DMSO-d$_6$), 8.39 (d, J=8.5H$_3$, 1H), 7.26 (m, 3H), 6.69 (m, 1H), 4.64 (m, 1H), 4.14 (dd, J=4.2 and 17.3H$_3$, 2H), 3.30 (m, 2H), 1.71)m, 7H), 1.68–0.80 (m, 6H); MS=329.85 M+=329.40;

1-benzyl-5-benzyloxy—N-(1-cyanomethylcarbamoyl-2-phenylethyl)-2-methyl-1H-indole-3-carboxamide (Compound 80); MS: (m/z [mH$^+$]) 557.0;

N-(1-cyanomethylcarbamoyl-2-phenylethyl)-1-furan-2-ylmethyl-5-methoxy-2-methyl-1H-indole-3-carboxamide (Compound 81); MS: (m/z [mH$^+$]) 470.6;

N-(1-cyanomethylcarbamoyl-2-methylpropyl)-5-ethoxy-1-furan-2-ylmethyl-2-methyl-1H-indole-3-carboxamide (Compound 82); MS: (m/z [mH$^+$]) 436.9;

1-benzo[1,3]dioxol-4-ylmethyl-N-(2-benzylsulfanyl-1-cyanomethylcarbamoylethyl)-5-methoxy-2-methyl-1H-indole-3-carboxamide (Compound 83); MS: (m/z [mH$^+$]) 570.8;

benzyl 5-(1-benzo[1,3]dioxol-4-ylmethyl-5-benzyloxy-2-methyl-1H-indol-3-ylcarbonylamino)-5-cyanomethylcarbamoylpentylcarbamate (Compound 84); MS: (m/z [mH$^+$]) 716.0;

benzyl 5-(1-benzyl-5-benzyloxy-2-methyl-1H-indol-3-ylcarbonylamino)5-cyanomethylcarbamoylpentylcarbamate (Compound 85); MS: (m/z [mH$^+$]) 672.4;

benzyl 5-cyanomethylcarbamoyl-5-(1-furan-2-ylmethyl-5-methoxy-2-methyl-1H-indol-3-ylcarbonylamino) pentylcarbamate (Compound 86); MS: (m/z [mH$^+$]) 586.8;

N-(1-cyanomethylcarbamoylpent-3-enyl)benzamide (Compound 87); NMR 300 mHz (DMSO-d$_6$), 8.67 (t, J=6H$_3$, 1H), 8.53 (d, J=8.5H$_3$, 1H), 7.86 (m, 2H), 7.50 (m, 3H), 5.3–5.7 (m, 2H), 4.40 (m, 1H), 4.12 (d, J=6H$_3$, 2H), 2.3–2.6 (m, 2H), 1.57 (d, J=6.9H$_3$, 3H); MS=271.8 M+=271.32;

N-(1-cyanomethylcarbamoylpent-4-enyl)benzamide (Compound 88); NR 300 mHz (DMSO-d$_6$), 8.66 (m, 11H), 8.57 (d, J=8.2H$_3$, 1H), 7.89 (m, 2H), 7.47 (m, 3H), 5.80 (m, 1H), 4.9–5.05 (m, 2H), 4.4 (m, 1H), 4.11 (d, J=2.5H$_3$, 2H), 2.1 (m, 2H), 1.83 (m, 2H); MS=271.8 M+=271.32;

N-(1-cyanomethylcarbamoylbutyl)benzamide (Compound 89); NMR 300 mHz (DMSO-d$_6$), 8.66 (t, J=5.8H$_3$, 1 h), 8.53 (d, J=8.8H$_3$, 1H), 7.90 (m, 2H), 7.46 (m, 3H), 4.41 (m, 1H), 4.12 (m, 2H), 1.70 (m, 2H), 0.87 (t, J=8H$_3$, 3H); MS=259.8 M+=259.31;

N-(1-cyanomethylcarbamoylpent-4-ynyl)benzamide (Compound 90); NMR 300 mHz (DMSO-d$_6$), 8.67 (t, 1H), 8.61 (d, J=8.5H$_3$, 1H), 7.91 (m, 2H), 7.50 (m, 3H), 4.5 (m, 1H), 4.12 (m, 2H), 2.83 (t, J=2.5H$_3$, 1H), 2.25 (m, 2H), 1.97 (m, 2H); MS=269.9 M+=269.30;

2-chloro-N-(1S-cyanomethylcarbamoyl-2-cyclohexylethyl)benzamide (Compound 91);

N-(1S-cyanomethylcarbamoyl-2-cyclohexylethyl)-2-iodobenzamide (Compound 92); $^1$H NMR (CDCl$_3$): 7.68 (t, J=6 Hz, 1H), 7.34 (m, 4H), δ .41 (d, J=8 Hz, 1H), 4.78 (m, 1H), 4.13 (d, J=12 Hz, 2H), 2.0–0.8 (m, 13H); MS m/e 439.9;

2-bromo—N-(1S-cyanomethylcarbamoyl-2-cyclohexylethyl)benzamide (Compound 93); $^1$H NMR (CDCl$_3$): 7.68 (t, J=5.7 Hz, 1H), 7.58 (dd, J=3, 12 Hz, 7.44 (dd, J=2.1, 12 Hz, 1H), 7.34 (m, 2H), 7.57 (d, J=8 Hz, 1H), 4.79 (m, 1H), 4.13 (d, J=5.7 Hz, 2H), 2.0–0.8 (m, 13H); MS m/e 393.7;

N-(1S-cyanomethlcarbamoylhexyl)benzamide (Compound 94); $^1$H NMR (DMSO): 8.65 (t, J=3 Hz, 1H), 8.54 (d, J=8 Hz, 1H), 7.91 (d, J=7 Hz, 2H), 7.5 (m, 3H), 4.4 (m, 1H), 4.13 (d, J=5 Hz, 2H), 1.74 (m, 2H), 1.3 (m, 6H), 0.85 (t, J=7 Hz, 3H); MS: m/e=287.8;

N-(1S-cyanomethylcarbamoyl-4-phenylbutyl)benzamide (Compound 95); $^1$H NMR (DMSO): 8.67 (t, J=7 Hz, 1H), 8.56 (d, J=9 Hz, 1H), 7.88 (d, J=9 Hz, 2H), 7.4 (m, 3H), 7.2 (m, 5H), 4.45 (m, 1H), 4.11 (d, J=5 Hz, 2H), 2.58 (t, J=8 Hz, 2H), 1.7 (m, 4H); MS: m/e=335.9;

N-(1S-cyanomethylcarbamoyl-2-cyclohexylethyl)2-methoxybenzamide (Compound 96);

N-(1S-cyanomethylcarbamoyl-2-cyclohexylethyl)-3,4,5-trimethoxybenzamide (Compound 97);

benzyl 1S-cyanomethylcarbamoyl-2-cyclohexylethylcarbamate (Compound 98);

isobutyl 1S-cyanomethylcarbamoyl-2-cyclohexylethylcarbamate (Compound 99);

cyclohexylmethyl 1S-cyanomethylcarbamoyl-2-cyclohexylethylcarbamic (Compound 100);

N-(1S-cyanomethylcarbamoyl-3-cyclohexylpropyl) benzamide (Compound 101); $^1$H NMR (DMSO): 8.66 (m, 1H), 8.52 (d, J=8 Hz, 1H), 7.88 (d, J=8 Hz, 2H), 7.45 (m, 3H), 4.37 (m, 1H), 4.12 (m, 2H), 1.9–0,08 (m, 15H); MS: m/e=328.3;

N-(1S-cyanomethylcarbamoyl-2-cyclohexylethyl)-2-trifluoromethoxybenzamide (Compound 102); $^1$H NMR (CDCl$_3$): 7.90 (dd, J=3, 10 Hz, 1H), 7.79 (m, 1H), 7.535 (m, 1H), 7.395 (m, 1H), 7.31 (m, 1H), δ .92 (d, J=8 Hz, 1H), 4.74 (m, 1H), 4.2 (dd, J=6, 17 Hz, 1H), 4.1 (dd, J=6, 17 Hz, 1H), 0.8–1.8 (m, 13H); MS:m/e= 397.9;

N-(1S-cyanomethylcarbamoyl-2-cyclohexylethyl)-3-trifluoromethoxybenzamide (Compound 103); $^1$H NMR (CDCl$_3$): 7.68 (m, 2H), 7.44 (m, 3H), 7.03 (t, J=6.6 Hz, 1H), 4.73 (m, 1H), 4.38 (m, 1H), 4.11 (m, 2H), 0.8–1.8 (m, 11H); MS:m/e=397.9;

N-(1S-cyanomethylcarbamoyl-2-cyclohexylethyl)-3-iodobenzamide (Compound 104); $^1$H NM (CDCl$_3$): 8.1 (t, J=2.8 Hz, 1H), 7.87 (d, J=6.9 Hz, 1H), 7.70 (d, J=7.7 Hz, 1H), 7.19 (t, J=17.5 Hz, 1H), 6.9 (m, 1H), 6.44 (d, J=12 Hz, 4.63 (m, 1H), 4.21 (dd, J=9.6, 6.6 Hz, 1H), 4.1 (dd, J=9.6, 6.6 Hz, 1H) 0.8–2.0 (m, 13H; MS:m/e= 440.0;

3-chloro-N-(1S-cyanomethylcarbamoyl-2-cyclohexylethyl)benzamide (Compound 105); $^1$H NMR (CDCl$_3$): 7.5 (t, J=5.2 Hz, 1H), 7.65 (d, J=7.63 Hz, 1H), 7.51 (d, J=6 Hz, 1H), 7.39 (t, J=8.8 Hz, 1H), 6.59 (d, J=9.9 Hz, 1H), 2.0–0.8 (m, 13H); MS:m/e= 348.0;

2-methoxyethyl 1S-cyanomethylcarbamoyl-2-cyclohexylethylcarbamate (Compound 106);

N-(1S-cyanomethylcarbamoyl-2-cyclohexylethyl) cyclohexanecarboxamide (Compound 107);

N-cyanomethyl-3-cyclohexyl-2S-[2-(4-methoxyphenyl) acetylamino]propionamide (Compound 108); $^1$H NMR (CDCl$_3$): 7.83 (t, J=6 Hz, 1H), 7.13 (d, J=9 Hz, 2H), 6.86 (d, J=12 Hz, 2H), 6.22 (d, J=8 Hz, 1H), 4.55 (m, 1H), 3.95 (m, 2H), 3.78 (S, J=0 Hz, 3H), 0.8–1.8 (m, 13H); MS:m/e=358.0;

N-(1R-cyanomethylcarbamoyl-2-cyclohexylethyl)-2-methylsulfanylbenzamide Compound 109); $^1$H NMR: (CDCl$_3$) 8.11 (t, J=5.5 Hz, 1H), 7.50 (d, J=7.5 Hz, 1H), 7.40 t, J=7.5 Hz, 1H), 7.30 (d, J=1 Hz, J=7.9 Hz, 1H), 7.17 (t, J=7.7 Hz, 1H), 6.94 (d, J=8.4 Hz, 1H), 4.88 (m, 1H), 4.16 (dd, J=5.7 Hz, J=17.3 Hz, 1H), 4.08 (dd, J=5.7 Hz, J=17.3 Hz, 1H), 2.46 (s, 3H), 1.85–0.80 (m, 13H); MS: (M$^+$+1) 360;

N-(1S-cyanomethylcarbamoyl-2-cyclohexylethyl)-3,4-difluoro-benzamide (Compound 110); $^1$H NMR (CDCl$_3$): 7.5 (t, J=5.1 Hz, 1H), 5.88 (d, J=7.7 Hz, 1H), 4.49 (m, 1H), 4.18 d, J=6 Hz, 1H), 4.11 (d, J=6 Hz, 1H), 2.12–0.8 (m, 24H); MS:m/e=320.0;

N-(1S-cyanomethylcarbamoyl-2-cyclohexylethyl)-3-methoxybenzamide (Compound 111); $^1$H NMR: (CDCl$_3$) 7.63 (m, 1H), 7.37–7.28 (m, 3H), 7.06 (m, 1H), 6.76 (d, J=7.7 Hz, 1H), 4.73 (m, 1H), 4.20 (dd, J=5.9 Hz, J=17.3 Hz, 1H), 4.07 (dd, J=5.7 Hz, J=17.3 Hz, 1H), 3.83 (s, 3H), 1.85–0.82 (m, 13H); MS: (M$^+$+1) 344;

4-bromo-N-(1S-cyanomethylcarbamoyl-2-cyclohexylethyl)benzamide (Compound 112); $^1$H NMR: (CDCl$_3$) 7.65–7.57 (m, 4H), 7.10 (m, 1H), 6.48 (d, J=7.7 Hz, 1H), 4.67 (m, 1H), 4.21 (dd, J=5.9 Hz, J=17.3 Hz, 1H), 4.12 (dd, J=5.7 Hz, J=17.3 Hz, 1H), 1.85–0.82 (m, 13H);. MS: (M$^+$+1) 392/394;

N-(1S-cyanomethylcarbamoyl-2-cyclohexylethyl) piperazine-1-carboxamide (Compound 113);

benzyl 4-(2-benzoylamino-2S-cyanomethylcarbamoylethyl)piperidine-1-carboxylate (Compound 114);

3-bromo-N-(1S-cyanomethylcarbamoyl-2-cyclohexylethyl)benzamide (Compound 115); $^1$H NMR: (CD$_3$OD) 8.05 (s, 1H), 7.83 (d, J=7.7 Hz, 1H), 7.71 (d, J=7.5 Hz, 1H), 7.40 (t, J=7.9 Hz, 1H), 4.67 (dd, J=6.9 Hz, J=8.7 Hz, 1H) 4.19 (d, J=17.5 Hz, 1H), 4.11 (d, J=17.3 Hz, 1H), 1.85–0.82 (m, 13H); MS: (M$^+$+1) 392/394;

N-(1S-cyanomethylcarbamoyl-2-cyclohexylethyl)-3-methylbenzamide (Compound 116); $^1$H NMR (DMSO): 7.64 (t, 1H), 7.25 (m, 4H), 6.43 (d, J=12 Hz, 1H), 4.67 (m, 1H), 4.13 (m, 2H), 2.4 (s, 3H), 2.0–0.7 (m, 13H); MS m/e 327.8;

N-(1S-cyanomethylcarbamoyl-2-cyclohexylethyl) pentanamide (Compound 117); $^1$H NMR (CDCl$_3$): 8.11 (t, 1H), 6.53 (d, J=8 Hz, 1H), 4.59 (m, 1H), 4.10 (m, 2H), 2.21 (t, J=4.5 Hz, 2H), 1.8–0.8 (m, 20H); MS m/e 293.8;

N-(1S-cyanomethylcarbamoyl-2-cyclohexylethyl)-2-methylbenzamide (Compound 118); $^1$H NMR (CDCl$_3$): 7.91 (d, J=5.7 Hz, 1H), 7.23 (m, 4H), 6.50 (t, J=3 Hz, 1H), 4.76 (m, 1H), 4.05 (s, J=18 Hz, 1H), 2.38 (d, 3H), 2.0–0.8 (m, 13H); MS m/e 328;

N-(1S-cyanomethylcarbamoyl-2-cyclohexylethyl) thiophene-3-carboxamide (Compound 119); $^1$H NMR (CDCl$_3$): 8.1 (m, 2H), 7.32 (m, t, 2H), 7.08 (d, J=7.9 Hz, 1H), 4.73 (m, 1H), 4.05 (dd, J=6, 17 Hz, 2H), 2.0–0.8 (m, 13H); MS m/e 319.80;

2S-[2-(4-benzyloxyphenyl)acetylamino]-N-cyanomethyl-3-cyclohexylpropionamide (Compound 120); $^1$H NMR (CDCl$_3$): 7.8 (t, 1H), 7.5–6.9 (m, 9H), 6.10 (d, J=8 Hz, 1H), 5.0 (s, 2H), 4.5 (m, 1H), 3.95 (m, 2H), 3.5 (s, 2H), 1.9–1.0 (m, 13H); MS m/e 434.97;

N-cyanomethyl-3-cyclohexyl-2S-[2-(2-methoxyphenyl) acetylamino]propionamide (Compound 121); $^1$H NMR (CDCl$_3$): 7.58 (t, J=7.8 Hz, 1H), 7.23 (m, 2H), 6.91 (m, 2H), 6.21 (d, J=7.2 Hz, 1H), 4.44 (m, 1H), 3.94 (d, J=5.7 Hz, 2H), 3.84 (s, 3H), 3.60 (d, J=8 Hz, 1H), 3.49 (d, J=8 Hz, 1H), 1.8–0.5 (m, 13H); MS m/e 357.89;

N-cyanomethyl-3-cyclohexyl-2-[2-(4-phenoxyphenyl) acetylaminolpropionamide (Compound 122); $^1$H NMR (CDCl$_3$): 7.55 (t, J=3 Hz, 1H), 7.4–6.9 (m,9H), 6.04 (d, J=8.8 Hz, 1H), 4.47 (m, 1H), 4.02 (d, J=6 Hz, 2H), 3.54 (s, 2H), 2.0–0.6 m, 13H); MS m/e 419.94;

N-(1S-cyanomethylcarbamoyl-2-cyclohexylethyl) isonicotinamide (Compound 123); $^1$H NMR (DMSO): 8.68 (d, J=4.5 Hz, 2H), 8.2 (t, J=6.3 Hz, 1H), 7.85 (d, J=7.9 Hz, 1H), 7.66 (d, J=4.7 Hz, 2H), 4.80 (m, 1H), 4.12 (d, J=6 Hz, 2H), 2.0–0.7 (m, 13H); MS m/e 314.8;

N-(1S-cyanomethylcarbamoyl-2-cyclohexylethyl) thiophene-2-carboxamide (Compound 124); $^1$H NMR: (CDCl$_3$) 8.55 (t, J=5.5 Hz, 1H), 7.75 (d, J=7.7 Hz, 1H), 7.64 (dd, J=1 Hz, J=4 Hz, 1H), 7.48 (dd, J=1 Hz, J=5 Hz, 1H), 7.04 (dd, J=5 Hz, J=4 Hz, 1H), 4.82 (q, J=7.5 Hz, 1H), 4.13 (dd, J=5.9 Hz, J=17 Hz, 1H), 3.93 (dd, J=5.7 Hz, 1H), 1.80–0.84 (m, 13H); MS: (M$^+$+1) 319.8;

N-(1S-cyanomethylcarbamoyl-2-piperidin-4-ylethyl) benzamide (Compound 125);

N-[1S-cyanomethylcarbamoyl-2-(1-formyl-1H-indol-3-yl)ethyl]benzamide (Compound 126);

N-[1S-cyanomethylcarbamoyl-2-(1-formyl-1H-indol-3-yl)ethyl]-4-fluorobenzamide (Compound 127);

N-(1S-cyanomethylcarbamoyl-2-cyclohexylethyl) nicotinamide (Compound 128); $^1$H NMR (CDCl$_3$): 9.01 (d, J=4 Hz, 1H), 8.72 (m, 1H), 8.11 (m, 1H), 7.83 (t, J=3 Hz, 1H), 7.39 (m, 2H), 4.77 (m, 1H), 7.14 (m, 2H), 2.0–0.6 (m, 13H); MS m/e 314.88;

tert-butyl 3-(1S-cyanomethylcarbamoyl-2-cyclohexylethylcarbamoyl)phenylcarbamate (Compound 129);

N-[1S-cyanomethylcarbamoyl-2-(1-formyl-1H-indol-3-yl)ethyl]-4-hydroxybenzamide (Compound 130);

N-(1S-cyanomethylcarbamoyl-2-cyclohexylethyl)-1H-indole-5-carboxamide (Compound 131); $^1$H NMR (CDCl$_3$): 11.32 (s, 1H), 8.64 (t, J=6 Hz, 1H), 8.35 (d, J=9 Hz, 1H), 8.22 (s, 1H), 7.68 (dd, J=3, 10 Hz, 1H), 7.42 (m, 1H), 6.54 (m, 1H), 4.12 (d, J=5.7 Hz, 2H), 2.0–0.7 (m, 13H); MS m/e 352.86;

N-(1R-cyanomethylcarbamoyl-2-cyclohexylethyl)-4-methylsulfanylbenzamide (Compound 132);

N-(2-benzylsulfanyl-1R-cyanomethylcarbamoylethyl)-3-fluorobenzamide (Compound 133); $^1$H NMR (CDCl$_3$): 7.18–7.79 (m, 1H), 4.70 (dd, J=13.3, 7.2 Hz, 1H), 4.28 (d, J=7.7 Hz, 1H), 4.22 (d, J=7.4 Hz, 1H), 3.78 (m, 2H), 3.03 (dd, J=14.1, 6.2 Hz, 1H), 2.84 (J=14.1, 7.2 Hz, 1H); MS: m/e=371.88;

N-(2-benzylsulfanyl-1R-cyanomethylcarbamoylethyl)-4-fluorobenzamide (Compound 134); $^1$H NMR (CDCl$_3$): 7.74 (m, 2H), 7.47 (t, J=5.9 Hz, 1H), 7.29 (m, 4H), 7.09 (m, 4H), 4.72 (dd, J=13.6, 6.9 Hz, 1H), 4.11 (m, 2H), 3.77 (s, 5H), 3.02 (dd, J=13.8, 6.2 Hz, 1H), 2.83 (dd, J=13.8, 7.2 Hz, 1H); MS: m/e=371.79;

N-(1S-cyanomethylcarbamoyl-2-(4-methoxybenzylsulfinyl)ethyl]benzamide (Compound 135); $^1$H NMR (DMSO): 8.94 (d, J=8 Hz, 1H), 8.87 (d, J=6 Hz, 1H), 7.87 (d, J=7 Hz, 2H), 7.5 (m, 3H), 7.24 (d, J=10 Hz, 2H), 6.93 (d, J=10 Hz, 2H), 4.80 (dd, J=4, 12 Hz, 1H), 4.14 (d, J=14 Hz, 1H), 4.13 (s, 2H), 3.99 (d, J=14 Hz, 1H), 3.74 (S, 3H), 3.16 (dd, J=12, 14 Hz, 1H), 3.07 (dd, J=14,4 Hz, 1H); MS: m/e=400.00;

N-(1S-cyanomethylcarbamoyl-2-cyclohexylethyl)-4-methylbenzamide (Compound 136); $^1$H NMR (DMSO): 7.7 (t, 1H), 7.65 (d, 2H), 7.25 (d, 2H), 6.65 (d, 1H), 4.75 (m, 1H), 4.2 (dd, 1H), 4.03 (dd, 1H), 2.4 (5, 3H), 2–0.8 (m, 13H); MS: m/e 328.8;

N-(1S-cyanomethylcarbamoyl-2-cyclohexylethyl)-3-phenoxybenzamide (Compound 137); $^1$H NMR (CDCl$_3$): 8.49 (t, J=5.5 Hz, 1H), 7.75 (dd, J=10, 8.5 Hz, 1H), 7.6–6.9 (m, 9H), 4.84 (m, 1H), 3.95 (m, 2H), 2.0–0.8 (m, 13H); MS:m/e=405.93;

3-benzoyl-N-(1S-cyanomethylcarbamoyl-2-cyclohexylethyl)benzamide (Compound 138); $^1$H NMR (CDCl$_3$): 8.19 (t, J=3 Hz, 1H), 8.0 (m, 1H), 7.89 (d, J=8.8 Hz, 1H), 7.76–7.4 (m, 5H), 6.88 (m, 1H), 4.74 (m, 1H), 4.19 (dd, J=6, 6.3 Hz, 1H, 4.08 (dd, J=6, 6.3 Hz, 1H), 2.0–0.8 (m, 13H); MS:m/e=417.95;

N-(2-benzylsulfanyl-1R-cyanomethylcarbamoylethyl)thiophene-3-carboxamide (Compound 139);

3-acetyl-N-(1R-cyanomethylcarbamoyl-2-cyclohexylethyl)benzamide (Compound 140); $^1$H NMR: (CDCl$_3$) 8.33 (t, J=1.5 Hz, 1H), 8.08 (dt, J=1.7 Hz, J=7.7 Hz, 1H), 7.99 (dt, J=1.7 Hz, J=7.9 Hz, 1H), 7.55 (t, J=7.7 Hz, 1H), 7.45 (t, J=6.7 Hz, 1H), 6.92 (d, J=7.9 Hz, 1H), 4.74 (m, 1H), 4.23–4.05 (m, 2H), 2.63 (s, 3H), 1.90–0.84 (m, 13H); MS: (M$^+$+1) 355.8;

N-(2-benzylsulfanyl-1R-cyanomethylcarbamoylethyl)-4-methoxybenzamide (Compound 141); $^1$H NMR (CDCl$_3$): 7.81 (t, J=5.7 Hz, 1H), 7.70 (dt, J=8.9, 2.2 Hz, 2H), 7.20–7.32 (m, J=5H), 7.04 (d, J=7.7 Hz, 1H), 6.89 (dt, J=8.9, 2.0 Hz, 2H), 4.82 (dd, J=14.1, 6.7 Hz, 1H), 4.08 (d, J=5.7 Hz, 2H), 3.83 (s, 3H), 3.74 (s, 2H), 3.00 (dd, J=13.9, 6.7 Hz, 1H), 2.86 (dd, J=13.9, 6.7 Hz, 1H); MS: m/e=383.80;

N-(2-benzylsulfanyl-1R-cyanomethylcarbamoylethyl)furan-2-carboxamide (Compound 142); $^1$H NMR (CDCl$_3$): 7.49 (m, 1H), 7.24–7.39 (m, 5H), 7.14 (m, 1H), 7.04 (m, J=2H), 6.53 (dd, J=3.7, 1.7 Hz, 1H), 4.64 (m, 1H), 4.13 (dd, J=5.9, 1.2 Hz, 2H), 3.79 (dd, J=16.1, 13.6 Hz, 2H), 3.03 (dd, J=14.1, 5.9 Hz, 1H), 2.80 (dd, J=14.3 6.9 Hz, 1H); MS:m/e=343.84;

N-(2-benzylsulfanyl-1R-cyanomethylcarbamoylethyl)furan-3-carboxamide (Compound 143); $^1$H NMR: 8.33 (t, J=5.45 Hz, 1H), 7.16–7.28 (m, 5H), 5.41 (d, J=7.2 Hz, 1H), 4.52 (dd, J=13.9, 6.7 Hz, 1H), 4.06 (d, J=5.7 Hz, 2H), 3.68 (s, 2H), 3.10 (s, 3H), 3.05 (m, 1H), 3.00 (s, 3H), 2.80 (m=1H); MS (320.74);

N-(2-benzylsulfanyl-1R-cyanomethylcarbamoylethyl)-2-methoxybenzamide (Compound 144); $^1$H NMR (CDCl$_3$): 8.75 (D, J=6.9 Hz, 1H), 8.14 (DDJ=2.0 7.9 Hz, 1H), 7.50 (m, 1H), 7.20–7.35 (m, 6H), 7.12 (m, 1H), 4.78 (dd, J=12.6, 6.2 Hz, 1H), 4.19 (dd, J=12.6 6.2 Hz, 1H), 4.07 (dd, J=13.5, 5.4 Hz, 1H), 3.97 (s, 3H), 3.80 (d, J=3.2 Hz, 2H), 3.08 (dd, J=14.0, 3.7 Hz, 1H0, 2.86 (dd, J=14.1, 6.7 Hz, 1H); MS:m/e=383.93;

N-(2-benzylsulfanyl-1R-cyanomethylcarbamoylethyl)-3-methoxybenzamide (Compound 145); $^1$H NMR (CDCl$_3$): 7.96 (t, J=5.7 Hz, 1H), 7.16–7.36 (m, 8H), 7.05 (m, 1H), 4.80 (m, 1H), 4.08 (d, J=5.7 Hz, 1H), 3.80 (s,3H), 3.77 (s, 2H), 2.98 (dd, J=13.9, 6.4 Hz, 1H), 2.86 (dd, J=6.9, 3.9 Hz, 1H); MS: m/e=383.77;

N-(2-benzylsulfanyl-1R-cyanomethylcarbamoylethyl)morpholine-4-carboxamide (Compound 146); $^1$H NMR (CDCl$_3$): 7.45 (m, 1H), 7.23 (m, 5H), 5.28 (m, 1H), 4.39 (m, 1H), 4.16 (dd, J=17.6, 5.9 Hz, 1H), 4.06 (dd, J=11.1, 5.5 Hz, 1H), 3.74 (s, 2H), 3.67 (t, J=4.9 Hz, 4H), 3.31 (m, 4H), 3.00 (dd, J=14.1, 6.4 Hz, 1H), 2.77 (dd, J=13.8, 6.7 Hz, 1H); MS: (362.86);

6-amino-N-(2-benzylsulfanyl-1R-cyanomethylcarbamoylethyl)nicotinamide (Compound 147); $^1$H NMR (CDCl$_3$): 8.42 (d, J=2.5 Hz, 1H), 7.80 (dd, J=8.7 2.5 Hz, 1H), 7.18–7.30(m, 5H), 6.46 (dd, J=9.4 0.7 Hz, 1H), 4.64 (t, J=6.9 Hz, 1H, 4.08 (s, 2H), 3.70 (s, 2H), 2.80 (M, 2H);MS: m/e=369.4474;

N-(2-benzylsulfanyl-1R-cyanomethylcarbamoylethyl)-3-pyrid-3-ylacrylamide (Compound 148); $^1$H NMR (CDCl$_3$): 8.72 (d, J=2.2 Hz, 1H), 8.54 (J=4.7 1.5 Hz, 1H), 7.82 (dt, J=7.9, 2.2 Hz, 1H), 7.57 (d, J=15.6 Hz, 1H), 7.18–7.38 (m, 6H), 6.48 (d, J=15.8 Hz, 1H), 4.61 (m, H), 4.10 (s, 2H), 3.73 (s, 2H), 2.80 (m, 2H); MS: m/e=380.4706;

N-(2-benzylsulfanyl-1R-cyanomethylcarbamoylethyl)naphthalene-2-carboxamide (Compound 149); $^1$H NMR (CDCl$_3$): 8.28 (m, 1H), 7.90 (m, 3H), 7.78 (dd, J=8.4, 1.8 Hz, 1H), 7.57 (m, 2H), 7.17–7.38 (m, 6H), 7.13 (J=7.2 Hz, 1H), 4.77 (m, 1H), 4.14 (d, J=5.9 Hz, 2H), 3.81 (s, 2H), 3.12 (dd, J=14.1,5.9 Hz, 1H), 2.88 (dd, J=14.1, 7.2 Hz, 1H); MS (403.92);

N-(2-benzylsulfanyl-1R-cyanomethylcarbamoylethyl)benzofuran-2-carboxamide (Compound 150); $^1$H NMR (DMSO): 7.66 (dt, J=7.9, 1.2 Hz, 1H), 7.16–7.54 (m, 9H), 4.74 (m, 1H), 4.15 (d, J=6 Hz, 2H), 3.80 (dd, J=15.3, 13.6 Hz, 2H), 3.07 (dd, J=14.1, 5.9 Hz, 1H), 2.87 (ddJ=14.1, 7.1 Hz, 1H); MS (393.83);

N-(2-benzylsulfanyl-1R-cyanomethylcarbamoylethyl)biphenyl-4-carboxamide (Compound 151); $^1$H NMR (CDCl$_3$): 7.81 (dt, J=8.7, 1.5 Hz, 2H), 7.66 (m, 2H), 7.59 (m, 2H), 7.26–7.49 (m, 7H), 7.02 (d, J=7.2 Hz, 1H), 4.73 (m, 1H), 4.14 (dd, J=5.9, 1.2 Hz, 2H), 3.80 (s, 2H), 3.10 (dd, J=14.0, 7.2 Hz, 1H), 2.86 (dd, J=14.1, 7.2 Hz, 1H); MS (429.99);

N-(2-benzylsulfanyl-1R-cyanomethylcarbamoylethyl)benzo[1,3]dioxole-5-carboxami de (Compound 152); $^1$H NMR (CDCl$_3$): 7.21–7.38 (m, 7H), 6.82 (d, J=8.2 Hz, 1H), 6.82 (m, 1H), 4.67 (dd, J=13.3, 6.9 Hz, 1H), 4.11 (dd, J=5.7, 1.6 Hz, 1H), 3.77 (s, 2H), 3.03 (dd, J=14.1, 6.2 Hz, 1H), 2.82 (dd, J=14.1, 6.9 Hz, 1H); MS (397.82);

N-(2-tert-butylsulfanyl-1R-cyanomethylcarbamoylethyl)benzamide (Compound 153); $^1$H NMR (DMSO): 8.77 (t, J=6 Hz, 1H), 8.69 (d, J=9 Hz, 1H), 7.89 (d, J=7 Hz, 2H), 7.5 (m, 3H), 4.58 (m, 1H), 4.13 (t, J=3 Hz, 2H), 3.02 (dd, J=6, 14 Hz, 1H), 2.90 (dd, J=10, 14 Hz, 1H), 1.27 (s, 9H); MS: m/e=319.80;

N-(1R-cyanomethylcarbamoyl-3-phenylsulfanylpropyl)benzamide (Compound 154); $^1$H NMR (DMSO): 8.7 (m, 2H), 7.92 (d, J=7 Hz, 2H), 7.53 (m, 3H), 7.3 (m, 4H), 7.2 (m, 1H), 4.6 (q, J=7 Hz, 1H), 4.13 (d, J=6 Hz, 2H), 3.0 (m, 2H), 2.05 (m, 2H); MS: m/e=353.83;

N-(1S-cyanomethylcarbamoyl-2-cyclohexylethyl)-3-methylthiophene-2-carboxamide (Compound 155); $^1$H NMR: (CDCl$_3$) 7.75 (t, J=6 Hz, 1H), 7.32 (d, J=5 Hz, 1H), 6.90 (d, J=5 Hz, 1H), 6.30 (d, J=7.9 Hz, 1H), 4.72 (m, 1H), 4.19 (dd, J=5.7 Hz, J=17.5 Hz, 1H), 4.05 (dd, J=5.7 Hz, J=17.3 Hz, 1H), 2.51 (s, 3H), 1.85–0.85 (m, 13H); MS: (M$^+$+1) 333.9;

N-(1S-cyanomethylcarbamoyl-2-cyclohexylethyl)-5-methylthiophene-2-carboxamide (Compound 156); $^1$H NMR (CDCl$_3$) 8.14 (t, J=5.7 Hz, 1H), 7.39 (d, J=3.7 Hz, 1H), 6.93 (d, J=7.9 Hz, 1H), 6.72 (dd, J=1 Hz, J=3.7 Hz, 1H), 4.74 (m, 1H), 4.17 (dd, J=5.9 Hz, J=17

Hz, 1H), 3.97 (dd, J=5.5 Hz, J=17.1 Hz, 1H), 2.50 (s, 3H), 1.80–0.82 (m, 13H); MS: (M⁺+1) 333.8;

N-(1S-cyanomethylcarbamoyl-2-cyclohexylethyl)-3-chlorothiophene-2-carboxamide (Compound 157); ¹H NMR: (CDCl₃) 7.52 (d, J=5.2 Hz, 1H), 7.43 (t, J=5.7 Hz, 1H), 7.32 (d, J=7.4 Hz, 1H), 7.01 (d, J=5.2 Hz, 1H), 4.68 (m, 1H), 4.23 (dd, J=5.9 Hz, J=17.5 Hz, 1H), 4.08 (dd, J=6 Hz, J=17.3 Hz, 1H), 1.90–0.85 (m, 13H); MS: (M⁺+1) 353.8;

N-(1S-cyanomethylcarbamoyl-2-cyclohexylethyl)-3-chlorobenzo[b]thiophene2-carboxamide-2-carboxamide (Compound 158); ¹H NMR: (CDCl₃) 7.90–7.78 (m, 3H), 7.65 (d, J=7.9 Hz, 1H), 7.51–7.42 (m, 2H), 4.86 (q, J=8 Hz, 1H), 4.28 (dd, J=5.9 Hz, J=17.3 Hz, 1H), 4.12 (dd, J=5.7 Hz, J=17.3 Hz, 1H), 1.90–0.85 (m, 13H); MS: (M⁺+1) 403.8;

N-(S-cyanomethylcarbamoyl-2-cyclohexylethyl)-5-chlorothiophene-2-carboxamide (Compound 159); ¹H NMR: (CDCl₃) 8.18 (t, J=5.7 Hz, 1H), 7.62 (d, J=7.9 Hz, 1H), 7.40 (d, J=4 Hz, 1H), 6.88 (d, J=4 Hz, 1H), 4.70 (q, J=7.7 Hz, 1H), 4.14 (dd, J=5.7 Hz, J=17 Hz, 1H), 4.05 (dd, J=6 Hz, J=17 Hz, 1H), 1.80–0.84 (m, 13H); MS: (M⁺+1) 353.8;

N-(1S-cyanomethylcarbamoyl-2-cyclohexylethyl)-3-bromothiophene-2-carboxamide (Compound 160); ¹H NMR (CDCl₃): 7.55–7.39 (m, 3H), 7.07 (d, J=5.5 Hz, 1H), 4.68 (m, 1H), 4.25 (dt, 1H), 4.08 (dt, 1H), 2.0–0.8 (m, 13H); MS:m/e=399.74;

N-(1S-cyanomethylcarbamoyl-2-cyclohexylethyl)-5-bromothiophene-2-carboxamide (Compound 161); ¹H NMR (CDCl₃): 8.18 (t, J=5.4 Hz, 1H), 7.62 (d, J=3.5 Hz, 1H), 7.37 (d, J=4.0 Hz, 1H), 7.04 (d, J=4.0 Hz, 1H), 4.70 (dd, J=7.2, 18.7 Hz, 1H), 4.15 (dd, J=5.7, 17.8 Hz, 1H), 4.05 (dd, J=5.7, 17.8, 1H), 1.5–1.8 (m, 7H), 0.8–1.50 (m, 6H); MS:m/e (+1) 399.83;

N-(1S-cyanomethylcarbamoyl-2-cyclohexylethyl)benzo[b]thiophene-2-carboxamide (Compound 162); NMR (MeOH): 8.06 (s, 1H), 7.91 (m, 2H), 7.43 (m, 2H), 4.64 (dd, J=6.7, 8.7 Hz, 1H), 4.21 (d, J=17.3 Hz, 1H), 4.13 (d, J=17.3 Hz, 1H), 1.61–1.90 (M, 8H), 0.89–1.55 (m, 4H); MS: m/e=369.78;

N-(1S-cyanomethylcarbamoyl-2-cyclohexylethyl)-3-ethoxybenzamide (Compound 163); ¹H NMR (MeOH): 8.50 (d, J=7.4 Hz, 1H), 7.3–7.43 (m, 3H), 7.07 (d, J=8.2 Hz, 1H), 4.64 (dd, J=7.7, 19.2 Hz, 2H), 4.15 (dd, J=4.2 Hz, 2H), 4.09 (d, J=6.9 Hz, 1H), 4.04 (d, J=6.9 Hz, 1H), 1.35 (t, J=7.0, 3H), 0.9–1.9 (m, 13H); MS: m/e(+1) 357.94;

tert-butyl 3-(1S-cyanomethylcarbamoyl-3-methylbutylcarbamoyl)phenylcarbamate (Compound 164);

tert-butyl 3-(2-benzylsulfanyl-1R-cyanomethylcarbamoylethylcarbamoyl)phenylcarbamate (Compound 165);

N-(1-cyanomethylcarbamoyl-3-phenoxypropyl)benzamide (Compound 166); ¹H NMR (DMSO): 8.71 (m, =2H), 7.90 (d, J=14 Hz, 2H), 7.5 (m, 3H), 7.25 (m, 2H), 6.9 (m, 3H), 4.65 (m, 1H), 4.14 (d, J=6 Hz, 2H), 4.04 (m, 2H), 2.25 (m, 2H); MS: m/e=337.84;

tert-butyl 1S-cyanomethylcarbamoyl-2-(4-nitrophenyl)ethylcarbamate (Compound 167);

N-(1-cyanomethylcarbamoyl-5-fluoropentyl)benzamide (Compound 168); ¹H NMR (DMSO): 8.69 (t, J=6 Hz, 1H), 8.57 (d, J=8 Hz, 1H), 7.90 (d, J=7 Hz, 2H), 7.5 (m, 3H), 4.42 (dt, J=52, 6 Hz, 2H), 4.43 (m, 1H), 4.13 (s, 2H), 1.83–1.3 (m, 6H); MS: m/e=291.84;

tert-butyl 3-(1S-cyanomethylcarbamoylpentylcarbamoyl)phenylcarbamate (Compound 169);

tert-butyl 3-cyanomethylcarbamoylmethylcarbamoylphenylcarbamate (Compound 170);

N-(2-benzylsulfanyl-1R-cyanomethylcarbamoylethyl)quinoline-3-carboxamide (Compound 171); ¹H NMR (DMSO): 9.30 (d, J=2.5 Hz, 1H), 8.58 (d, J=2.5 Hz, 1H), 8.16 (d, J=8.7 Hz, 1H), 7.90 (d, J=9.2 Hz, 1H), 7.83 (td, J=8.7, 1.5 Hz, 1H), 7.63 (td, J=6.9, 1.2 Hz, 1H), 7.17–7.42 (m, 5H), 4.77 (dd, J=11.8, 7.2 Hz, 1H), 3.81 (s, 2H), 3.12 (dd, J=13.9, 6.2 Hz, 1H), 2.90 (dd, J=14.0, 7.4 Hz, 1H); MS (404.77);

tert-butyl 3-(1S-cyanomethylcarbamoyl-2-cyclohexylethylcarbamoylbenzyl)carbamate (Compound 172); ¹H NMR (CDCl₃): 8.15 (bt, J=5.45 Hz, 1H), 7.63 (d, J=8.1 Hz, 2H), 7.43 (d, J=7.7 Hz, 1H), 5.18 (S, 1H), 4.81 (dd, J=8.4, 18.8 Hz, 1H), 4.25 (d, J=5.2 Hz, 2H), 4.15 (dd, J=5.9, 17.1 Hz, 1H), 3.98 (dd, J=5.9, 17.1 Hz, 1H), 1.45 (s, 9H), 0.8–1.9 (m, 13H); MS: m/e (+1) 357.94;

3-acetylamino-N-(1S-cyanomethylcarbamoyl-2-cyclohexylethyl)benzamide (Compound 173); ¹H NMR (CDCl₃): 8.43 (s, 1H), 8.32 (s, 1H), 7.94 (3, J=7.92 Hz, 1H), 7.59 (s, 1H), 7.54 (s, 1H), 7.38 (d, J=7.9 Hz, 1H), 4.83 (dd, J=7.4, 15.3 Hz, 1H), 4.23 (dd, J=5.7, 17.3 Hz, 1H), 4.06 (dd, J=5.7, 17.3 Hz, 1H), 2.14 (s, 3H), 0.95–1.90 (m, 13h); MS: m/e=370.85;

2S-[2-(4-butoxyphenyl)acetylamino]-N-cyanomethyl-3-cyclohexylpropionamide (Compound 174); NMR (MeOH): 7.19 (d, J=8.9 Hz, 2H), 6.84 (d, J=8.9 Hz, 2H), 4.38 (dd, J=5.9, 9.4 Hz, 1H), 4.12 (d, J=2.2 Hz, 2H), 3.94 (t, J=6.4 Hz, 2H), 3.60 (d, J=14.1 Hz, 1H), 3.46 (d, J=14.1 Hz, 1H), 1.40–1.78 (m, 4H), 1.05–1.3 (m, 3H), 0.95 (t, J=7.4 Hz, 3H); MS: m/e=399.95;

N-[1S-cyanomethylcarbamoyl-2-(4-nitrophenyl)ethyl]morpholine-4-carboxamide (Compound 175);

N-cyanomethyl-3-cyclohexyl-2S-(3-naphth-2-ylureido)propionamide (Compound 176);

N-cyanomethyl-3-cyclohexyl-2S-(3-hexylureido)propionamide (Compound 177);

2S-(3-allylureido)—N-cyanomethyl-3-cyclohexylpropionamide (Compound 178);

N-cyanomethyl-3-cyclohexyl-2S-[3-(2,2,4-trimethylpentyl)ureido]propionamide (Compound 179);

N-(2-benzylsulfanyl-1R-cyanomethylcarbamoylethyl)quinoline-2-carboxamide (Compound 180); ¹H NMR (CDCl₃): 8.90 (d, J=7.8 Hz, 1H), 8.35 (m, 1H), 8.22 (m, 3H), 7.89 (m, 1H), 7.81 (td, J=7.2,1.7 Hz, 1H), 7.66 (td, J=6.9, 1.0 Hz, 1H), 7.37 (m, 2H), 7.14–7.32 (m, 3H), 4.77 (m, 1H), 4.16 (m, 2H), 3.82 (s, 2H), 3.11 (dd, J=14.1, 6.2 Hz, 1H), 3.00 (dd, J=14.1, 6.9 Hz, 1H); MS (404.8);

3-benzylsulfanyl-N-cyanomethyl-2R-(3,3-dimethylureido)propionamide (Compound 181);

3-benzoyl-N-(2-benzylsulfanyl-1R-cyanomethylcarbamoylethyl)benzamide (Compound 182); ¹H NMR (CDCl₃): 8.19 (t, J=1.6 Hz, 1H), 7.96 (m, 2H), 7.78 (m, 2H), 7.61 (m, 2H), 7.51 (m, 2H), 7.23–7.37 (m, 5H), 6.99 (d, J=6.2 Hz, 2H), 4.64 (m, 1H), 4.13 (dd, J=5.9, 1.0 Hz, 2H), 3.80 (d, J=2.5 Hz, 2H), 3.09 (dd, J=14.1, 6.9 Hz, 2H), 2.81 (dd, J=14.1, 7.7 Hz, 1H); MS (457.81);

N-(1S-cyanomethylcarbamoyl-2-cyclohexylethyl)-5-pyrid-2-ylthiophene-2-carboxamnide (Compound 183); $^1$H NMR (CDCl$_3$): 8.55 (d, J=4.95 Hz, 1H), 8;05 (S, J=5.4 Hz, 1H), 7.67–7.73 (m, 2H), 7.62 (d, J=4.0 Hz, 1H), 7.54 (d, J=4.0 Hz, 1H), 7.21 (m, 1H), 7.11 (d, J=7.9 Hz, 1H), 4.77 (dd, J=8.4, 14.3 Hz, 1h), 4.21 (dd, J=5.7, 17.3 Hz, 1H), 4.06 (dd, J=5.7, 17.3 Hz, 1H), 0.8–2.0 (m, 13H); MS: m/e=396.8;

N-(1S-cyanomethylcarbamoyl-2-cyclohexylethyl)-4-methoxythiophene-3-carboxamide (Compound 184); $^1$H NMR (CDCl$_3$): 8.04 (d, J=3.7 Hz, 2H), 7.74 d, J=7.4 Hz, 1H), 6.35 (d, J=3.4 Hz, 1H), 4.68 (dd, J=8.4, 13.9 Hz, 1H), 4.18 (dd, J=6.2, 17.3 Hz, 1H), 4.12 (dd, J=6.2, 17.13 Hz, 1H), 3.91 (s, 3H), 08–1.9 (m, 13H); MS: m/e=349.78;

N-(1S-cyanomethylcarbamoyl-2-cyclohexylethyl)-3-(3-methylbenzoyl)aminobenzamide (Compound 185); $^1$H NMR (CDCl$_3$): 8.47 (s, 1H), 8.30 (t, J=5.4 Hz, 1H), 7.98 (d, J=8.2 Hz, 1H), 7.84 (s, 1H), 7.68 (m, 2H), 7.2–7.48 (m, 4H), 4.84 (dd, J=8.2, 14.6 Hz, 1H), 4.26 (dd, J=6.2, 17.3 Hz, 1H), 4.02 (dd, J=6.2, 17.3 Hz, 1H), 2.35 (s, 3H), 0.8–1.9 (m, 14H); MS: m/e=446.90;

2S-(3-phenylsulfonylureido)-N-cyanomethyl-3-cyclohexylpropionamide (Compound 186);

4-benzoyl-N-(2-benzylsulfanyl-1R-cyanomethylcarbamoylethyl)benzamide (Compound 187); $^1$HNMR (CDCl$_3$): 8.348 (1H), 8.11 (d, J=6.6 Hz, 1H), 7.95 (d, J=6.2 Hz, 1H), 7.56 (m, 1H), 7.14–7.54 (m, 7H), 4.73 (m, 1H), 4.16 (d, J=5.9 Hz, 2H), 3.80 (m, 2H), 3.08 (dd, J=13.9, 7.3 Hz, 1H), 2.87 (dd, J=13.9, 6.2 Hz, 1H), 2.64 (s, 3H); MS (459.86);

N-[2-(4-aminophenyl)-1S-cyanomethylcarbamoylethyl]morpholine-4-carboxamide (Compound 188);

N-(2-benzylsulfanyl-1R-cyanomethylcarbamoylethyl)nicotinamide (Compound 189);

N-(2-benzylsulfanyl-1R-cyanomethylcarbamoylethyl)isonicotinamide (Compound 190);

2S-(3-tert-butylureido)-N-cyanomethyl-3-cyclohexylpropionamide (Compound 191);

N-(1S-cyanomethylcarbamoyl-2-cyclohexylethyl)-4-methylpentanamide (Compound 192); $^1$H NMR (CDCl$_3$): 8.25 (t, J=5.7 Hz, 1H), 6.60 (d, J=8.2 Hz, 1H), 4.60 (dd, J=8.7, 14.6 Hz, 1H), 4.12 (dd, J=5.7, 14.8 Hz, 1H), 4.04 (dd, J=5.7, 14.8 Hz, 1H), 2.20 (t, J=8.2 Hz, 2H), 0.85 (d, J=6.5, 6H), 1.1–1.8 (m, 16H); MS: m/e (+1) 307.92;

N-(1S-cyanomethylcarbamoyl-2-cyclohexylethyl)cyclopent-1-enecarboxamide (Compound 193); $^1$H NMR (CDCl$_3$): 7.79 (t, J=5.9 Hz, 1H), 6.49 (m, 1H), 6.08 (d, J=7.9 Hz, 1H), 4.58 (dd, J=8.4, 14.6 Hz, 1H), 4.17 (dd, J=5.9, 17.3 Hz, 1H), 4.04 (dd, J=5.9, 17.3 Hz, 1H), 2.52 (m, 4H), 2.0 (m, 2H), 1.68 (m, 8H), 0.8–1.4 (m, 5H); MS: m/e (+1) 303.82;

tert-butyl 2-benzylsulfanyl-1R-cyanomethylcarbamoylethylcarbamate (Compound 194);

N-(1S-cyanomethylcarbamoyl-2-cyclohexylethyl)-1H-imidazole-4-carboxamide (Compound 195); $^1$H NMR (DMSO): 8.10 (s, 1H), 7.60 (m, 4H), 4.62 (m, 1H), 4.10 (d, J=7.2 Hz, 2H), 0.8–1.90 (m, 13H); MS: m/e (+1) 303.79;

N-(1S-cyanomethylcarbamoyl-2-cyclohexylethyl)-cyclopentanecarboxamide (Compound 196); $^1$H NMR (DMSO): 7.88 (t, J=5.45 Hz, 1H), 6.15 (d, J=8.17 Hz, 1H), 4.55 (dd, J=8.7, 14.6 Hz, 1H), 4.16 (dd, J=5.7, 17.3 Hz, 1H), 4.06 (dd, J=5.7, 17.3 Hz, 1H), 2.65 (m, 1H), 0.8–1.95 (m, 21H); MS: m/e (+1) 305.91;

N-(1S-cyanomethylcarbamoyl-2-cyclohexylethyl)cyclohex-1-enecarboxamide (Compound 197); $^1$H NMR (DMSO): 7.65 (t, J=5.2 Hz, 1H), δ .69 (m, 1H), 6.02 (d, J=7.7 Hz, 1H), 4.56 (dd, J=8.7, 14.1 Hz, 1H), 4.17 (dd, J=5.9, 17.3 Hz, 1H), 4.05 (dd, J=5.9, 17.3 Hz, 1H), 2.19 (m, 4H), 1.48–1.85 (m, 13H), 0.8–1.4 (m, 4H); MS: m/e (+1) 317.86;

N-(1S-cyanomethylcarbamoyl-2-cyclohexylethyl)-5-methylsulfanylthiophene2-carboxamide (Compound 198); $^1$H NMR (CDCl$_3$): 8.12 (t, J=5.4 Hz, 1H), 7.42 (d, J=4.0 Hz, 1H), 7.18 (d, J=7.7 Hz, 1H), 6.9 (d, J=4.0 Hz, 1H), 4.73 (dd, J=8.2, 14.6 Hz, 1H), 4.18 (dd, J=8.2, 14.6 Hz, 1H), 2.55 (s, 3H), 1.75 (m, 8H), 0.8–1.5 (m, 6H); MS:m/e (+1) 365.77;

N-(1S-cyanomethylcarbamoyl-2-cyclohexylethyl)isobutyramide (Compound 199); $^1$H NMR (CDCl$_3$): 7.88 (t, J=5.7 Hz, 1H), 6.14 (d, J=7.9 Hz, 1H), 4.55 (dd, J=8.7, 14.6 Hz, 1H), 4.15 (dd, J=5.7, 15.6 Hz, 1H), 4.06 (dd, J=5.7, 15.6 Hz, 1H), 2.40 (m, 1H), 1.57–1.80 (m, 8H), 0.8–1.40 (m, 11H); MS: m/e (+1) 279.89;

N-(1S-cyanomethylcarbamoyl-2-cyclohexylethyl)furan-2-carboxamide (Compound 200); $^1$H NMR (CDCl$_3$): 7.45 (m, 2H), 7.14 (d, J=3.5 Hz, 1H), 6.67 (d, J=8.2 Hz, 1H), 6.51 (m, 2H), 4.66 (dd, J=8.9, 14.1 Hz, 1H), 4.20 (dd, J=5.9, 17.6 Hz, 1H), 4.06 (dd, J=5.9, 17.6, 1H), 1.5–1.9 (m, 7H), 0.8–1.40 (m, 6H); MS: m/e (+1) 303.63;

N-cyanomethyl-3-cyclohexyl-2S-(3-cyclohexylureido)propionamide (Compound 201);

N-cyanomethyl-3-cyclohexyl-2S-(3-phenylureido)propionamide (Compound 202);

3-acetylamino-N-(1S-cyanomethylcarbamoylpentyl)benzamide (Compound 203);

N-(1S-cyanomethylcarbamoyl-2-cyclohexylethyl)furan-3-carboxamide (Compound 204); $^1$H NMR (CDCl$_3$): 8.5 (t, J=6 Hz, 1H), 7.95 (s, 1H), 7.8 (d, J=6 Hz, 1H), 7.4 (s, 1H), 6.65 (s, 1H), 4.70 (m. 1H), 4.15 (dd, J=6, 6 Hz, 1H), 3.95 (dd, J=6, 6 Hz, 1H), 2.0–0.8 (m, 13H); MS:m/e=303.70;

N-(1S-cyanomethylcarbamoyl-2-cyclohexylethyl)-6-hydroxynicotinamide (Compound 205); $^1$H NMR (DMSO): 12.1 (s, 1H), 8.8 (t, J=5.7 Hz, 1H), 8.4 (d, J=7.5 Hz, 1H), 8.1 (d, J=2.1 Hz, 1H), 7.9 (dd, J=3, 10 Hz, 1H), 6.43 (d, J=10 Hz, 1H), 4.5–4.2 (m, 1H), 4.18 (d, J=6 Hz, 1H), 1.8–0.8 (m, 13H); MS:m/e=330.82;

N-(1S-cyanomethylcarbamoyl-2-cyclohexylethyl)benzofuran-2-carboxamide (Compound 206); $^1$H NMR (CDCl$_3$): 7.95 (t, J=6 Hz, 1H), 7.8–7.2 (m, 6H), 4.95 (m, 1H), 4.30 (dd, J=6, 6 Hz, 1H), 4.10 (dd, J=6, 6 Hz, 1H), 2.0–0.8 (m, 13H); MS:m/e=303.70;

N-(1S-cyanomethylcarbamoyl-2-cyclohexylethyl)quinoline-3-carboxamide (Compound 207); $^1$H NMR (DMSO): 9.2 (1H), 8.8 (s, 1H), 8.0 (d, J=6 Hz, 2H), 7.8 (t, J=6 Hz, 1H), 7.65 (t, J=6 Hz, 1H), 4.2 (m, 2H), 2.0–0.8 (m, 15H); MS:m/e=364.86;

N-(1S-cyanomethylcarbamoyl-2-cyclohexylethyl)-4-hydroxy-3-nitrobenzamide (Compound 208); $^1$H NMR (CDCl$_3$): 10.7 (s, 1H), 8.3 (s, 2H), 7.9 (d, J=6 Hz, 1H), 7.1 (d, J=6 Hz, 1H), 4.9 (m, 1H), 4.3 (m, 2H), 2.2–0.8 (m, 13H); MS:m/e=374.83;

N-(1S-cyanomethylcarbamoyl-2-cyclohexylethyl)-3-nitrobenzamide (Compound 209); $^1$H NMR (DMSO): 8.8–8.2 (m, 4H), 8.1 (d, J=6.8 Hz, 1H), 7.5 (t, J=6.8 Hz, 1H), 4.9 (m, 1H), 4.45 (dd, J=6, 6, 1H), 4.25 (dd, J=6, 6, 1H), 2.0–0.8 (m, 13H); MS:m/e=358.75;

N-(1S-cyanomethylcarbamoyl-2-cyclohexylethyl)-3-methylbutyramide (Compound 210); $^1$H NMR (CDCl$_3$): 7.9 (t, J=3, 6 Hz, 1H), 6.3 (d, J=6 Hz, 1H), 4.6 (m, 1H), 4.1 (m, 2H), 2.3–0.8 (m, 22H); MS:m/e=293.73;

N-(2-benzylsulfanyl-1R-cyanomethylcarbamoylethyl)-1H-indole-5-carboxamide (Compound 211); $^1$H NMR (CD$_3$OD): 8.12 (s, 1H), 7.61 (d, J=7.7 Hz, 1H), 7.39 (d, J=8.4 Hz, 1H), 7.28 (m, 6H), 7.22 (m, 1H), 7.16 (m, 1H), 6.52 (m, 1H), 4.73 (m, 1H), 4.14 (s, 2H), 3.75 (s, 1H), 2.97 (m, 1H), 2.79 (m, 1H); MS (393.2);

N-(2-benzylsulfanyl-1R-cyanomethylcarbamoylethyl)-3-phenoxybenzamide (Compound 212); $^1$H NMR (CDCl$_3$): 7.55 (m, 1H), 7.45 (m, 1H), 7.39 (m, 1H), 7.26 (m, 6H), 7.12 (m, 3H), 6.97 (m, 2H), 4.67 (m, 1H), 4.11 (d, J=3.7 Hz, 2H), 3.72 (d, J=3.7 Hz, 2H), 2.93 (m, 1H), 2.73 (m, 1H); MS (446.4);

tert-butyl 3-(2-benzylsulfanyl-1R-cyanomethylcarbamoylethylcarbamoyl)benzylcarbamate (Compound 213); $^1$H NMR (CDCl$_3$): 7.69 (s, 1H), 7.62 (m, 1H), 7.48 (d, J=7.2 Hz, 1H), 7.41 (d, J=7.48 Hz, 1H), 7.28 (m, 4H), 7.12 (J=7.2 Hz, 1H), 4.74 (dd, J=13.5, 6.9 Hz, 1H), 4.33 (s, 2H), 4.13 (d, J=5.4 Hz, 2H), 3.77 (s, 2H), 3.01 (dd, J=14.4, 6.3 Hz, 1H), 2.85 (dd, J=13.8, 7.2 Hz, 1H), 1.45 (s, 9H); MS (483);

3-acetyl-N-(2-benzylsulfanyl-1R-cyanomethylcarbamoylethyl)benzamide (Compound 214); $^1$H NMR (CDCl$_3$): 8.348 (1H), 8.11 (d, J=6.6 Hz, 1H), 7.95 (d, J=6.2 Hz, 1H), 7.56 (m, 1H), 7.14–7.54 (m, 7H), 4.73 (m, 1H), 4.16 (d, J=5.9 Hz, 2H), 3.80 (m, 2H), 3.08 (dd, J=13.9, 7.3 Hz, 1H), 2.87 (dd, J=13.9,6.2 Hz, 1H), 2.64 (s, 3H); MS (396.0);

3-(3-methylbenzoylamino-N-(2-benzylsulfanyl-1R-cyanomethylcarbamoylethyl)benzamide (Compound 215); $^1$H NMR (CDCl$_3$): 8.12 (s, 1H), 7.95 (m, 2H), 7.70 (s, 1H), 7.66 (m, 1H), 7.20–7.47 (m, 8H), 7.12 (d, J=6.9 Hz, 1H), 4.74 (m, 1H), 4.16 (d, J=5.7 Hz, 2H), 3.77 (s, 2H), 3.01 (dd, J=13.7, 5.9 Hz, 1H), 2.86 (dd, J=13.8, 6.8 Hz, 1H), 2.42 (s, 3H); MS: (487.4);

N-[(cyanomethylcarbamoyl)(propoxy)methyl]benzamide (Compound 216); $^1$H NMR (DMSO): 9.25 (d, J=10 Hz, 1H), 8.65 (t, J=6 Hz, 1H), 7.92 (d, J=7 Hz, 2H), 7.5 (m, 3H), 5.60 (d, J=10 Hz, 1H), 4.18 (m, 2H), 3.51 (m, 2H), 1.56 (h, J,=8 Hz, 2H), 0.88 (t, J=8 Hz, 3H);

N-(3-benzylsulfanyl-1R-cyanomethylcarbamoylpropyl)benzamide (Compound 217); $^1$H NMR (DMSO): 8.69 (t, J=6 Hz, 1H), 8.63 (d, J=8 Hz, 1H), 7.90 (d, J=9 Hz, 2H), 7.5 (m, 3H), 7.2 (m, 5H), 4.54 (m, 1H), 4.13 (d, J=6 Hz, 2H), 3.73 (s, 2H), 2.46 (m, 2H), 2.02 (m, 2H); MS: m/e=367.81;

N-[(cyanomethylcarbamoyl)(cyclohexyloxy)methyl]benzamide (Compound 218); $^1$H NMR (DMSO): 9.26 (d, J=9 Hz, 1H), 8.55 (t, J=6 Hz, 1H), 7.92 (d, J=7 Hz, 2H), 7.51 (m, 3H), 5.72 (d, J=10 Hz, 1H), 4.17 (m, 2H), 3.56 (m, 1H), 1.95 (m, 3H), 1.3 (m, 6H); MS: m/e=315.8;

N-(1S-cyanomethylcarbamoyl-2-cyclohexylethyl)succinamic acid (Compound 219); $^1$H NMR (CDCl$_3$): 4.38 (m, 1H), 4.05 (s, 2H), 2.45 (d, J=6.3 Hz, 2H), 2.58 (d, J=6.3 Hz, 2H), 0.8–1.9 (m, 15H); MS: m/e (+) 309.72;

3-[3-(2-chloro-6-methylphenyl)ureidol-N-(1S-cyanomethylcarbamoyl-2-cyclohexylethyl]benzamide (Compound 220);

tert-butyl 4-(1S-cyanomethylcarbamoyl-2-cyclohexylethylcarbamoyl)phenylcarbamate (Compound 221);

N-(1S-cyanomethylcarbamoyl-2-pyrid-4-ylethyl)benzamide (Compound 222); $^1$H NMR: (CDCl$_3$) 8.36 (d, J=6 Hz, 2H), 7.80 (d, J=6.5 Hz, 1H), 7.66 (d, J=7.3 Hz, 2H), 7.47–7.32 (m, 4H), 7.14 (d, J=6 Hz, 2H), 4.79 (m, 1H), 4.06 (d, J=17 Hz, 1H), 3.94 (d, J=17 Hz, 1H), 3.15 (dd, J=6.6 Hz, J=13.6 Hz, 1H), 3.01 (dd, J=7.5 Hz, J=14 Hz, 1H); (M$^{30}$+1) 309;

N-[1S-cyanomethylcarbamoyl-2-(4-oxocyclohexyl)ethyl]benzamide (Compound 223); $^1$H NMR: (CDCl$_3$) 7.93 (m, 1H), 7.81 (d, J=7 Hz, 2H), 7.59–7.44 (m, 3H), 7.13 (t, J=8 Hz, 1H), 4.85 (m, 1H), 4.23–4.08 (m, 2H), 2.38–1.25 (m, 11H); MS: (M$^+$+1) 328;

N-[1S-cyanomethylcarbamoyl-2-(4,4-difluorocyclohexyl)ethyl]benzamide (Compound 224); $^1$H NMR: (CDCl$_3$) 8.04 (m, 1H), 7.80 (d, J=7.4 Hz, 2H), 7.58–7.42 (m, 3H), 7.20 (d, J=6 Hz, 1H), 4.84 (m, 1H), 4.21–4.03 (m, 2H), 2.20–1.23 (m, 11H); MS: (M$^+$+1) 350;

N-[1S-cyanomethylcarbamoyl-2-cyclohexylethyl]thiomorpholine-4-carboxamide (Compound 225); $^1$H NMR (DMSO): 7.75 (m, 1H), 4.99 (m, 1H), 4.37 (m, 1H), 4.12 (m, 1H), 3.7 (m, 4H), 2.61 (m, 4H), 2–0.8 (m, 13H); MS: m/e 339.4;

4-(1S-cyanomethylcarbamoyl-2-cyclohexylethylcarbamoyl)butyric acid (Compound 226);

N-[(cyanomethylcarbamoyl)(phenethyloxy)methyl]benzamide (Compound 227); $^1$H NMR (DMSO): 9.30 (d, J=9 Hz, 1H), 8.69 (t, J=7 Hz, 1H), 7.90 (d, J=8 Hz, 2H), 7.51 (m, 3H), 7.2 (m, 5H), 5.66 (m, 1H), 4.19 (m, 2H), 3.77 (m, 2H), 2.92 (m, 2H); MS: m/e=337.94;

4-amino-N-(1S-cyanomethylcarbamoyl-2-cyclohexylethyl)benzamide (Compound 228);

tert-butyl 4-(2-benzylsulfanyl-1R-cyanomethylcarbamoylethylcarbamoyl)piperazine-1-carboxylate (Compound 229); $^1$H NMR (CDCl$_3$): 7.46 (t, J=5.7 Hz, 1H), 7.31 (m, 5H), 5.27 (d, J=6.9 Hz, 1H), 4.38 (dd, J=13.4, 6.7 Hz, 1H), 4.15 (dd, J=17.3, 5.9 Hz, 1H), 4.06 (dd, J=17.3, 9.9 Hz, 1H), 3.73 (s, 2H), 3.42 (t, J=4.9 Hz, 4H), 3.31 (t, J=49 Hz, 4H), 4.06 (dd, J=14.1, 6.7 Hz, 1H), 2.77 (dd, J=13.9, 6.7 Hz, 1H), 1.46 (s, 9H); MS (462.4);

N-(2-benzylsulfanyl-1R-cyanomethylcarbamoylethyl)-4-fur-2-ylcarbonylpiperazine-1-carboxamide (Compound 230); $^1$H NMR (CDCl$_3$): 7.59 (t, J=5.7 Hz, 1H), 7.50 (dd, J=2.2, 1.0 Hz, 1H), 7.30 (m, 5H), 7.05 (dd, J=2.4,0.7 Hz, 1H), 6.50 (dd, J=6.9, 1.7 Hz, 1H), 5.42 (d, J=6.9 Hz, 1H), 4.42 (dd, J=13.3, 6.7 Hz, 1H), 4.15 (dd, J=11.6, 5.9 Hz, 1H), 4.06 (dd, J=16.2, 7.2 Hz, 1H), 3.73 (s, 4H), 3.45 (m, 4H), 3.38 (m, 4H), 2.95 (dd, J=13.9, 6.4 Hz, 1H), 2.78 (dd, J=13.9, 6.7 Hz, 1H); MS (456.2);

ethyl 4-(2-benzylsulfanyl-1R-cyanomethylcarbamoylethylcarbamoyl)piperazine-1-carboxylate (Compound 231); $^1$H NMR (CDCl$_3$): 7.58 (t, J=5.7 Hz, 1H), 7.30 (m, 5H), 5.35 (d, J=6.9 Hz, 1H), 4.41 (dd, J=13.3, 6.7 Hz, 1H), 4.15 (q, J=7.1 Hz, 2H), 4.10 (t, J=5.9 Hz, 2H), 3.72 (s, 2H), 3.47 (t, J=4.9 Hz, 4H), 3.34 (t, J=3.7 Hz, 4H), 2.93 (dd, J=13.8, 6.4 Hz, 1H), 2.76 (dd, J=13.8, 6.9 Hz, 1H), 1.26 (t, J=7.1 Hz, 3H); MS (434.4);

N-(2-benzylsulfanyl-1R-cyanomethylcarbamoylethyl)-4-hydroxybenzamide (Compound 232);

N-(2-benzylsulfanyl-1R-cyanomethylcarbamoylethyl)-3-hydroxybenzamide (Compound 233);

N-[2-(1-acetylpiperidin-4-yl)-1S-cyanomethylcarbamoylethyl]benzamide (Compound 234); MS: (M$^+$+Na) 379;

N-[(cyanomethylcarbamoyl)(phenylamino)methyl]benzamide (Compound 235); $^1$H NMR (DMSO): 9.02 (d, J=9 Hz, 1H), 8.91 (t, J=6 Hz, 1H), 7.86 (d, J=10 Hz, 2H), 7.5 (m, 3H), 7.11 (t, J=9 Hz, 2H), 6.78 (d, J=8 Hz, 2H), 6.65 (t, J=8 Hz, 1H), 6.08 (d, J=9 Hz, 1H), 5.87 (m, 1H), 4.20 (t, J=3 Hz, 2H); MS: m/e=308.99;

N-[1S-cyanomethylcarbamoyl-2-(4-methylenecyclohexyl)ethyl]benzamide (Compound 236); $^1$H NMR: (CDCl$_3$) 7.81–7.75 (m, 3H), 7.58–7.43 (m, 3H), 6.88 (d, J=8 Hz, 1H), 4.80 (m, 1H), 4.59 (s, 2H), 4.20 (dd, J=6 Hz, J=17 Hz, 1H), 4.08 (d, J=5.5 Hz, J=17 Hz, 1H), 2.30–1.48 (m, 9H), 1.15–0.96 (m, 2H); MS: (M$^+$+Na) 348;

N-[1S-cyanomethylcarbamoyl-2-(4-ethylidenecyclohexyl)ethyl]benzamide (Compound 237); $^1$H NMR: (CDCl$_3$) 7.87 (t, J=6 Hz, 1H), 7.80 (d, J=7 Hz, 2H), 7.58–7.43 (m, 3H), 6.94 (d, J=8 Hz, 1H), 5.12 (q, J=6.5 Hz, 1H), 4.80 (m, 1H), 4.20 (dd, J=6 Hz, J=17 Hz, 1H), 4.08 (dd, J=5.5 Hz, J=17 Hz, 1H), 2.55 (m, 1H), 2.17–1.50 (m, 8H), 1.53 (d, J=6.5 Hz, 3H), 1.10–0.91 (m, 2H); MS: (M$^+$+Na) 362;

N-[1S-cyanomethylcarbamoyl-2-(4-propylidenecyclohexyl)ethyl]benzamide (Compound 238); $^1$H NMR: (CDCl$_3$) 8.15 (m, 1H), 7.81 (d, J=8 Hz, 2H), 7.56–7.41 (m, 3H), 7.22 (d, J=7 Hz, 1H), 5.05 (t, J=7.2 Hz, 1H), 4.84 (q, J=7 Hz, 1H), 4.18 (dd, J=6 Hz, J=17 Hz, 1H), 4.05 (dd, J=5.5 Hz, J=17 Hz, 1H), 2.48 (m, 2H), 2.11–1.47 (m, 9H), 1.03–0.90 (m, 2H), 0.90 (t, J=7.7 Hz, 3H); MS: (M$^+$+Na) 376;

N-[1S-cyanomethylcarbamoyl-2-(1-ethylpiperidin-4-yl)ethyl]benzamide (Compound 239); $^1$H NMR: (DMSO) 8.68 (t, J=6 Hz, 1H), 8.56 (d, J=7 Hz, 1H), 7.87 (d, J=7 Hz, 2H), 7.54–7.42 (m, 3H), 4.50 (m, 1H), 4.10 (m, 2H), 2.77 (m, 2H), 2.24 (m, 2H), 1.79–1.05 (m, 9H), 0.93 (t, J=7 Hz, 3H); MS: (M$^+$+1) 343;

4-[2-benzoylamino-2S-cyanomethylcarbamoylethyl]-1-methylcyclohexyl trifluoroacetate (Compound 240); $^1$H NMR: (CDCl$_3$) 8.25 (t, J=5 Hz, 1H), 7.80 (d, J=7 Hz, 2H), 7.58–7.39 (m, 4H), 4.86 (q, J=7.5 Hz, 1H), 4.16 (dd, J=5.5 Hz, J=17 Hz, 1H), 4.04 (dd, J=5.5 Hz, J=17 Hz, 1H), 2.28 (m, 2H), 1.84–1.07 (m, 9H), 1.51 (s, 3H); MS: (M$^+$+1) 440;

N-(2-tert-butyldisulfanyl-1R-cyanomethylcarbamoylethyl)benzamide (Compound 241); $^1$H NMR (CDCl$_3$): 7.83 (m, 1H), 7.65 (m, 1H), 7.55 (m, 1H), 7.43 (m, 2H), 7.16 (m, 1H), 5.00 (m, 1H), 4.19 (m, 2H), 3.33 (m, 1H), 3.27 (m, 1H), 1.34 (s, 9H);

N-[1S-cyanomethylcarbamoyl-2-(4-hydroxycyclohexyl)ethyl]benzamide (Compound 242); $^1$H NMR: (CDCl$_3$+10% CD$_3$OD) 7.75 (d, J=7 Hz, 2H), 7.54–7.35 (m, 3H), 4.60 (m, 1H), 4.14 (d, J=17.5 Hz, 1H), 4.00 (d, J=17.3 Hz, 1H), 3.44 (M, 1H), 1.91–1.60 (m, 6H), 1.28–0.90 (m, 5H); MS: (M$^+$+Na) 352;

cis-4-(2-benzoylamino-2S-cyanomethylcarbamoylethyl)cyclohexyl acetate (Compound 243); MS: (M$^+$+Na) 394, (M$^+$—CH$_3$COO) 312;

N-[(cyanomethylcarbamoyl)(phenethylsulfanyl)methyl]benzamide (Compound 244); $^1$H NMR (DMSO): 9.14 (d, J=10 Hz, 1H), 9.01 (t, J=7 Hz, 1H), 7.94 (d, J=9 Hz, 2H), 7.5 (m, 3H), 7.2 (m, 5H), 5.88 (d, J=10 Hz, 1H), 4.22 (m, 2H), 2.90 (m, 4H); MS: m/e=354.01;

N-[1S-cyanomethylcarbamoyl-2-(1-thiazol-2-ylpiperidin-4-yl)ethyl]benzamide (Compound 245); $^1$NMR: (CDCl$_3$+10% CD$_3$OD) 7.77 (d, J=7 Hz, 2H), 7.51–7.37 (m, 3H), 7.06 (d, J=3.6 Hz, 1H), 6.48 (d, J=3.6 Hz, 1H), 4.68 (t, J=7.3 Hz, 1H), 4.14 (d, J=17.3 Hz, 1H), 4.01 (d, J=17.3 Hz, 1H), 3.91–3.85 (m, 2H), 2.99–2.89 (m, 2H), 1.90–1.27 (m, 7H); MS: (M$^+$+Na) 420;

N-[(cyanomethylcarbamoyl)(cyclohexylsulfanyl)methyl]benzamide (Compound 246); $^1$H NMR (DMSO): 9.10 (d, J=10 Hz, 1H), 8.94 (t, J=6 Hz, 1H), 7.92 (d, J=9 Hz, 2H), 7.50 (m, 3H), 5.80 (d, J=10 Hz, 1H), 4.19 (d, J=6 Hz, 2H), 2.96 (m, 1H), 2.00 (m, 1H), 1.88 (m, 1H), 1.67 (m 2H), 1.53 (m, 1H), 1.27 (m 5H); MS: m/e=331.98;

N-cyanomethyl-3-cyclohexyl-2R-(2-ethoxyacetylamino)propionamide (Compound 247);

N-(1S-cyanomethylcarbamoyl-2-cyclohexylethyl)-3-methoxypropionamide (Compound 248); $^1$H NMR (CDCl$_3$): 7.68 (t, J=5.4 Hz, 1H), δ .66 (d, J=7.9 Hz, 1H), 4.52 (dd, J=9.4, 13.4 Hz, 1H), 4.18 (dd, J=5.9, 17.6 Hz, 1H), 4.06 (dd, J=5.9, 17.6 Hz, 1H), 3.65 (m, 2H), 3.38 (s, 3H), 2.50 (t, J=5.7 Hz, 2H), 0.8–1.70 (m, 13H);

cis-N-[1S-cyanomethylcarbamoyl-2-(4-methoxycyclohexyl)ethyl]benzamide (Compound 249); $^1$H NMR: (CDCl$_3$) 8.01 (s, 1H), 7.80 (d, J=7 Hz, 2H), 7.55–7.42 (m, 3H), 6.84 (d, J=8.3 Hz, 1H), 5.26 (m, 1H), 4.59 (d, J=17.2 Hz, 1H), 4.14 (d, J=17.2 Hz, 1H), 3.54 (m, 1H), 3.29 (s, 3H), 2.18–0.94 (m, 11H); MS: (M$^+$+Na) 366;

N-(2-benzylsulfanyl-1R-cyanomethylcarbamoylethyl)-3-[3-(1-benzylprrolidin-3R-yl)-3-methylureido]benzamide (Compound 250); ESI-MS m/z 585.3 (M+H$^+$);

N-(2-benzylsulfanyl-1R-cyanomethylcarbamoylethyl)-3-[3-(1-benzylpyrrolidin-3S-yl)-3-methylureido]benzamide (Compound 251); ESI-MS m/z 585.4 (M+H$^+$);

N-(2-benzylsulfanyl-1R-cyanomethylcarbamoylethyl)-3-[3-(4-benzylpiperazin-1-ylcarbonyl)amino]benzamide (Compound 252); ESI-MS m/z 571.2 (M+H$^+$);

N-(1R-cyanomethylcarbamoyl-2-pentafluorobenzylsulfanylethyl)benzamide (Compound 253);

N-[1R-cyanomethylcarbamoyl-2-naphth-2-ylmethylsulfanylethyl)benzamide (Compound 254); $^1$H NMR (CDCl$_3$): 7.80 (m, 4H), 7.12–7.74 (m, 9H), 4.80 (m, 1H), 4.10 (m, 3H), 3.75 (s, 2H), 3.02 (m, 1H), 2.87 (m, 1H), 2.2–2.6 (m);

N-(2-benzylsulfanyl-1R-cyanomethylcarbamoylethyl)-3-(3-[1,3,4]thiadiazol-2-ylureido)benzamide (Compound 255); $^1$H NMR (270 MHz, DMSO-d$_6$) δ 2.78 (m, 1), 2.89 (m, 1), 3.79 (s, 2), 4.18 (d, 2), 4.71 (m, 1), 7.23–7.37 (m, 5), 7.45 (t, 1), 7.61 (d, 1), 7.71 (d, 1), 7.99 (s, 1), 8.75 (d, 1), 8.77 (t, 1), 9.08 (s, 1), 9.22 (s, 1); ESI-MS m/z 496.1 (M+H$^+$);

N-[2-(4-chlorobenzylsulfanyl)-1R-cyanomethylcarbamoylethyl]benzamide (Compound 256); $^1$H NMR: (DMSO) 8.85 (t, J=5 Hz, 1H), 8.73 (d, J=8.4 Hz, 1H), 7.92 (d, J=7 Hz, 2H), 7.60–7.47 (m, 3H), 7.40–7.33 (m, 4H), 4.69 (dd, J=5.2 Hz, J=9.4 Hz, 1H), 4.16 (s, 2H), 3.78 (s, 2H), 2.90 (dd, J=5.2 Hz, J=13.6 Hz, 1H), 2.77 (dd, J=9.6 Hz, J=13.8 Hz, 1H); MS: (M$^+$+1) 388/390;

N-[1R-cyanomethylcarbamoyl-2-(2-methylbenzylsulfanyl)ethyl]benzamide (Compound

257); ¹H NMR: (DMSO) 8.87 (t, J=5.4 Hz, 1H), 8.74 (d, J=8.2 Hz, 1H), 7.92 (d, J=7 Hz, 2H), 7.60–7.47 (m, 3H), 7.25–7.08 (m, 4H), 4.75 (m, 1H), 4.17 (d, J=5.7 Hz, 2H), 3.80 (s, 2H), 2.98 (dd, J=5.2 Hz, J=13.6 Hz, 1H), 2.82 (dd, J=9.6 Hz, J=13.8 Hz, 1H), 2.31 (s, 3H); MS: (M⁺+1) 368;

N-[1R-cyanomethylcarbamoyl-2-(3,5-dimethylbenzylsulfanyl)ethyl]benzamide (Compound 258); ¹H NMR: (DMSO) 8.86 (t, J=5.4 Hz, 1H), 8.73 (d, J=8.2 Hz, 1H), 7.93 (d, J=7 Hz, 2H), 7.60–7.46 (m, 3H), 6.91 (s, 2H), 6.85 (s, 1H), 4.71 (m, 1H), 4.17 (d, J=5.7 Hz, 2H), 3.70 (s, 2H), 2.92 (dd, J=5.4 Hz, J=13.6 Hz, 1H), 2.76 (d, J=9.6 Hz, J=13.8 Hz, 1H), 2.22 (s, 6H); MS: (M⁺+1) 382;

N-[1R-cyanomethylcarbamoyl-2-(4-trifluoromethylbenzylsulfanyl)ethyl]benzamide (Compound 259); ¹H NMR: (DMSO) 8.86 (t, J=5.4 Hz, 1H), 8.74 (d, J=7.9 Hz, 1H), 7.93 (d, J=7 Hz, 2H), 7.68 (d, J=8.2 Hz, 2H), 7.60–7.46 (m, 5H), 4.71 (m, 1H), 4.17 (d, 3.88 (s, 2H), 2.92 (dd, J=5.4 Hz, J=13.4 Hz, 1H), 2.79 (dd, J=9.6 Hz, J=13.8 Hz, 1H); MS: (M⁺+1) 422;

N-[1R-cyanomethylcarbamoyl-2-(4-trifluoromethoxybenzylsulfanyl)ethyl]benzamide (Compound 260); ¹H NMR: (DMSO) 8.86 (t, J=5.4 Hz, 1H), 8.74 (d, J=8.2 Hz, 1H), 7.93 (d, J=7 Hz, 2H), 7.60–7.42 (m, 5H), 7.31 (d, J=7.9 Hz, 2H), 4.71 (m, 1H), 4.17 (d, J=5.7 Hz, 2H), 3.83 (s, 2H), 2.92 (dd, J=5.4 Hz, J=13.8 Hz, 1H), 2.79 (dd, J=9.6 Hz, J=13.8 Hz, 1H); MS: (M⁺+1) 438;

N-[1R-cyanomethylcarbamoyl-2-(4-trifluoromethylsulfanylbenzylsulfanyl)ethyl]benzamide (Compound 261); ¹H NMR: (DMSO) 8.86 (t, J=5.4 Hz, 1H), 8.75 (d, J=8.2 Hz, 1H), 7.92 (d, J=7 Hz, 2H), 7.66 (d, J=7.9 Hz, 2H), 7.60–7.45 (m, 5H), 4.72 (m, 1H), 4.17 (d, J=5.7 Hz, 2H), 3.86 (s, 2H), 2.92 (dd, J=5.4 Hz, J=13.8 Hz, 1H), 2.80 (dd, J=9.6 Hz, J=13.8 Hz, 1H); MS: (M⁺+1) 454;

N-[1R-cyanomethylcarbamoyl-2-(3-nitrobenzylsulfanyl)ethyl]benzamide (Compound 262); ¹H NMR: (DMSO) 8.83 (t, J=5 Hz, 1H), 8.73 (d, J=7.7 Hz, 1H), 8.21 (s, 1H), 8.09 (d, J=8 Hz, 1H), 7.99 (m, 2H), 7.79 (d, J=7.7 Hz, 1H), 7.63–7.45 (m, 4H), 4.66 (m, 1H), 4.14 (d, J=5 Hz, 2H), 3.94 (s, 2H), 2.90–2.49 (m, 2H); MS: (M⁺+1) 399.2;

N-[1R-cyanomethylcarbamoyl-2-(3-nitrobenzylsulfanyl)ethyl]benzamide (Compound 263); ¹H NMR (DMSO): 8.79 (m, 1H), 8.48 (d, J=5 Hz, 1H), 7.93 (d, J=7 Hz, 2H), 7.75 (dt, J=2, 8 Hz, 1H), 7.52 (m, 5H), 7.26 (m, 1H), 4.71 (m, 1H), 4.15 (m. 2H), 3.88 (s, 2H), 2.89 (m, 2H); MS: m/e=354.97;

N-(1R-cyanomethylcarbamoyl-2-pyrid-3-ylmethylsulfanylethyl)benzamide (Compound 264); ¹H NMR (DMSO): 8.86 (t, J=6 Hz, 1H), 8.74 (d, J=9 Hz, 1H), 8.53 (d, J=2Hz, 1H), 8.44 (dd, J=5, 2Hz, 1H), 7.91 (m, 2H), 7.74 (m, 1H), 7.54 (m, 3H), 7.34 (m, 1H), 4.72 (m, 1H), 4.17 (m, 2H), 3.82 (s, 2H), 2.84 (m, 2H); MS: m/e=355.04;

N-(1R-cyanomethylcarbamoyl-2-pyrid-4-ylmethylsulfanyl)ethyl]benzamide (Compound 265); ¹H NMR (DMSO): 8.85 (t, J=6 Hz, 1H), 8.75 (d, J=9 Hz, 1H), 8.5 (m, 2H), 7.93 (m, 2H), 7.54 (m, 3H), 7.35 (m, 2H), 4.69 (m, 1H), 4.16 (d, J=6 Hz, 2H), 3.8 (s=2H), 2.91 (dd, J=6, 15 Hz, 1H), 2.79 (dd, J=10, 15 Hz, 1H); MS: m/e=355.02;

3-amino-N-(1S-cyanomethylcarbamoyl)-2-cyclohexylethylbenzamide (Compound 266);

3-amino-N-(2-benzylsulfanyl-1R-cyanomethylcarbamoylethyl)benzamide (Compound 267);

3-amino-N-(1S-cyanomethylcarbamoylpentyl)benzamide (Compound 268); methyl 2S-benzoylamino-3-cyclohexylpropionylaminocyanoacetate (Compound 269); MS: (M⁺+Na) 394;

2S-benzoylamino-3-cyclohexylpropionylaminocyanoacetic acid (Compound 270); MS: (M⁺+1) 358;

N-[1R-cyanomethylcarbamoyl-2-(3,4-dichlorobenzylsulfanyl)ethyl]benzamide (Compound 271); ¹H NMR (DMSO): 8.8 (d,t, 2H), 7.9 (d, J=8 Hz, 2H), 7.8 (m, 3H),7.1 (m, 4H), 4.7 (m, 1H), 4.2 (S, 2H), 3.7 (s, 2H), 2.9 (m, 1H), 2.7 (m, 1H), 2.3 (s, 3H); MS:m/e=368.0;

N-[1R-cyanomethylcarbamoyl-2-(3-methylbenzylsulfanyl)ethyl]benzamide (Compound 272);

N-[1R-cyanomethylcarbamoyl-2-(4-nitrobenzylsulfanyl)ethyl]benzamide (Compound 273); ¹H NMR: (DMSO) 8.83 (t, J=5.1 Hz, 1H), 8.72 (d, J=7.7 Hz, 1H), 8.17 (d, J=8 Hz, 2H), 7.89 (d, J=7 Hz, 2H), 7.62–7.45 (m, 5H), 4.67 (m, 1H), 4.15 (d, J=5.4 Hz, 2H), 3.92 (s, 2H), 2.89 (dd, J=5.4 Hz, J=13.8 Hz, 1H), 2.77 (dd, J=9.6 Hz, J=13.8 Hz, 1H); MS: (M⁺+1) 399.2;

N-[1R-cyanomethylcarbamoyl-2-(2-nitrobenzylsulfanyl)ethyl]benzamide (Compound 274); ¹H NMR (CDCl₃): 8.81 (m, 1H), 8.79 (d, J=8.0 Hz, 1H), 7.95 (d, J=3.9 Hz, 1H), 7.84 (m, 2H), 7.42–7.65 (m, 6H), 4.63 (m, 1H), 4.05 (m, 1H), 3.80 (m, 2H); MS: m/e (+1) 399.2;

N-[1R-cyanomethylcarbamoyl-2-(3-trifluoromethylbenzylsulfanyl)ethyl]benzamide (Compound 275); ¹H NMR (DMSO): 8.86 (m, 1H), 8.74 (d, J=4.9 Hz, 1H), 7.90 (d, J=8.4 Hz, 2H), 4.72 (m, 1H), 4.15 (d, J=5.1 Hz, 2H), 3.88 (s, 2H), 2.78 (m, 2H), 2.22–2.74 (m, 7H); MS: m/e (+1) 422.2;

N-[1R-cyanomethylcarbamoyl-2-(3-trifluoromethylbenzylsulfanyl)ethyl]benzamide (Compound 276); ¹H NMR (DMSO): 8.81 (m, 1H), 8.76 (d, J=4.8 Hz, 1H), 7.85 (d, J=8.4 Hz, 2H), 7.10–7.55 (m, 7H), 4.7 (m, 1H), 4.15 (s, 2H), 3.80 (s, 2H), 2.80 (m, 2H); MS: m/e (+1) 438.2;

N-[1R-cyanomethylcarbamoyl-2-(2-methylbenzylsulfanyl)ethyl]morpholine-4-carboxamide (Compound 277); ¹H NMR (DMSO): 8.7 (t, J=6 Hz, 1H), 7.2 (m, 4H), 6.67 (d, J=7.8 Hz, 1H), 4.4 (m, 1H), 4.2 (s, 2H), 3.7 (s, 2H), 3.5 (t, 4H), 3.3 (t, 4H), 2.7 (m, 2H), 2.3 (s, 3H); MS m/e 377.2;

N-[1R-cyanomethylcarbamoyl-2-(2-nitrobenzylsulfanyl)ethyl]morpholine-4-carboxamide (Compound 278); ¹H NMR (DMSO): 8.67 (t, J=6 Hz, 1H), 7.97 (d, J=8.1 Hz, 1H), 7.5 (m, 4H), 4.28 (q, 1H), 4.1 (d, J=4 Hz, 2H), 4.05 (m, 2H), 3.5 (t, 4h), 3.2 (t, 4H), 2.6 (m, 2H); MS m/e 408.4;

N-[1R-cyanomethylcarbamoyl-2-(3-nitrobenzylsulfanyl)ethyl]morpholine-4-carboxamide (Compound 279); ¹H NMR (DMSO): 8.7 (t, J=3 Hz, 1H), 8.2 (m, 2H), 7.7 (m, 2H), 6.77 (d, J=3 Hz, 1H), 4.33 (m, 1H), 4.16 (m, 2H), 3.85 (d, J=2.4 Hz, 2h), 3.4 (m, 8H), 2.6 (m, 2H); MS m/e 408;

N-(1S-cyanomethylcarbamoyl-2-cyclohexylethyl)-1,1-dioxo-1λ⁶-thiomorpholine-4-carboxamide (Compound 280); ¹H NMR (DMSO): 8.5 (t, J=3 Hz, 1H), 6.9 (d, J=3 Hz, 1H), 4.11 (m, 3H), 3.8 (t, 4H), 3.1 (t, 4H), 1.8–0.8 (m, 13H); MS m/e 370.8;

N-(2-allylsulfanyl-1S-cyanomethylcarbamoylethyl) benzamide (Compound 281); $^1$H NMR (DMSO): 8.72 (t, 1H), 8.65 (d, J=3 Hz, 1H), 7.9 (d, 2H), 7.5 (m, 3H), 5.7 (m, 1H), 5.1 (m, 2H), 4.1 (d, J=3 Hz, 2H), 2.8 (m, 2H); MS m/e 304.2;

N-[1R-cyanomethylcarbamoyl)-2-(2-fluorobenzylsulfanyl)ethyl]benzamide (Compound 282); $^1$H NMR (DMSO): 8.85 (m, 1H), 8.72 (d, J=4.9 Hz, 1H), 7.90 (d, J=8.3 Hz, 2H), 7.10–7.63 (m, 7H), 4.62 (m, 1H), 4.08 (d, J=5.0 Hz, 2H), 3.89 (s, 2H), 2.88 (m, 2H); MS: m/e (+1) 369.8;

N-[2-(2-chlorobenzylsulfanyl)-1R-cyanomethylcarbamoylethyl]benzamide (Compound 283); $^1$H NMR (DMSO): 8.80 (m, 1H), 8.75 (d, J=4.8, 1H), 7.95 (d, J=8.2 Hz, 2H), 7.12–7.58 (m, 7H), 4.75 (m, 1H), 4.18 (d, J=4.8 Hz, 2H), 3.85 (s, 2H), 2.8 (m, 2H); MS: m/e (+1) 388.2;

N-[2-(2-bromobenzylsulfanyl)-1R-cyanomethylcarbamoylethyl]benzamide (Compound 284); $^1$H NMR (DMSO): 8.85 (m, 1H), 8.73 (d, J=4.8 Hz, 1H), 7.95 (d, J=8.2 Hz, 2H), 7.4–7.65 (m, 5H), 7.37 (t, J=7.2 Hz, 1H), 7.20 (t, J=7.2 Hz, 1H), 4.70 (m, 1H), 4.08 (d, J=5.1 Hz, 2H), 3.90 (s, 2H), 2.90 (m, 2H); MS: m/e (+1) 434.0;

N-[1R-cyanomethylcarbamoyl-2-(2-iodobenzylsulfanyl) ethyl]benzamide (Compound 285); $^1$H NMR (DMSO): 8.86 (m, 1H), 8.74 (d, J=8.1 Hz, 1H), 7.9 (d, J=8.4 Hz, 2H), 7.83 (d, J=7.6 Hz, 5H), 7.40–7.60 (m, 4H), 7.33 (t, J=7.7 Hz, 1H), 6.99 (t, J=7.4 Hz, 1H), 4.71 (m, 1H), 4.16 (d, J=5.5 Hz, 2H), 3.83 (s, 2H), 2.88 (m, 2H); MS: m/e (+1) 480.0;

N-[2-(4-tert-butyl-benzylsulfanyl)-1R-cyanomethylcarbamoylethyl]benzamide (Compound 286); $^1$H NMR (CDCl$_3$): 8.16 (m, 1H), 7.79 (d, J=7.2 Hz, 2H), 7.51 (t, J=7.3 Hz, 2H), 7.40 (t, J=8.0 Hz, 2H), 7.19–7.29 (m, 4H), 4.98 (m, 1H), 4.08 (m, 2H), 3.72 (m, 2H), 2.94 (m, 2H);

N-[3-(2-chlorophenylsulfanyl)-1R-cyanomethylcarbamoylpropyl]benzamide (Compound 287); $^1$H NMR (DMSO): 8.73 (m, 2H), 7.92 (m, 2H), 7.38–7.56 (m, 5H), 7.32 (t, J=5.9 Hz, 1H), 7.18 (t, J=5.9 Hz, 1H), 4.64 (m, 1H), 4.14 (d, J=5.8 Hz, 2H), 3.07 (m, 2H), 2.12 (m, 2H); MS:m/e (+1)=385.9;

N-(1R-cyanomethylcarbamoyl-3-o-tolylsulfanylpropyl) benzamide (Compound 288); $^1$H NMR (DMSO): 8.70 (m, 2H), 7.92 (m, 2H), 7.45–7.60 (m, 3H), 7.30 (d, J=13.3 Hz, 1H), 7.05–7.21 (m, 3H), 4.61 (dd, J=7.7 Hz, 1H), 4.13 (d, J=5.4 Hz, 2H), 3 (m, 2H), 2.28 (s, 3H), 2.10 (m, 2H); MS:m/e (+1)=366.0;

N-(1R-cyanomethylcarbamoyl-3-pyrid-2-ylsulfanylpropyl)benzamide (Compound 289); $^1$H NMR (DMSO): 8.70 (m, 2H), 8.39 (m, 1H), 7.95 (d, J=13.5, 2H), 7.45–7.68 (m, 4H), 7.29 (d, J=13.5 Hz, 1H), 7.10 (m, 1H), 4.59 (m, 1H), 4.13 (d, J=5.7 Hz, 2H), 3.20 (m, 2H), 2.14 (m, 2H); MS:m/e (+1)=353.0;

tert-butyl 4-(1R-cyanomethylcarbamoyl-2-pyrid-2-ylmethylsulfanylethylcarbamoyl)piperidine-1-carboxylate (Compound 290); $^1$H NMR (DMSO): 8.72 (t, J=6.5 Hz, 1H), 8.48 (d, J=5.2 Hz, 1H), 8.21 (d, J=11.8 Hz, 1H), 7.75 (t, J=6.5 Hz, 1H), 7.38 (d, J=7.9 Hz, 1H), 7.25 (m, 1H), 4.80 (m, 1H), 4.14 (d, J=6.6 Hz, 2H), 3.93 (d, J=13.6 Hz, 2H), 3.85 (s, 2H), 3.33 (s, 4H), 2.56–2.83 (m, 4H), 2.35 (m, 1H), 1.35 (s, 9H); MS:m/e (+1)=461.4;

N-(1R-cyanomethylcarbamoyl-3-pyrid-4-ylsulfanylpropyl)benzamide (Compound 291); $^1$H NMR (DMSO): 8.73 (m, 2H), 8.35 (d, J=6.2 Hz, 2H), 7.95 (m, 2H), 7.51 (m, 3H), 7.28 (d, J=6.2 Hz, 2H), 4.62 (q, J=7.9 Hz, 1H), 4.14 (d, J=5.7 Hz, 2H), 3.13 (m, 2H), 2.14 (m, 2H); MS:m/e (+1)=355.0;

N-[1-(Cyanomethyl-carbamoyl)-2-cycloheptyl-ethyl]-benzamide (Compound 292); and

2-Benzylamino-N-cyanomethyl-3-cyclohexyl-propionamide (Compound 293).

Example 11

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC(20 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity with a $K_i$ of less than or equal to 10 μM.

Example 12

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC(4 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity with a $K_i$ of less than or equal to 10 μM.

Example 13

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC(1 nMoles in 25 μL of assay buffer) was added to the assay solutions and hydrolysis was followed spectrophotometrically at (λ460 nm) for 5 minutes. Apparent inhibition constants ($K_i$)

were calculated from the enzyme progress curves using standard mathematical models.

Compounds of the invention were tested by the above-described assay and observed to exhibit cathepsin L inhibitory activity with a $K_i$ of less than or equal to 10 µM.

Example 14

Cathepsin S Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM). Human cathepsin S (0.158 pMoles in 25 µL of assay buffer) was added to the dilutions. The assay solutions were mixed for 5–10 seconds on a shaker plate, covered and incubated for 30 minutes at room temperature. Z-Val-Val-Arg-AMC(9 nMoles in 25 µL of assay buffer) was added to the assay solutions and hydrolysis was followed spectrophotometrically at (µ460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity with a $K_i$ of less than or equal to 10 µM.

Example 15

Ovalbumin Challenge Mouse

C57 mice (female) were sensitised with ovalbumin (10 µg, i.p.) administered together with aluminium hydroxide adjuvant (20 mg, i.p.) on days 0 and 12. Mice are challenged on either day 22, 23 or 24 by exposure for 60 minutes to an aerosol of ovalbumin (10 g/l) twice, 4 hours apart. Mice are dosed p.o. with either vehicle 5 ml/kg (0.5% MC/0.2% Tween 80 in H$_2$O) or test compound at 0, 8, 23.5 29, 33, 48 and 56 hours.

Mice were euthanized with pentobarbitone i.p. after 86 hours (72 hours after the first challenge). The lungs were insufflated for histological examination as soon as possible after euthanization. Lungs were insufflated with 10% neutral buffered formalin (NBF), at 30 cm water pressure. The lungs were removed and placed in pots of 10% NBF. After fixation in 10% NBF for a minimum of 24 hours the lungs were processed through graded alcohols to wax. The lungs were blocked longitudinally and one 2 µm section for each animal was cut at the level of the main bronchi. Sections then were stained with haematoxylin and eosin. Pathological assessment of sections is performed and a grading is assigned.

Histopathological evaluation of the lung tissue demonstrate a dose dependant anti-inflammatory effect on vascular and mucosal beds after treatment with compounds of the invention between 0.03 and 30 mg/kg.

Example 16

Representative Pharmaceutical Formulations Containing a Compound of Formula I

| ORAL FORMULATION | |
| --- | --- |
| Compound of Formula I | 10–100 mg |
| Citric Acid Monohydrate | 105 mg |

| -continued | |
| --- | --- |
| ORAL FORMULATION | |
| Sodium Hydroxide | 18 mg |
| Flavoring | |
| Water | q.s. to 100 mL |

| INTRAVENOUS FORMULATION | |
| --- | --- |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
| --- | --- |
| Compound of Formula I | 1% |
| Microcrystalline Cellulose | 73% |
| Stearic Acid | 25% |
| Colloidal Silica | 1%. |

We claim:
1. A compound of Formula (I):

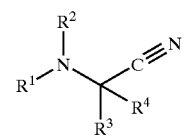

(I)

in which:
R$^1$ is a group of Formula (a):

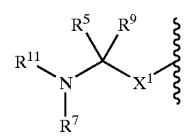

(a)

wherein:
X$^1$ is —C(O)— or —CH$_2$S(O)$_2$—;
R$^5$ is hydrogen;
R$^7$ is hydrogen;
R$^9$ is (C$_{1-6}$)alkyl substituted with —OR$^{14}$ or —SR$^{14}$, wherein R$^{14}$ is (C$_{3-6}$)cycloalkyl(C$_{0-6}$)alkyl, phenyl (C$_{0-6}$)alkyl, biphenylyl(C$_{0-6}$)alkyl or hetero(C$_{5-6}$) aryl(C$_{0-6}$)alkyl wherein within R$^9$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^3$NR$^{12}$R$^{12}$, —X$^3$NR$^{12}$C(O)OR$^{12}$, —X$^3$NR$^{12}$C(O)NR$^{12}$R$^{12}$, —X$^3$NR$^{12}$C(NR$^{12}$)NR$^{12}$R$^{12}$, —X$^3$OR$^{12}$, —X$^3$SR$^{12}$, —X$^3$C(O)OR$^{12}$, —X$^3$C(O)NR$^{12}$R$^{12}$, —X$^3$S(O)$_2$NR$^{12}$R$^{12}$, —X$^3$P(O)(OR$^3$)OR$^{12}$, —X$^3$OP(O)(OR$^3$)OR$^{12}$, —X$^3$OC(O)R$^{13}$, —X$^3$OC (O)R$^{13}$, —X$^3$NR$^{12}$C(O)R$^{13}$, —X$^3$S(O)R$^{13}$, —X$^3$S (O)$_2$R$^{13}$ and —X$^3$C(O)R$^{13}$, wherein X$^3$ is a bond or (C$_{1-6}$)alkylene, R$^{12}$ at each occurrence independently is hydrogen, $(C_{1-3})$alkyl or halo-substituted $(C_{1-3})$alkyl and $R^{13}$ is $(C_{1-3})$alkyl or halo-substituted $(C_{1-3})$alkyl; and $R^{11}$ is —$X^4X^5R^{18}$, wherein $X^4$ is —C(O)—, $X^5$ is a bond and $R^{18}$ is (i) $(C_{3-12})$cycloalkyl$(C_{0-6})$alkyl, hetero$(C_{3-12})$cycloalkyl$(C_{0-6})$alkyl, $(C_{6-12})$aryl$(C_{1-6})$alkyl or hetero$(C_{5-12})$aryl$(C_{0-6})$alkyl or (ii) phenyl $(C_{0-6})$alkyl or hetero$(C_{5-6})$aryl$(C_{0-6})$alkyl, wherein said phenyl or heteroaryl is substituted by —$X^9OR^{24}$, —$X^9C(O)R^{24}$, —$X^9C(O)OR^{24}$, —$X^9C(O)NR^{24}R^{25}$, —$X^9NR^{24}R^{25}$, —$X^9NR^{25}C(O)R^{24}$, —$X^9NR^{25}C(O)OR^{24}$, —$X^9NR^{25}C(O)NR^{24}R^{25}$ or —$X^9NR^{25}C(NR^{25})NR^{24}R^{25}$, wherein $X^9$ is a bond or $(C_{1-6})$alkylene, $R^{24}$ is phenyl$(C_{0-6})$alkyl or hetero $(C_{5-6})$aryl$(C_{0-6})$alkyl and $R^{25}$ is hydrogen or $(C_{1-6})$alkyl, wherein within $R^{11}$ any aromatic ring system present may be substituted further by 1 to 5 substituents independently selected from $(C_{1-6})$alkyl, halo, halo-substituted $(C_{1-4})$alkyl, —$OR^{12}$, —$X^3SR^{12}$, —$C(O)OR^{12}$ and —$X^3NR^{12}C(O)OR^{12}$ wherein $X^3$ is a bond or $(C_{1-6})$alkylene and $R^{12}$ is hydrogen or $(C_{1-6})$alkyl; and $R^2$ is hydrogen; and $R^3$ and $R^4$ are both hydrogen; and the N-oxide derivatives, prodrug derivatives, protected derivatives, individual isomers and mixtures of isomers; and the pharmaceutically acceptable salts thereof.

2. The compound of claim 1 in which within Formula (a) $R^9$ is phenylmethylsulfanylmethyl or phenylsulfanylethyl, wherein said phenyl may be substituted by 1 to 5 radicals independently selected from $(C_{1-4})$alkyl, cyano, halo, halo-substituted $(C_{1-4})$alkyl, nitro, —$OR^{12}$, —$SR^{12}$ and —$C(O)OR^{12}$, wherein $R^{12}$ is hydrogen, $(C_{1-3})$alkyl or halo-substituted $(C_{1-3})$alkyl and $R^{13}$ is $(C_{1-3})$alkyl or halo-substituted $(C_{1-3})$alkyl; and $R^{11}$ is benzoyl, furylcarbonyl, phenyloxybenzoyl, pyridylthienylcarbonyl, benzoylbenzoyl, thienylcarbonyl, morpholinylcarbonyl, phenylureidobenzoyl, cyclohexenylcarbonyl or piperazinylcarbonyl, wherein within $R^{11}$ any aromatic ring system present may be substituted further by 1 to 2 substituents independently selected from $(C_{1-6})$alkyl, tert-butoxycarbonylamino, tert-butoxycarbonylaminomethyl, bromo, chloro, ethoxy, fluoro, hydroxy, methoxy and methylsulfanyl; and the N-oxide derivatives, prodrug derivatives, protected derivatives, individual isomers and mixtures of isomers; and the pharmaceutically acceptable salts thereof.

3. The compound of claim 2 in which within Formula (a), $R^9$ is a group having the following formula:

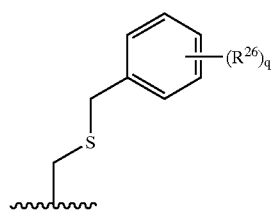

in which q is 0 to 5 and $R^{26}$ at each occurrence is independently selected from $(C_{1-4})$alkyl, cyano, halo, halo-substituted $(C_{1-4})$alkyl, nitro, —$OR^{12}$, —$SR^{12}$ and —$C(O)OR^{12}$, wherein $R^{12}$ is hydrogen, $(C_{1-3})$alkyl or halo-substituted $(C_{1-3})$alkyl and $R^{13}$ is $(C_{1-3})$alkyl or halo-substituted $(C_{1-3})$alkyl; and the N-oxide derivatives, prodrug derivatives, protected derivatives, individual isomers and mixtures of isomers; and the pharmaceutically acceptable salts thereof.

4. The compound of claim 1 in which within Formula (a), $R^9$ is benzylsulfanylmethyl, 2-bromobenzylsulfanylmethyl, 2-chlorobenzylsulfanylmethyl, 2-(2-chlorophenylsulfanyl) ethyl, 2-iodobenzylsulfanylmethyl, 2-methylbenzylsulfanylmethyl, or 2-nitrobenzylsulfanylmethyl and $R^{11}$ s 4-tert-butoxycarbonylaminobenzoyl, 3-tert-butoxycarbonylaminomethylbenzoyl, 2-(3,5-dimethoxyphenyl)thiazol-4-ylcarbonyl, fur-3-ylcarbonyl, 4-methoxybenzoyl, 3-methylbenzoyl, 3-phenoxybenzoyl, 5-pyrid-2-ylthien-2-ylcarbonyl, 3-benzoylbenzoyl, 4-methylbenzoyl, thien-2-ylcarbonyl, morpholin-4-ylcarbonyl, 5-bromothien-2-ylcarbonyl, 5-chlorothien-2-ylcarbonyl, 5-methylthien-2-ylcarbonyl, 2-(2-chloro-6-methylphenyl)ureidobenzoyl, cyclohex-1-en-1-ylcarbonyl, 3-ethoxybenzoyl, 3-fluorobenzoyl, 4-fluorobenzoyl or piperidin-1-ylcarbonyl; and the N-oxide derivatives, prodrug derivatives, protected derivatives, individual isomers and mixtures of isomers; and the pharmaceutically acceptable salts thereof.

5. The compound of claim 4 selected from the group consisting of:

N-(2-benzylsulfanyl-1R-cyanomethylcarbamoylethyl)-4-hydroxybenzamide;

N-[2-(2-bromobenzylsulfanyl)-1R-cyanomethylcarbamoylethyl]benzamide;

N-[1R-cyanomethylcarbamoyl-2-(2-iodobenzylsulfanyl) ethyl]benzamide;

N-[1R-cyanomethylcarbamoyl-2-(2-cyanobenzylsulfanyl)ethyl]morpholine-4-carboxamide;

N-[3-(2-chlorophenylsulfanyl)-1R-cyanomethylcarbamoylpropyl]benzamide;

N-[1R-cyanomethylcarbamoyl-2-(2-nitrobenzylsulfanyl) ethyl]morpholine-4-carboxamide N-[1R-cyanomethylcarbamoyl-2-(2-methylbenzylsulfanyl)ethyl]morpholine-4-carboxamide; and N-[1R-cyanomethylcarbamoyl-2-(2-methylbenzylsulfanyl)ethyl]benzamide; and the N-oxide derivatives, prodrug derivatives, protected derivatives, individual isomers and mixtures of isomers; and the pharmaceutically acceptable salts thereof.

6. A pharmaceutical composition comprising a compound of claim 1, or a N-oxide derivative, prodrug derivative, individual isomer, mixture of isomers, or a pharmaceutically acceptable salt thereof in admixture with one or more suitable excipients.

7. A method of treating a disease in an animal in which cysteine protease activity contributes to the pathology and/or symptomatology of the disease, which method comprises administering to the animal a therapeutically effective amount of a compound of claim 1; or a N-oxide derivative, prodrug derivative, individual isomer or mixture of isomers or a pharmaceutically acceptable salt thereof.

8. The method of claim 7 in which the cysteine protease is cathepsin S.

9. The method of claim 8 in which the disease is an autoimmune disorder, allergic disorder, allogeneic immune response, a disorder involving excessive elastolysis, cardiovascular disorders or a disorder involving fibril formation.

10. The method of claim 9 in which the disorder is selected from juvenile onset diabetes, multiple sclerosis, pemphigus vulgaris, Graves' disease, myasthenia gravis, systemic lupus erythemotasus, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture, atheroma and systemic amyloidosis.

11. A compound according to claim 1 in which $R^1$ is a group of Formula (a) wherein $X^1$ is —$CH_2S(O)_2$—; and the N-oxide derivatives, prodrug derivatives, protected derivatives, individual isomers and mixtures of isomers; and the pharmaceutically acceptable salts thereof.

12. A compound of Formula (II):

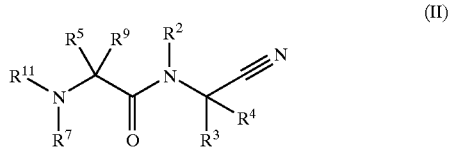

(II)

wherein:
$R^2$, $R^3$, $R^4$, $R^5$ and $R^7$ are hydrogen;
$R^9$ represents benzyloxymethyl, benzylsulfanylethyl, benzylsulfanylmethyl, benzylsulfinylmethyl, phenoxyethyl, pyridylsulfanylethyl, or phenylsulfanylethyl, wherein within $R^9$ the aromatic ring may be substituted further by 1 to 5 radicals independently selected from $(C_{1-6})$alkyl, cyano, halo, halo-substituted $(C_{1-4})$alkyl, nitro, —$X^4NR^{12}R^{12}$, —$X^4OR^{12}$, —$X^4C(O)R^{12}$, —$X^4C(O)OR^{12}$ and —$X^4SR^{12}$, wherein $X^4$ is a bond or $(C_{1-6})$allkylene; and $R^{12}$ at each occurrence independently is hydrogen, $(C_{1-6})$alkyl or halo-substituted $(C_{1-3})$alkyl; and
$R^{11}$ is —$X^4X^5R^{18}$, wherein $X^4$ is —$C(O)$—, $X^5$ is a bond and $R^{18}$ is (i) $(C_{3-12})$cycloalkyl$(C_{0-6})$alkyl, hetero$(C_{3-12})$cycloalkyl$(C_{0-6})$alkyl, $(C_{6-12})$aryl$(C_{1-6})$alkyl or hetero$(C_{5-12})$aryl$(C_{0-6})$alkyl or (ii) phenyl$(C_{0-6})$alkyl or hetero$(C_{5-6})$aryl$(C_{0-6})$alkyl, wherein said phenyl or heteroaryl is substituted by —$X^9OR^{24}$, —$X^9C(O)R^{24}$, —$X^9C(O)OR^{24}$, —$X^9C(O)NR^{24}R^{25}$, —$X^9NR^{24}R^{25}$, —$X^9NR^{25}C(O)R^{24}$, —$X^9NR^{25}C(O)OR^{24}$, —$X^9NR^{25}C(O)NR^{24}R^{25}$ or —$X^9NR^{25}C(NR^{25})NR^{24}R^{25}$, wherein $X^9$ is a bond or $(C_{1-6})$alkylene, $R^{24}$ is phenyl$(C_{0-6})$alkyl or hetero$(C_{5-6})$aryl$(C_{0-6})$alkyl and $R^{25}$ is hydrogen or $(C_{1-6})$alkyl, wherein within $R^{11}$ any aromatic ring system present may be substituted further by 1 to 5 substituents independently selected from $(C_{1-6})$alkyl, halo, halo-substituted $(C_{1-4})$alkyl, —$OR^{12}$, —$X^3SR^{12}$, —$C(O)OR^{12}$ and —$X^3NR^{12}C(O)OR^{12}$ wherein $X^3$ is a bond or $(C_{1-6})$alkylene and $R^{12}$ is hydrogen or $(C_{1-6})$alkyl; and the N-oxide derivatives, prodrug derivatives, protected derivatives, individual isomers and mixtures of isomers; and the pharmaceutically acceptable salts thereof.

13. The compound of claim 12 in which $R^9$ is a group having the following formula:

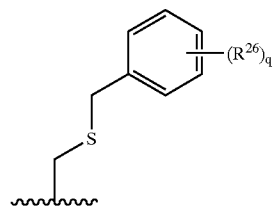

in which q is 0 to 5 and $R^{26}$ at each occurrence is independently selected from $(C_{1-4})$alkyl, cyano, halo, halo-substituted $(C_{1-4})$alkyl, nitro, —$OR^{12}$, —$SR^{12}$ and —$C(O)OR^{12}$, wherein $R^{12}$ is hydrogen, $(C_{1-3})$alkyl or halo-substituted $(C_{1-3})$alkyl; and the N-oxide derivatives, prodrug derivatives, protected derivatives, individual isomers and mixtures of isomers; and the pharmaceutically acceptable salts thereof.

14. The compound of claim 12 in which $R^9$ is benzyloxymethyl, 2-benzylsulfanylethyl, benzylsulfanylmethyl, 2-bromobenzylsulfanylmethyl, 4-tert-butylbenzylsulfanylmethyl, 2-chlorobenzylsulfanylmethyl, 4-chlorobenzylsulfanylmethyl, 2-(2-chlorophenylsulfanyl)ethyl, 3,4-dichlorobenzylsulfanylmethyl, 3,5-dimethylbenzylsulfanylmethyl, 2-fluorobenzylsulfanylmethyl, 2-iodobenzylsulfanylmethyl, 2-methylbenzylsulfanylmethyl, 3-methylbenzylsulfanylmethyl, 3-methylbenzylsulfanylmethyl, 4-methylbenzylsulfanyl-methyl, 2-(2-methylphenylsulfanyl)ethyl, 4-methoxybenzylsulfanylmethyl, 4-methoxybenzylsulfinylmethyl, 1-nitrobenzylsulfanylmethyl, 2-nitrobenzylsulfanylmethyl, 3-nitrobenzylsulfanylmethyl, 4-nitrobenzylsulfanylmethyl, pentafluorobenzylsulfanylmethyl, 2-phenoxyethyl, 2-phenoxyethyl 2-phenylsulfanylethyl, 2-pyrid-2-ylsulfanylethyl, 2-pyrid-4-ylsulfanylethyl, 4-trifluoromethylbenzylsulfanyl-methyl, 3-trifluoromethylbenzylsulfanylmethyl, 3-trifluoromethoxybenzylsulfanylmethyl, 4-trifluoromethoxybenzylsulfanylmethyl or 4-trifluorosulfanylbenzylsulfanylmethyl; and the N-oxide derivatives, prodrug derivatives, protected derivatives, individual isomers and mixtures of isomers; and the pharmaceutically acceptable salts thereof.

15. A method of treating a disease in an animal in which cathepsin S activity contributes to the pathology and/or symptomatology of the disease, which method comprising administering to the animal a therapeutically effective amount of a compound of Formula (I):

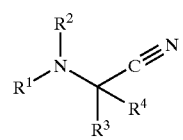

(I)

in which:
$R^1$ is a group of Formula (a):

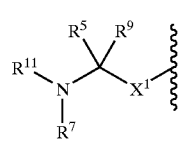

(a)

wherein:
$X^1$ is —$C(O)$— or —$CH_2S(O)_2$—;
$R^5$ is hydrogen;
$R^7$ is hydrogen;
$R^9$ is (i) $(C_{1-6})$alkyl substituted with —$OR^{14}$ or —$SR^{14}$, wherein $R^{14}$ is $(C_{3-6})$cycloalkyl$(C_{0-6})$alkyl, phenyl $(C_{0-6})$alkyl, biphenylyl$(C_{0-6})$alkyl or hetero$(C_{5-6})$aryl$(C_{0-6})$alkyl; wherein within $R^9$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^3NR^{12}R^{12}$, $-X^3NR^{12}C(O)OR^{12}$, $-X^3NR^{12}C(O)NR^{12}R^{12}$, $-X^3NR^{12}C(NR^{12})NR^{12}R^{12}$, $-X^3OR^{12}$, $-X^3SR^{12}$, $-X^3C(O)OR^{12}$, $-X^3C(O)NR^{12}R^{12}$, $-X^3S(O)_2NR^{12}R^{12}$, $-X^3P(O)(OR^3)OR^{12}$, $-X^3OP(O)(OR^3)OR^{12}$, $-X^3OC(O)R^{13}$, $-X^3OC(O)R^{13}$, $-X^3NR^{12}C(O)R^{13}$, $-X^3S(O)R^{13}$, $-X^3S(O)_2R^{13}$ and $-X^3C(O)R^{13}$, wherein $X^3$ is a bond or $(C_{1-6})$alkylene, $R^{12}$ at each occurrence independently is hydrogen, $(C_{1-3})$alkyl or halo-substituted $(C_{1-3})$alkyl and $R^{13}$ is $(C_{1-3})$alkyl or halo-substituted $(C_{1-3})$alkyl; and $R^{11}$ is $-X^4X^5R^{18}$, wherein $X^4$ is $-C(O)-$, $X^5$ is a bond and $R^{18}$ is (i) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl or (ii) phenyl$(C_{0-6})$alkyl or hetero$(C_{5-6})$aryl$(C_{0-6})$alkyl, wherein said phenyl or heteroaryl is substituted by $-X^9OR^{24}$, $-X^9C(O)R^{24}$, $-X^9C(O)OR^{24}$, $-X^9C(O)NR^{24}R^{25}$, $-X^9NR^{24}R^{25}$, $-X^9NR^{25}C(O)R^{24}$, $-X^9NR^{25}C(O)OR^{24}$, $-X^9NR^{25}C(O)NR^{24}R^{25}$ or $-X^9NR^{25}C(NR^{25})NR^{24}R^{25}$, wherein $X^9$ is a bond or $(C_{1-6})$alkylene, $R^{24}$ is phenyl$(C_{0-6})$alkyl or hetero$(C_{5-6})$aryl$(C_{0-6})$alkyl and $R^{25}$ is hydrogen or $(C_{1-6})$alkyl, wherein within $R^{11}$ any aromatic ring system present may be substituted further by 1 to 5 substituents independently selected from $(C_{1-6})$alkyl, halo, halo-substituted $(C_{1-4})$alkyl, $-OR^{12}$, $-X^3SR^{12}$, $-C(O)OR^{12}$ and $-X^3NR^{12}C(O)OR^{12}$ wherein $X^3$ is a bond or $(C_{1-6})$alkylene and $R^{12}$ is hydrogen or $(C_{1-6})$alkyl; and $R^2$ is hydrogen; and $R^3$ and $R^4$ are both hydrogen; and the N-oxide derivatives, prodrug derivatives, protected derivatives, individual isomers and mixtures of isomers; and the pharmaceutically acceptable salts thereof.

* * * * *